US007303883B2

(12) United States Patent
Kara et al.

(10) Patent No.: US 7,303,883 B2
(45) Date of Patent: Dec. 4, 2007

(54) DIAGNOSIS OF PARASITES

(75) Inventors: Anna Kate Ursula Kara, Singapore (SG); Robert Chin Yao Ting, Singapore (SG); Jill Maelon Tham, Singapore (SG); James Stuart Nelson, Singapore (SG); Theresa May Chin Tan, Singapore (SG)

(73) Assignees: The National University of Singapore, Singapore (SG); Agency for Science, Technology and Research, Centros (SG)

( * ) Notice: Subject to any disclaimer, the term of this patent is extended or adjusted under 35 U.S.C. 154(b) by 33 days.

(21) Appl. No.: 11/270,287

(22) Filed: Nov. 9, 2005

(65) Prior Publication Data

US 2006/0099627 A1    May 11, 2006

Related U.S. Application Data

(63) Continuation of application No. 09/369,992, filed on Aug. 6, 1999, now abandoned.

(30) Foreign Application Priority Data

| Feb. 5, 1997 | (WO) | PCT/IB98/00212 |
| Feb. 6, 1997 | (AU) | PO4953/97 |
| Apr. 21, 1997 | (AU) | PO6329/97 |
| Sep. 26, 1997 | (AU) | PO9481/97 |

(51) Int. Cl.
    *C12Q 1/68*    (2006.01)
(52) U.S. Cl. ......................................................... 435/6
(58) Field of Classification Search ................. 435/6
    See application file for complete search history.

(56) References Cited

U.S. PATENT DOCUMENTS

| 4,707,445 A | 11/1987 | McCutchan et al. |
| 5,792,609 A | 8/1998 | Wataya et al. |
| 6,143,756 A | 11/2000 | Kara et al. |
| 6,268,160 B1 | 7/2001 | Clough et al. |
| 6,313,090 B1 | 11/2001 | Rogers et al. |
| 6,766,817 B2 | 7/2004 | da Silva |
| 2002/0058266 A1 | 5/2002 | Clough et al. |

OTHER PUBLICATIONS

Feagin et al. (1992) "Homologies Between the Contiguous and Fragmented rRNAs of the Two *Plasmodium falciparum* Extrachromosomal DNAs Are Limited to Core Sequences" *Nucleic Acids Research* 20:879-887.
Gardner et al. (1994) "Nine Duplicated tRNA Genes on the Plastid-Like DNA of the Malaria Parasite *Plasmodium falciparum*" *Gene* 144:307-308.
Gardner et al. (1993) "Sequence and Organization of Large Subunit rRNA Genes from the Extrachromosomal 35 kb Circular DNA of the Malaria Parasite *Plasmodium falciparum*" *Nucleic Acids Research* 21:1067-1071.

Genbank Accession No. M76611, *Plasmodium falciparum* sequences: small subunit rRNA, large subunit rRNA, cytochrome oxidase subunit I, etc. (1998).
Genbank Accession No. X95275, *Plasmodium falciparum* plastid-like DNA (1997).
Genbank Accession No. X95276, *Plasmodium falciparum* plastid-like DNA (1997).
Preiser et al. (1995) "tRNA Genes Transcribed from the Plastid-Like DNA of *Plasmodium falciparum*" *Nucleic Acids Research* 23:4329-4336.
Williamson et al. (1994) "The Evolutionary Origin of the 35 kb Circular DNA of *Plasmodium falciparum*: New Evidence Supports a Possible Rhodophyte Ancestry" *Mol. Gen. Genet.* 243:249-252.
Wilson et al. (1996) "Complete Gene Map of the Plastid-Like DNA of the Malaria Parasite *Plasmodium falciparum*" *J. Mol. Biol.* 261:155-172.
Gardner et al. (1994) "Phylogenetic Analysis of the *rpo*B Gene from the Plastid-Like DNA of *Plasmodium falciparum*" *Molecular and Biochemical Parasitology* 66:221-231.
Gardner et al. (1991) "Organisation and Expression of Small Subunit Ribosomal RNA Genes Encoded by a 35-Kilobase Circular DNA in *Plasmodium falciparum*" *Molecular and Biochemical Parasitology* 48:77-88.
Gardner et al. (1991) "A Circular DNA In Malaria Parasites Encodes and RNA Polymerase Like That of Prokaryotes and Chloroplasts" *Molecular and Biochemical Parasitology* 44:115-124.
Vaidya et al. (1989) "Sequences Similar to Genes for Two Mitochondrial Proteins and Portions of Ribosomal RNA in Tandemly Arrayed 6-Kilobase-Pair DNA of a Malarial Parasite" *Molecular and Biochemical Parasitology* 35:97-108.
Ayyanathan, K et al. (1996) "Identification and characterization of a generic DNA probe capable of detecting plasmodial infections in blood"; Molecular and Cellular Probes 10:273-278.
Das, A et al. (1996) "A One-Step Lysis Procedure for 18S Ribosomal RNA-Based Diagnosis of Infection by *Plasmodium* Species"; *Analytical Biochemistry* 241:262-264.
Fichera, ME (1997) *Nature* vol. 390, Nov. 27, 1997.
Gardner, MJ et al. (1994) "Nine duplicated tRNA genes on the plastid-like DNA of the malaria parasite *Plasmodium falciparum*"; *Gene* 144:307-308.
Gardner et al. (1993) *Nucleic Acid Res.* 21(5):1067-1071, and accession No. X61660.
Gardner, MJ et al. (1991) "A circular DNA in malaria parasites encodes an RNA polymerase like that of prokaryotes and chloroplasts"; 44:115-124.

(Continued)

*Primary Examiner*—Mark Navarro
(74) *Attorney, Agent, or Firm*—Greenlee Winner and Sullivan PC

(57) ABSTRACT

Detection of *Plasmodium* ssp. by analysis of extrachromosomal DNA. It has been found that the molecular composition, physical arrangements, and nucleotide sequences of the extrachromosomal plastid-like element and mitochondrial element are highly conserved in different *Plasmodium* ssp. The high degree of homology has been used to design genera-specific or species specific diagnostic assays with a low frequency of false negatives. Plastid and mitochondrial DNA sequences are disclosed. The use of the sequences is claimed for detection, prophylactic, and therapeutic treatment of *Plasmodium* ssp. infection in human or other animals.

17 Claims, 38 Drawing Sheets

OTHER PUBLICATIONS

Gardner, MJ et al (1991) Organization and expression of small subunit ribosomal RNA genes encoded by a 35-kilobase circular DNA in *Plasmodium falciparum*.

McCutchan, TF et al. (1984) "Evolutionary Relatedness of *Plasmodium* Species as Determined by the Structre of DNA"; *Science* 225(4664):808-811.

Krungkrai, J et al. (1993) "*Plasmodium berghei*: Partial Purification and Characterization of the Mitochondrial Cytochrome c Oxidase"; *Experimental Parasitology* 77:136-146.

McCutchan, TR et al. (1988) "Primary sequences of two small subunit ribosomal RNA genes from *Plasmodium falciparum*"; *Molecular and biochemical parasitology* 28(1):63-68.

Obst, M et al (1990) "Detection of DNA sequences in *Plasmodium berghei* by means of in situ hybridization"; *Histochemistry* 94:101-107.

Rich et al. (2000) *Parasitology* 16(9):390-396.

Shaw, MK et al. (1996) "Localization of ribosomal RNA and Pbs21-mRNA in the sexual stages of *Plasmodium berghei* using electron microscope in situ hybridization"; *European Journal of Cell Biology* 71:270-276.

Snounou, G et al. (1992) Identification and quantification of rodent malaria strains and species using gene probes; *Parasitology* 195(pt 1):21-27.

Weissig, V et al. (1997) "Topoisomerase II Inhibitors Induce Cleavage of Nuclear and 35-kb Plastid DNAs in the Malarial Parasite *Plasmodium falciparum*"; *DNA and Cell Biology* 16(12):1483-1492.

Wilson, RJM et al. (1996) *J. Mol. Biol.* 261:155-172.

Yap, MWC et al. (1997) :Partial nucleotide sequence and organisation of extrachromosomal plastid-like DNA in *Plasmodium berghei; Gene* 200:91-98.

| |
|---|
| FIGURE 9 (CONT. I) |
| FIGURE 9 (CONT. II) |
| FIGURE 9 (CONT. III) |
| FIGURE 9 (CONT. IV) |
| FIGURE 9 (CONT. V) |
| FIGURE 9 (CONT. VI) |
| FIGURE 9 (CONT. VII) |
| FIGURE 9 (CONT. VIII) |
| FIGURE 9 (CONT. IX) |
| FIGURE 9 (CONT. X) |

FIGURE 9

```
                                                                      60
Pf(C10)    GACCTGCATGAAAGATGTAACGACTTAAATGCTGTCTCTTAAAAAAATCTTAATGAAATAA
Pf10/P     GACCTGCATGAAAGATGTAACGACTTAAATGCTGTCTGTCTTAAAAAAATCTTAATGAAATAA
Pf11/P     GACCTGCATGAAAGATGTACCGACTTAAATGCTGTCTTACAAAAAAGCTTAATGAAATAA
Pf19/I     GACCTGCATGAAAGATGTAACGACTTAAATGCTGTCTGTCTTAAAAAAATCTTAATGAAATAA
Pf20/L     GACCTGCATGAAAGATGTAACGACTTAAATGCTGTCTGTCTTAAAAAAATCTTAATGAAATAA
Pf18/S     GACCTGCATGAAAGATGTAACGACTTAAATGCTGTCTGTCTTAAAAAAATCTTAATGAAATAA
Pv12/P     GACCTGCATGAAAGATGTAACGACTTAAATGCTGTCTGTCTTAAAAAAATCTTAATGAAATAA
Pv13/P     GACCTGCATGAAAGATGTAACGACTTAAATGCTGTCTGTCTTAAAAAAATCTTAATGAAATAA
Pv15/I     GACCTGCATGAAAGATGTAACGACTTAAATGCTGTCTGTCTTAAAAAACTCTTAATGAAATAA
Pv16/L     GACCTGCATGAAAGATGTAACGACTTAAATGCTGTCTGTCTTAAAAAAATCTTAATGAAATAA
Pv17/S     GACCTGCATGAAAGATGTAACGACTTAAATGCTGTCTGTCTTAAAAAAATCTTAATGAAATAA
Pv86/C     GACCTGCATGAAAGATGTAACGACTTAAATGCTGTCTGTCTTAAAAAAATCTTAATGAAATAA
Pm1/S      GACCTGCATGAAAGATGTAACGACTTAAATGCTGTCTGTCTTAAAAAAATCTTAATGAAATAA
Pm38/S     GACCTGCATGAAAGATGTAACGACTTAAATGCTGTCTGTCTTAAAAAAATCTTAATGAAATAA
Po35/S     GACCTGCATGAAAGATGTAACGACTTAAATGCTGTCTGTCTTAAAAAAATCTTAATGAAATAA
Po36/S     GACCTGCATGAAAGATGTAACGACTTAAATGCTGTCTGTCTTAAAAAAATCTTAATGAAATAA
Pb(ANKA)   GACCTGCATGAAAGATGTAACGACTTAAATGCTGTCTGTCTTAAAAAAATCTTAATGAAATAA
           1
```

FIGURE 9 (CONT. I)

```
                61                                                            120
Pf(C10)   AATTATCTGTGAAGATACAGAGATTCTTATATTAGGACAG.AAAGACCCTATGAAGCTTTA
Pf10/P    AATTATCTGTGAAGATACAGAGATTCTTATATTAGGACAG.AAAGACCCTATGAAGCTTTA
Pf11/P    AATTATCTGTGAAGATACAGATGTCTTATATTAGGACAG.AAAGACCCTATGAAGCTTTG
Pf19/I    AATTATCTGTGAAGATACAGAGATTCTTATATTAGGACAG.AAAGACCCTATGAAGCTTTA
Pf20/L    AATTATCTGTGAAGATACAGAGATTCTTATATTAGGACAG.AAAGACCCTATGAAGCTTTA
Pf18/S    AATTATCTGTGAAGATACAGAGATTCTTATATTAGGACAG.GAAGACCCTATGAAGCTTTA
Pv12/P    AATTATCTGTGAAGATACAGAGATTCTTATATTAGGACAG.AAAGACCCTATGAAGCTTTA
Pv13/P    AATTATCTGTGAAGATGCAGAGATTCTTATATTAGGACAG.AAAGACCCTATGAAGCTTTA
Pv15/I    AATTATCTGTGAAGATGCAGAGATTCTTATATTAGGACAG.AAAGACCCTATGAAGCTTTA
Pv16/L    AATTATCTGTGAAGATACAGAGATTCTTATATTAGGACAG.AAAGACCCTATGAAGCTTTA
Pv17/S    AATTACCTGTGAAGATGCAGAGATTCTTATATTAGGACAG.AAAGACCCTATGAAGCTTTA
Pv86/C    AATTATCTGTGAAGATGCAGAGATTCTTATATTAGGACAG.AAAGACCCTATGAAGCTTTA
Pm1/S     AATTATCTGTGAAGATGCAGAGATTCTTATATTAGGACAG.AAAGACCCTATGAAGCTTTA
Pm38/S    AATTATCTGTGAAGATGCAGAGATTCTTATATTAGGACAG.AAAGACCCTATGAAGCTTTA
Po35/S    AATTATCTGTGAAGATGCAGAGATTCTTATATTAGGACAG.AAAGACCCTATGAAGCTTTA
Po36/S    AATTATCTGTGAAGATGCAGAGATTCTTATATTAGGACAG.AAAGACCCTATGAAGCTTTA
Pb(ANKA)  AATTATCTGTGAAGATGCAGAGATTCTTATATTAGGACAG.AAAGACCCTATGAAGCTTTA
```

FIGURE 9 (CONT. II)

```
            121                                                          180
Pf(C10)     CTATTAATAATAATGAAAATATATATATTTAACATAGTATAAATGGGAAACAATAATAT
Pf10/P      CTATTAATAATAATGAAAATATATATATTTAACATAGTATAAATGGGAAACAATAATAT
Pf11/P      CTATTAATAAATAATGAAAATATATATATTTAACATAGTATAAATGGGAAACAATAATAT
Pf19/I      CTATTAATAAATAATGAAAATATATATATTTAACATAGTATAAATGGGAAACAATAATAT
Pf20/L      CTATTAATAAATAATGAAAATATATATATTTAACATAGTATAAATGGGAAACAATAATAT
Pf18/S      CTATTAATAAATAATGAAAATATATATATTTAACATAGTATAAATGGGAAACAATAATAT
Pv12/P      CTATGAATAGATATTGAAAATATATATATATAGAGCATAGCATAAATGGGAAATAATGATAT
Pv13/P      CTATGAATAGATATTGAAAATATATATATATAGAGCATAGCATAAATGGGAAATAATGATAT
Pv15/I      CTATTAATAAATAATGAAAATATATATATTTAACATAGTATAAATGGGAAACAATAATAT
Pv16/L      CTATTAATAAATAATGAAAATATATATATTTAACATAGTATAAATGGGAAACAATAATAT
Pv17/S      CTATGAATAGATATTGAAAATATATATATATAGAGCATAGCATAAATGGGAAATAATGATAT
Pv86/C      CTATGAATAGATATTGAAAATATATATATATAGAGCATAGCATAAATGGGAAATAATGATAT
Pm1/S       CTATGAATAGATATTGAAAATATATATATATAGAGCATAGCATAAATGGGAAATAATGATAT
Pm38/S      CTATGAATAGATATTGAAAATATATATATATAGAGCATAGCATAAATGGGAAATAATGATAT
Po35/S      CTATGAATAGATATTGAAAATATATATATATAGAGCATAGCATAAATGGGAAATAATGATAT
Po36/S      CTATGAATAGATATTGAAAATATATATATATAGAGCATAGCATAAATGGGAAATAATGATAT
Pb(ANKA)    CTATTAATAGATATTGAAAATATATATATATAACATAGAATAAATGGGAAGTAGTAATAT
```

FIGURE 9 (CONT. III)

```
         181                                                          240
Pf(C10)  .TATTTCTCTTGGAAATAATTAGTTAAAAATGAAATACCATTTTATTTATATATAAATTCT
Pf10/P   TATTTTCTCTTGGAAATAATTAGTTAAAAATGAAATACCATTTTATTTATATATAAATCCT
Pf11/P   TATTTTCTCTTGGAAATAATTAGTTAAAAATGAAATACCATTTTATTTATATATAAATTCT
Pf19/I   TATTTTCTCTTGGAAATAATTAGTTAAAAATGAAATACCATTTTATTTACATATAAATTCT
Pf20/L   TATTTTCTCTTGGAAATAATTAGTTAAAA.TGAAATACCATTTTATTTATATATAAATTCT
Pf18/S   TATTTTCTCTTGGAAATAATTAGTTAAAAATGAAATACCATTTTATTTATATATAAATTCT
Pv12/P   TATTTTTTCTTGGAAATAATAGTGTAATTGTAATTGAAATACCATTTTTATATATAAATTCT
Pv13/P   TATTTTTTCTTGGAAATAATTAGTTAAAAATGAAATACCATTTTATATATATAAATTCT
Pv15/I   TATTTTCTCTTGGAAATAATTAGTTAAAAATGAAATACCATTTTATTTATATATAAATTCT
Pv16/L   TATTTTCTCTTGGAAATAATTAGTTAAAAATGAAATACCATTTTATTTATATATAAATTCT
Pv17/S   TATTTTTTTTGGAAATAGTAGTGTAATTGTAATTGTAAATGAAATACCATTTTTATATATAAATCCT
Pv86/C   TATTTTTTTTGGAAATAGTAGTGTAATTGTAATTGTAAATGAAATACCATTTTTATATATAAATTCT
Pm1/S    TATTTTTTTTGGAAATAGTAGTGTAATTGTAATTGTAAATGAAATACCATTTTTATATATAAATTCT
Pm38/S   TATTTTTTTGGAAATAGTAGTGTAATTGTAATTGTAAATGAAATACCATTTTTTATATATAAATTCT
Po35/S   TATTTTTTTGGAAATAGTAGTGTAATTGTAATTGTAAATGAAATACCATTTTTTATATATAAATTCT
Po36/S   TATTTTTTTTGGAAATAATGTAATTGTAATTGTAAATGAAATACCATTTTTATATATATAAATTCT
Pb(ANKA) TATTTTTTTGGAAATAATGTAATTGTAAATGTAAATGAAATACCATTTTTATATATATAAATTCT
```

FIGURE 9 (CONT. IV)

```
                  241                                                        300
Pf(C10)    TATAGAAATTTTATAACA.AATTTTTAAACAA.TATTTATGAGATAGTTTGACTGGGG.C
Pf10/P     TATAGAAATTTTATAACA.AATTTTTAAACAGAATTTTAGACAACTATTCATGAGATAGTTTGACTGGGG.C
Pf11/P     TATAGAAATTTTATAACA.AATTTTTAAACAA.TATTTATGAGATAGTTTGACTGGGG.C
Pf19/I     TATAGAAATTTTATAACA.AATTTTTAAACAA.TATTTATGAGATAGTTTGACTGGGG.C
Pf20/L     TATAGAAATTTTATAACA.AATTTTTAAACAA.TATTTATGAGATAGTTTGACTGGGG.C
Pf18/S     TATAGAAATTTTATAACA.AATTTTTAAACAA.TATTTATGAGATAGTTTGACTGGGG.C
Pv12/P     TAAAAAAATTTTTTAACA.AATTTTTAAACAG.TATTTATAAGATAGTTTGACTGGGG.C
Pv13/P     TAAAAAAATTTTTTAACA.AATTTTTAAACAG.TATTTATAAGATAGTTTGACTGGGG.C
Pv15/I     TATAGAAATTTTATAACA.AATTTTTAAACAA.TATTTATGAGATAGTTTGACTGGGG.C
Pv16/L     TAAAAAAATTTTTTAACA.AATTTTTAAACAG.TATTTATAAGATAGTTTGACTGGGG.C
Pv17/S     TAAAAAAATTTTTTAACA.AATTTTTAAACAG.TATTTATAAGATAGTTTGACTGGGG.C
Pv86/C     TAAAAAAATTTTTTAACA.AATTTTTAAACAG.TATTTATAAGATAGTTTGACTGGGG.C
Pm1/S      TAAAAAATTTT.AACA.AATTTTTAAACAG.TATTTATAAGATAGTTTGACTGGGG.C
Pm38/S     TAAAAAAATTTTTTAACA.AATTTTTAAACAG.TATTTATAAGATAGTTTGACTGGGG.C
Po35/S     TAAAAAAATTTTTTAACA.AATTTTTAAACAG.TATTTATAAGATAGTTTGACTGGGGC
Po36/S     TAAAAAAATTTTTTAACA.AATTTTTAAACAG.TATTTATAAGATAGTTTGACTGGGG.C
Pb(ANKA)   TATAAAAATTTTTTATAACA.AAATTTTTAAACAA.TATTTATAAGATAGTTTGACTGGGG.C
```

FIGURE 9 (CONT. V)

```
              301                                                           360
Pf(C10)   GGTCTCCTCCTATATATAAACGGAGGAGTACAATGTTATATTTATTATATAAAGATATAA
Pf10/P    GGTCTCCTCCTATATATAAACGGAGGAGTACAATGTTATATTTATTATATAAAGATATAA
Pf11/P    GGTCTCCTCCTATATATAAACAGAGGAGTACAATGTTATATTTATTATATAAAGATATAA
Pf19/I    GGTCTCCTCCTATATATAAACGGAGGAGTACAATGTTATATTTATTATATAAAGATATAA
Pf20/L    GGTCTCCTCCTATATATAAACGGAGGAGTACAATGTTATATTTATTATATAAAGATATAA
Pf18/S    GGTCTCCTCCTATATATAAACGGAGGAGTACAATGTTATATTTATTATATAAAGATATAA
Pv12/P    GGTCTCCTCCTATATATAAAACGGAGGAGTACAAAGTTATATATTTATATAAAGATATA.
Pv13/P    GGTCTCCTCCTATATATAAAACGGAGGAGTACAAAGTTATATATGTTATATAAAGATATA.
Pv15/I    GGTCTCCTCCTATATATAAACGGAGGAGTACAATGTTATATTTATTATATAAAGATATAA
Pv16/L    GGTCTCCTCCTATATATAAACGGAGGAGTACAATGTTATATTTATTATATAAAGATATAA
Pv17/S    GGTCTCCTCCTATATATAAACGGAGGAGTACAATGTTATATATGTTATATAAAGATATA.
Pv86/C    GGTCTCCTCCTATATAAAAAACGGAGGAGTACAAAGTTATATATGTTATATAAAGATATA.
Pm1/S     GGTCTCCTCCTATATAAAAAACGGAGGAGTACAAAGTTATATATGTTATATAAAGATATA.
Pm38/S    GGTCTCCTCCTATATAAAAAACGGAGGAGTACAAAGTTATATATGTTATATAAAGATATA.
Po35/S    GGTCTCCTCCTATATAAAAAACGGAGGAGTACAAAGTTATATATGTTATATAAAGATATA.
Po36/S    GGTCTCCTCCTATATAAAAAACGGAGGAGTACAAAGTTATATATGTTATATAAAGATATA.
Pb(ANKA)  GGTCTCCTCCTATATAAAAAACGGAGGAGTGTACAATGTTATATTTATTATATAAAGATAAA.
```

FIGURE 9 (CONT. VI)

```
                361                                                        420
Pf(C10)    TATATAATTAACTGTAAAATTTACAAATTAAACAGAGATAAATGTCGGTCTTAATGATCC
Pf10/P     TATATAATTAACTGTAAAATTTACAAATTAAACAGAGATAAATGTCGGTCTTAATGATCC
Pf11/P     TATATAATTAACTGTAAAATTTACAAATTAAACAGAGATAAATGTCGGTCTTAATGATCC
Pf19/I     TATATAATTAACTGTAAAATTTACAAATTAAACAGAGATAAATGTCGGTCTTAATGATCC
Pf20/L     TATATAATTAACTGTAAAATTTACAAATTAAACAGAGATAAATGTCGGTCTTAATGATCC
Pf18/S     TATATAATTAACTGTAAAATTTACAAATTAAACAGAGATAAATGTCGGTCTTAATGATCC
Pv12/P     TATATAATTAACTGTAAAATTAACAAATTAAACAGAGATAAATGTCGGTCTTAATGATCC
Pv13/P     TATATAATTAACTGTAAAATTCACAAATTAAACAGAGATTAATGTCGGTCTTAATGATCC
Pv15/I     TATATAATTAACTGTAAAATTTACAAATTAAACAGAGATAAATGTCGGTCTTAATGATCC
Pv16/L     TATATAATTAACTGTAAAATTTACAAATTAACAGAGATAAATGTCGGTCTTAATGATCC
Pv17/S     TATATAATTAACTGTAAAATTTACAAATTAATGACAGAGATTAATGTCGGTCTTAATGATCC
Pv86/C     TATATAATTAACTGTAAAATTTACAAATTAAACAGAGATTAATGTCGGTCTTAATGATCC
Pm1/S      TATATAATTAACTGTAAAATTTACAAATTAACAGAGATTAATGTCGGTCTTAATGATCC
Pm38/S     TATATAATTAACTGTAAAATTAACAAGTTAAACAGAGATTAATGTCGGTCTTAATGATCC
Po35/S     TATATAATTAACTGTAAAATTAACAAATTAAACAGAGATTAATGTCGGTCTTAATGATCC
Po36/S     TATATAAATTAACTGTAAAATTAACAAATTAAACAGAGATTAATGTCGGTCTTAATGATCC
Pb(ANKA)   TATATAATTAACTGTAAAATTTACAAATTAAACAGAGATTAATGTCGGTCTTAATGATCC
```

FIGURE 9 (CONT. VII)

|  | 421 | 480 |
|---|---|---|
| Pf(C10) | GATAATTATTAGTAATAATAAAATTATCGCTTAACGGATAAAAGTTACTCTAGGGATAACAG | |
| Pf10/P | GATAATTATTAGTAATAATAAAATTATCGCTTAACGGATAAAAGTTACTCTAGGGATAACAG | |
| Pf11/P | GATAATTATTAGTAATAATAAAATTATCGCTTAACGGATAAAAGTTACTCTAGGGATAACAG | |
| Pf19/I | GATAATTATTAGTAATAATAAAATTATCGCTTAACGGATAAAAGTTACTCTAGGGATAACAG | |
| Pf20/L | GATAATTATTAGTAATAATAAAATTATCGCTTAACGGATAAAAGTTACTCTAGGGATAACAG | |
| Pf18/S | GATAATTATTAGTAATAATAAAATTATCGCTTAACGGATAAAAGTTACTCTAGGGATAACAG | |
| Pv12/P | GATAATTATTAATGATAAAATTATCGCTTAACGGATAAAAGTTACTCTAGGGATAACAG | |
| Pv13/P | GATAATTATTAATGATAAAATTATCGCTTAACGGATAAAAGTTACTGTAGGGATAACAG | |
| Pv15/I | GATAATTATTAGTAATAATAAAATTATCGCTTAACGGATAAAAGTTACTCTAGGGATAACAG | |
| Pv16/L | GATAATTATTAGTAATAATAAAATTATCGCTTAACGGATAAAAGTTACTCTAGGGATAACAG | |
| Pv17/S | GATAATTATTAATGATAAAATTATCGCTTAACGGATAAAAGTTACTCTAGGGATAACAG | |
| Pv86/C | GATAATTATTAATGATAAAATTATCGCTTAACGGATAAAAGTTACTCTAGGGGTAACAG | |
| Pm1/S | GATAATTATTAATGATAAAATTATCGCTTAACGGATAAAAGTTACTCTAGGGATAACAG | |
| Pm38/S | GATAATTATTAATGATAAAATTATCGCTTAACGGATAAAAGTTACTCTAGGGATAACAG | |
| Po35/S | GATAATTATTAATGATAAAATTATCGCTTAACGGATAAAAGTTACTCTAGGGATAACAG | |
| Po36/S | GATAATTATTAATAATAAAATTATCGCTTAACGGATAAAAGTTACTCTAGGGATAACAG | |
| Pb(ANKA) | GATAATTATTAATAATAAAATTATCGCTTAACGGATAAAAGTTACTCTAGGGATAACAG | |

FIGURE 9 (CONT. VIII)

```
          481                                                        540
Pf(C10)   GCTAATCTTTTCCGAGAGTCCATATTGACGAAAAGGTTTGGCACCTCGATGTCGGCTTAT
Pf10/P    GCTAATCTTTTCCGAGAGTCCATATTGACGAAAAGGTTTGGCACCTCGATGTCGGCTTAT
Pf11/P    GCTAATCTTTTCCGAGAGTCCATATTGACGAAAAGGTTTGGCACCTCGATGTCGGCTTAT
Pf19/I    GCTAATCTTTTCCGAGAGTCCATATTGACGAAAAGGTTTGGCACCTCGATGTCGGCTTAT
Pf20/L    GCTAATCTTTTCCGAGAGTCCATATTGACGAAAAGGTTTGGCACCTCGATGTCGGCTTAT
Pf18/S    GCTAATCTTTTCCGAGAGTCCATATTGACGAAAAGGTTTGGCACCTCGATGTCGGCTTAT
Pv12/P    GCTAATCTTTTCCGAGAGTCCATATTGACGAAAAGGTTTGGCACCTCGATGTCGGCTTAT
Pv13/P    GCTAATCTTTTCCGAGAGTCCATATTGACGAAAAGGTTCGGCACCTCGATGTCGGCTTAT
Pv15/I    GCTAATCTTTTCCGAGAGTCCATATTGACGAAAAGGTTTGGCACCTCGATGTCGGCTTAT
Pv16/L    GCTAATCTTTTCCGAGAGTCCATATTGACGAAAAGGTTTGGCACCTCGATGTCGGCTTAT
Pv17/S    GCTAATCTTTTCCGAGAGTCCATATTGACGAAAAGGTTTGGCACCTCGATGTCGGCTTAT
Pv86/C    GCTAACCTTTTCCGAGAGTCCATATTGACGAAAAGGTTTGGCACCTCGATGTCGGCTTAT
Pm1/S     GCTAATCTTTTCCGAGAGTCCATATTGACGAAAAGGTTTGGCACCTCGATGTCGGCTTAT
Pm38/S    GCTAATCTTTTCCGAGAGTCCATATTGACGAAAAGGTTTGGCACCTCGATGTCGGCTTAT
Po35/S    GCTAATCTTTTCCGAGAGTCCATATTGTTGACGAAAAGGTTTGGCACCTCGATGTCGGCTTAT
Po36/S    GCTAATCTTTTCCGAGAGTCCATATTGACGAAAAGGTTTGGCACCTCGATGTCGGCTTAT
Pb(ANKA)  GCTAATCTTTTCCGAGAGTCCATATTGACGAAAAGGTTTGGCACCTCGATGTCGGCTTAT
```

FIGURE 9 (CONT. IX)

```
                                                                                600
        541
Pf(C10)  CGCATCCTAAAGCAGTAGTAGTATGTTTTAAGGGTAAGTCTGTT.CGCCTATTAAAGCGATAC
Pf10/P   CGCATCCTAAAGCAGTAGTAGTATGTTTTAAGGGTAAGTCTGTT.CGCCTATTAAAGCGATAC
Pf11/P   CGCATCCTAAAGCAGTAGTAGTATGCCCCAAGGGTAAGTCTGTT.CGCCTATTAAAGCGATAC
Pf19/I   CGCATCCTAAAGCAGTAGTAGTATGTTTTAAGGGTAAGTCTGTT.CGCCTATTAAAGCGATAC
Pf20/L   CGCATCCTAAAGCAGTAGTAGTATGTTTTAAGGGTAAGTCTGTT.CGCCTATTAAAGCGATAC
Pf18/S   CGCATCCTAAAGCAGTAGTAGTATGTTTTAAGGGTAAGTCTGTT.CGCCTATTAAAGCGATAC
Pv12/P   CGCATCCTAAAGCAGTAGTAGTATGTTTTAAGGGTAAGTCTGTT.CGCCTATTAAAGCGATAC
Pv13/P   CGCATCCTAAAGCAGTAGTAGTATGTTTTAAGGGTAAGTCTGTT.CGCCTATTAAAGCGATAC
Pv15/I   CGCATCCTAAAGCAGTAGTAGTATGTTTTAAGGGTAAGTCTGTT.CGCCTATTAAAGCGATAC
Pv16/L   CGCATCCTAAAGCAGTAGTAGTATGTTTTAAGGGTAAGTCTGTTACGCCTATTAAAGCGATAC
Pv17/S   CGCATCCTAAAGCAGTAGTAGTATGTTTTAAGGGTAAGTCTGTTTCGCCTATTAAAGCGATAC
Pv86/C   CGCATCCTAAAGCAGTAGTAGTATGTTTTAAGGGTAAGTCTGTT.CGCCTATTAAAGCGATAC
Pm1/S    CGCATCCTAAAGCAGTAGTAGTATGTTTTAAGGGTAAGTCTGTT.CGCCTATTAAAGCGATAC
Pm38/S   CGCATCCTAAAGCAGTAGTAGTATGTTTTAAGGTAAGTCTGTT.CGCCTATTAAAGCGATAC
Po35/S   CGCATCCTAAAGCAGTAGTAGTATGTTTTAAGGGTAAGTCTGTT.CGCCTATTAAAGCGATAC
Po36/S   CGCATCCTAAGCAGTAGTAGTATGTTTTAAGGGTAAGTCTGTT.CGCCTATTAAAGCGATAC
Pb(ANKA) CGCATCCTAAGGCAGTAGTAGTATGTTTTAAGGGTAAGTCTGTT.CGCCTATTAAAGCGATAC
```

FIGURE 9 (CONT. X)

| FIGURE 10 (CONT. I) |
|---|
| FIGURE 10 (CONT. II) |
| FIGURE 10 (CONT. III) |
| FIGURE 10 (CONT. IV) |
| FIGURE 10 (CONT. V) |
| FIGURE 10 (CONT. VI) |
| FIGURE 10 (CONT. VII) |
| FIGURE 10 (CONT. VIII) |
| FIGURE 10 (CONT. IX) |
| FIGURE 10 (CONT. X) |
| FIGURE 10 (CONT. XI) |
| FIGURE 10 (CONT. XII) |
| FIGURE 10 (CONT. XIII) |
| FIGURE 10 (CONT. XIV) |

FIGURE 10

```
           1                                                            60
PfcoxI     GACTGTATGGATCAAATATTTCTCATTTATATCCGAGCCTCA......TGTTA.........
Pf47coxI   GACTGTATGGATCGAATATTTCTCATTTATATCCGAGCCTCA......TGTTA.........
Pv15coxI   GACTGTATGGATCGAATCTTACTTATTCATATCCAAGCCTCACTTATTGTTAATTATATA
Pv16coxI   GACTGTATGGATCGAATCTTACTTATTCATATCCAAGCCTCACTTATTGTTAATTATATA
Pv32coxI   GACTGTATGGATCGAATCTTACTTATTCATATCCAAGCCTCACTTATTGTTAATTATATA
Pv37coxI   GACTGTATGGATCGAATCTTACTTATTCATATCCAAGCCTCACTTATTGTTAATTATATA
Po35coxI   GACTGTATGGATCGAATCTTACTTATTCATATCCAAGCCTCACTTATTGTTAATTATATA
Pm58coxI   GACTGTATGGATCGAATCTTACTTATTCATATCCAAGCCTCACTTATTGTTAATTATATA 61                                                           120
PfcoxI     ........TTTTTATTGTTTTTAAATAGATATTCACTTATTACAAATTGTAACCATAAAACT
Pf47coxI   ........TTTTTATTGTTTTTAAATAGATATTCACTTATTACAAATTGTAACCATAAAACT
Pv15coxI   TTATATTTTTT..TGTTTTTGTTTCCAATAGATATACACTTATTACAAATTGCAATCATAAAACT
Pv16coxI   TTATATTTTTT..TGTTTTT.GTTTCCAATAGATATACACTTATTACAAATTGCAATCATAAAACT
Pv32coxI   TTATATTTTTT..TGTTTTT.TGTTTCCAATAGATATACACTTATTACAAATTGCAATCATAAAACT
Pv37coxI   TTATATTTTT...TGTTTTT.TGTTTCCAATAGATATACACTTATTACAAATTGCAATCATAAAACT
Po35coxI   TTATATTTTT...TGTTTTT..TGTTTCAATAGATATACACTTATTACAAATTGCAATCATAAAACT
Pm58coxI   TTATATTTTT...TGTTTTT..TGTTTCAATAGATATACACTTATTACAAATTGCAATCATAAAACT
```

FIGURE 10 (CONT. I)

```
                       121                                                      180
PfcoxI      TTAGGATTATACTATTATGGTTTTCATTTTTATTTGGTAGTTATGGATTTTTATTATCA
Pf47coxI    TTAGGATTATACTATTATGGTTTTCATTTTTATTGGTAGTTATGGATTTTTATTATCA
Pv15coxI    TTAGGTCTATACTATTATGGTTTTCATTTTTATTGGTAGTTATGGTTTTTATTATCT
Pv16coxI    TTAGGTCTATACTATTATGGTTTTCATTTTTATTGGTAGTTATGGTTTTTATTATCT
Pv32coxI    TTAGGTCTATACTATTATGGTTTTCATTTTTATTGGTAGTTATGGTTTTTATTATCT
Pv37coxI    TTAGGTCTATACTATTATGGTCTTCATTTTTATTGGTAGTTATGGTTTTTATTATCT
Po35coxI    TTAGGTCTATACTATTATGGTTTTCATTTTTATTGGTAGTTATGGTTTTTATTATCT
Pm58coxI    TTAGGTCTATACTATTATGGTTTTCATTTTTATTGGTAGTTATGGTTTTTATTATCT 181                                                      240
PfcoxI      GTAATACTACGTACTGAATTATATTCTTCATCTTTAAGAATAATTGCACAAGAAAATGTA
Pf47coxI    GTAATACTACGTACTGAATTATATTCTTGAATCTTCATCTTTAAGAATAATTGCACAAGAAAATGTA
Pv15coxI    GTTATTTACGTACAGAATTATATTCTTCTCTTCTTTAAGAATAATTGCACAAGAAAATGTT
Pv16coxI    GTTATTTACGTACAGAATTATATTCTTCTCTTCTTTAAGAATAATTGCACAAGAAAATGTT
Pv32coxI    GTTATTTACGTACAGAATTATATTCTTCTCTTCTTTAAGAATAATTGCACAAGAAAATGTT
Pv37coxI    GTTATTTACGTACAGAATTATATTCTTCTCTTCTTTAAGAATAATTGCACAAGAAAATGTT
Po35coxI    GTTATTTACGTACAGAATTATATTCTTCTCTTCTTTAAGAATAATTGCACAAGAAAATGTT
Pm58coxI    GTTATTTACGTACAGAATTATATTCTTCTCTTCTTTAAGAATAATTGCACAAGAAAATGCT
```

FIGURE 10 (CONT. II)

```
          241                                                          300
PfcoxI    AATCTATATAATATGATATATTTACAATTCACGGAATAATTATGATTTTTTCAATATAATG
Pf47coxI  AATCTATATAATATGATATATTTACAATTCACGGAATAATTATGATTTTTTCAATATAATG
Pv15coxI  AACTTATATAATATGATATATTTACATTACATTACATGGAATAATTATGATATTCTTAATATAATG
Pv16coxI  AACTTATATAATATGATATATTTACATTACATTACATGGAATTATTATGATATTCTTAATATAATG
Pv32coxI  AACTTATATAATATGATATATTTACATTACATTACATGGAATTATTATGATATTCTTAATATAATG
Pv37coxI  AACTTATATAATATGATATATTTACATTACATTACATGGAATTATTATGATATTCTTAATATAATG
Po35coxI  AACTTATATAATATGATATATTTACATTACATTACATGGAATTATTATGATATTCTTAATATAATG
Pm58coxI  AACTTATATAATATGATATATTTACATTACATTACATGGAATTATTATGATATTCTTAATATAATG 301                                                          360
PfcoxI    CCAGGATTATTCGGAGGATTTGGTAATTACTTTCTACCTATTTTATGTGGATCTCCAGAA
Pf47coxI  CCAGGATTATTCGGAGGATTTGGTAATTACTTTCTACCTATTTTATGTGGATCTCCAGAA
Pv15coxI  CCAGGATTATTCGGAGGATTTGGTAATTACTTCGTACCTATTTCCTACCAATTTTATGTGGTTCTCCAGAA
Pv16coxI  CCAGGATTATTCGGAGGATTCGGTAATTACTTCCTACCAATTTTATGTGGTTCTCCAGAA
Pv32coxI  CCAGGATTATTCGGAGGATTCGGTAATTACTTCCTACCAATTTTATGTGGTTCTCCAGAA
Pv37coxI  CCAGGATTATTCGGAGGATTCGGTAATTACTTCCTACCAATTTTATGTGGTTCTCCAGAA
Po35coxI  CCAGGATTATTCGGAGGATTCGGTAATTACTTCCTACCAATTTTATGTGGTTCTCCAGAA
Pm58coxI  CCAGGATTATTCGGAGGATTCGGTAATTACTTCCTACCAATTTTATGTGGTTCTCCAGAA
```

FIGURE 10 (CONT. III)

```
        361                                                         420
PfcoxI  TTAGCATATCCTAGAATTAATAGTATATCTTTACTGTTACAACCAATTGCTTTGTTTTA
Pf47coxI TTAGCATATCCTAGAATTAATAGTATATCTTTACTGTTACAACCAATTGCTTTGTTTTA
Pv15coxI CTTGCATATCCAAGAATTAATAGTATATCTTTATTATTACAACCAATAGCTTTATATTA
Pv16coxI CTTGCATATCCAAGAATTAATAGTATATCTTTATTATTACAACCAATAGCTTTATATTA
Pv32coxI CTTGCATATCCAAGAATTAATAGTATATCTTTATTATTACAACCAATAGCTTTATATTA
Pv37coxI CTTGCATATCCAAGAATTAATAGTATATCTTTATTATTACAACCAATAGCTTTATATTA
Po35coxI CTTGCATATCCAAGAATTAATAGTATATCTTTTATTATTACAACCAATAGCTTTATATTA
Pm58coxI CTTGCATATCCAAGAATTAATAGTATATCTTTATTATTACAACCAATAGCTTTATATTA 421                                                         480
PfcoxI  GTTATATTATCTACTGCAGCAGAATTTGGTGGTGGTGAACTGGATGGACTTTATATCCACCA
Pf47coxI GTTATATTATCTACTGCAGCAGAATTTGGTGGTGGTGAACTGGATGGACTTTATATCCACCA
Pv15coxI GTCATTTATCTACAGCAGCAGCAGAATTTGGAGGAGGTACTGGATGGACTTTATATCCACCA
Pv16coxI GTCATTTATCTACAGCAGCAGCAGAATTTGGAGGAGGTACTGGATGGACTTTATATCCACCA
Pv32coxI GTAATTTATCTACAGCAGCAGCAGAATTTGGAGGAGGTACTGGATGGACTTTATATCCACCA
Pv37coxI GTCATTTATCTACAGCAGCAGCAGAATTTGGAGGAGGTACTGGATGGACTTTATATCCACCA
Po35coxI GTCATTTATCTACAGCAGCAGCAGAATTTGGAGGAGGTACTGGATGGACTTTATATCCACCA
Pm58coxI GTCATTTATCTACAGCAGCAGCAGAATTTGGAGGAGGTACTGGATGGACTTTATATCCACCA
```

FIGURE 10 (CONT. IV)

| | 481 | 540 |
|---|---|---|
| PfcoxI | TTAAGTACACATCTTTAAATGTCATTATATCTCCCTGTAGCTGTAGATGTAATAATTTTGTTTA | |
| Pf47coxI | TTAAGTACACATCTTTAAATGTCATTATATCTCCCTGTAGCTGTAGATGTAATAATTTTGTTTA | |
| Pv15coxI | TTAAGTACATCACTTATGTCTTTATCTCCCTGTTGCAGTAGATGTTATCATTGTTGGTCTT | |
| Pv16coxI | TTAAGTACATCACTTATGTCTTTATCTCCCTGTTGCAGTAGATGTTATCATTGTTGGTCTT | |
| Pv32coxI | TTAAGTACATCACTTATGTCTTTATCTCCCTGTTGCAGTAGATGTTATCATTGTTGGTCTT | |
| Pv37coxI | TTAAGTACATCACTTATGTCTTTATCTCCCTGTTGCAGTAGATGTTATCATTGTTGGTCTT | |
| Po35coxI | TTAAGTACATCACTTATGTCTTTATCTCCTGTTGCAGTAGATGTTATCATTGTTGGTCTT | |
| Pm58coxI | TTAAGTACATCACTTATGTCTTTATCTCCTGTTGCAGTAGATGTTATCATTGTTGGTCTT | |

| | 541 | 600 |
|---|---|---|
| PfcoxI | TTAGTATCTGGAGTCGCTAGTATTATTGTCTTCATTAAATTTATTACTACAGTAATGCAT | |
| Pf47coxI | TTAGTATCTGGAGTCGCTAGTATTATTGTCTTCATTAAATTTATTACTACAGTAATGCAT | |
| Pv15coxI | TTAGTATCTGGTATTGCTAGTATTATTGTCTTCTTCTTTAAATTTATTACTACTGTAATGCAT | |
| Pv16coxI | TTAGTATCTGGTATTGCTAGTATTATTGTCTTCTTCTTTAAATTTATTACTACTGTAATGCAT | |
| Pv32coxI | TTAGTATCTGGTATTGCTAGTATTATTGTCTTCTTCTTTAAATTTATTACTACTGTAATGCAT | |
| Pv37coxI | TTAGTATCTGGTATTGCTAGTATTATTGTCTTCTTCTTTAAATTTATTACTACTGTAATGCAT | |
| Po35coxI | TTAGTATCTGGTATTGCTAGTATTATTGTCTTCTTCTTTAAATTTATTACTACTGTAATGCAT | |
| Pm58coxI | TTAGTATCTGGTATTGCTAGTATTATTGTCTTCTTCTTTAAATTTATTACTACTGTAATGCAT | |

FIGURE 10 (CONT. V)

```
         601                                                    660
PfcoxI   TTAAGAGCAAAAGGATTAACACTTGGTATATTAAGTGTTTCTACATGGTCATTGATCATT
Pf47coxI TTAAGAGCAAAAGGATTAACACTTGGTATATTAAGTGTTTCTACATGGTCATTGATCATT
Pv15coxI CTAAGATCTAAAGGTTAACACTTGGTATATTAAGTGTATCTACATGGTCATTAATAATT
Pv16coxI CTAAGATCTAAAGGTTAACACTTGGTATATTAAGTGTATCTACATGGTCATTAATAATT
Pv32coxI CTAAGATCTAAAGGTTAACACTTGGTATATTAAGTGTATCTACATGGTCATTAATAATT
Pv37coxI CTAAGATCTAAAGGTTTAACACTTGGTATATTAAGTGTATCTACATGGTCATTAATAATT
Po35coxI CTAAGATCTAAAGGTTTAACACTTGGTATATTAAGTGTATCTACATGGTCATTAATAATT
Pm58coxI CTAAGATCTAAAGGTTTAACACTTGGTATATTAAGTGTATCTACATGGTCATTAATAATT 661                                                    720
PfcoxI   ACATCAGGAATGTTATTGCTAACACTACCGGTTTTAACTGGAGGAGTATTAATGTTATTA
Pf47coxI ACATCAGGAATGTTATTGCTAACACTACCGGTTTTAACTGGAGGAGTATTAATGTTATTA
Pv15coxI ACATCTGTAATGCTATTATTAACATTACCTGTTGTTTTAACAGGTGGTGTTTAATGTTATTA
Pv16coxI ACATCTGTAATGCTATTATTAACATTACCTGTTGTTTTAACAGGTGGTGTTTAATGTTATTA
Pv32coxI ACATCTGTAATGCTATTATTAACATTACCTGTTGTTTTAACAGGTGGTGTTTAATGTTATTA
Pv37coxI ACATCTGTAATGCTATTATTAACATTACCTGTTGTTTTAACAGGTGGTGTTTAATGTTATTA
Po35coxI ACATCTGTAATGCTATTATTAACATTACCTGTTGTTTTAACAGGTGGTGTTTAATGTTATTA
Pm58coxI ACATCTGTAATGCTATTATTAACATTACCTGTTGTTTTAACAGGTGGTGTTTAATGTTATTA
```

FIGURE 10 (CONT. VI)

```
              721                                                           780
PfcoxI        TCAGACTTACATTTAATACTTTATTTTTTGACCCAACATTGCAGGAGATCCAATATTA
Pf47coxI      TCAGACTTACATTTAATACTTTATTTTTTGACCCAACATTGCAGGAGATCCAATATTA
Pv15coxI      TCAGATTTACATTTAATACATTATTTTTTGATCCTACATTGCTGGAGATCCTATTTTA
Pv16coxI      TCAGATTTACATTTAATACATTATTTTTTGATCCTACATTGCTGGAGATCCTATTTTA
Pv32coxI      TCAGATTTACATTTAATACATTATTTTTTGATCCTACATTGCTGGAGATCCTATTTTA
Pv37coxI      TCAGATTTACATTTAATACATTATTTTTTGATCCTACATTGCTGGAGACCCTATTTTA
Po35coxI      TCAGATTTACATTTAATACATTATTTTTTGATCCTACATTGCTGGAGATCCTATTTTA
Pm58coxI      TCAGATTTACATTTAATACATTTTAATCTTTTGATCCTACATTGCTGGAGATCCTATTTTA 781                                                           840
PfcoxI        TATCAACATTATTCTGGTTTTTTGGACATCCTGAAGTATACATTTAATATTACCTGCT
Pf47coxI      TATCAACATTATTCTGGTTTTTTGGACATCCTGAAGTATACATTTAATATTACCTGCT
Pv15coxI      TATCAACATCTATTTGGTTTTTGGACATCCTGAAGTGTATATTTAATATTACCAGCA
Pv16coxI      TATCAACATCTATTTGGTTTTTGGACATCCTGAAGTGTATATTTAATATTACCAGCA
Pv32coxI      TATCAACATCTATTTGGTTTTTGGACATCCTGAAGTGTATATTTAATATTACCAGCA
Pv37coxI      TATCAACATCTATTTGGTTTTTGGACATCCTGAAGTGTATATTTAATATTACCAGCA
Po35coxI      TATCAACATCTATTTGGTTTTTGGACATCCTGAAGTGTATATTTAATATTACCAGCA
Pm58coxI      TATCAACATCTATTTGGTTTTTGGACATCCTGAAGTGTATATTTAATATTACCAGCA
```

FIGURE 10 (CONT. VII)

```
        841                                                             900
PfcoxI   TTTGGAGTAATTAGTCATGTAATTTCTACTAATTATTGCAGAAATCTATTTGGTAATCAA
Pf47coxI TTTGGAGTAATTAGTCATGTAATTTCTACTAATTATTGCAGAAATCTATTTGGTAATCAA
Pv15coxI TTTGGTGTTATTAGTCATGTAATATCTACAAATTATTGTAGAAGTTTATTTGGTAATCAA
Pv16coxI TTTGGTGTTATTAGTCATGTAATATCTACAAATTATTGTAGAAGTTTATTTGGTAATCAA
Pv32coxI TTTGGTGTTATTAGTCATGTAATATCTACAAATTATTGTAGAAGTTTATTTGGTAATCAA
Pv37coxI TTTGGTGTTATTAGTCATGTAATATCTACAAATTATTGTAGAAGTTTATTTGGTAATCAA
Po35coxI TTTGGTGTTATTAGTCATGTAATATCTACAAATTATTGTAGAAGTTTATTTGGTAATCAA
Pm58coxI TTTGGTGTTATTAGTCATGTAATATCTACAAATTATTGTAGAAGTTTATTTGGTAATCAA 901                                                             960
PfcoxI   TCTATGATACTTGCTATGGGATGTATAGCTGTGTTTTAGGAAGCTTAGTATGGGTACATCAT
Pf47coxI TCTATGATACTTGCTATGGGATGTATAGCTGTGTTTTAGGAAGCTTAGTATGGGTACATCAT
Pv15coxI TCTATGATTTTAGCAATGAGTTGTATTGCTATATTAGGAAGTGTTGTATGGGCTCATCAT
Pv16coxI TCTATGATTTTAGCAATGAGTTGTATTGCTATATTAGGAAGTGTTGTATGGGCTCATCAT
Pv32coxI TCTATGATTTTAGCAATGAGTTGTATTGCTATATTAGGAAGTGTTGTATGGGCTCATCAT
Pv37coxI TCTATGATTTTAGCAATGAGTTGTATTGCTATATTAGGAAGTGTTGTATGGGCTCATCAT
Po35coxI TCTATGATTTTAGCAATGAGTTGTATTGCTATATTAGGAAGTGTTGTATGGGCTCATCAT
Pm58coxI TCTATGATTTTAGCAATGAGTTGTATTGCTATATTAGGAAGTGTTGTATGGGCTCATCAT
```

FIGURE 10 (CONT. VIII)

```
                961                                                          1020
PfcoxI     ATGTACACTACTGGTTTAGAAGTTGATACTAGAGCTTATTTTACTTCGACTACCATTTTA
Pf47coxI   ATGTACACTACTGGTTTAGAAGTTGATACTAGAGCTTATTTTACTTCGACTACCATTTTA
Pv15coxI   ATGTATACTACAGGTTTAGAAGTTAGAACAAGAGCATTTTTTACATCTACAACTATATTA
Pv16coxI   ATGTATACTACAGGTTTAGAAGTAGATACAAGAGCATTTTTTACATCTACAACTATATTA
Pv32coxI   ATGTATACTACAGGTTTAGAAGTAGATACAAGAGCATTTTTTACATCTACAACTATATTA
Pv37coxI   ATGTATACTACAGGTTTAGAAGTAGATACAAGAGCATTTTTTACATCTACAACTATATTA
Po35coxI   ATGTATACTACAGGTTTAGAAGTAGATACAAGAGCATTTTTTACATCTACAACTATATTA
Pm58coxI   ATGTATACTACAGGTTTAGAAGTAGATACAAGAGCATTTTTTACATCTACAACTATATTA 1021                                                          1080
PfcoxI     ATATCAATACCTACCGGTACAAAGTATTTAACTGGATATGTACATATATGAGTAGTAAT
Pf47coxI   ATATCAATACCTACCGGTACAAAGTATTTAACTGGATATGTACATATATGAGTAGTAAT
Pv15coxI   ATATCTATACCTACTGGAACAAAAATATTTAATTGGATATGTACATATATGAGTAGTAAT
Pv16coxI   ATATCTATACCTACTGGAACAAAATATTTAATTGGATATGTACACATATGGGTAGTAAT
Pv32coxI   ATATCTATACCTACTGGAACAAAATATTTAATTGGATATGTACATATATGGGTAGTAAT
Pv37coxI   ATATCTATACCTACTGGAACAAAATATTTAATTGGATATGTACATATATGGGTAGTAAT
Po35coxI   ATATCTATACCTACTGGAACAAAAATATTTAATTGGATATGTACATATATGGGTAGTAAT
Pm58coxI   ATATCTATACCTACTGGAACAAAAATATTTAATTGGATATGTACATATATGGGTAGTAAT
```

FIGURE 10 (CONT. IX)

```
            1081                                                        1140
PfcoxI      TTTGGTATGATACACAGCTCTTCATTATTGTCATTATTTATATTGTACATTTACATTT
Pf47coxI    TTTGGTATGATACACAGCTCTTCATTATTGTCATTATTATTTATATGTACATTTACATTT
Pv15coxI    TTTGGTATAACTCATAGTTCATCTTTATTATCATTACTATTTATATGTACATTTACTTTT
Pv16coxI    TTTGGTATAACTCATAGTTCATCTTTATTATCATTACTATTTATATGTACATTTACTTTT
Pv32coxI    TTTGGTATAACTCATAGTTCATCTTTATCATTATCATTACTATTTATATGTACATTTACTTTT
Pv37coxI    TTTGGTATAACTCATAGTTCATCTTTATTATCATTACTATTTATATGTACATTTACTTTT
Po35coxI    TTTGGTATAACTCATAGTTCATCTTTATTATCATTACTATTTATATGTACATTTACTTTT
Pm58coxI    TTTGGTATAACTCATAGTTCATCTTTATTATCATTACTATTTATATGTACATTTACTTTT 1141                                                        1200
PfcoxI      GGAGGTACTACTGGAGTTATATTAGGTAATGCTGCCATTGATGTAGCATTACATGACACA
Pf47coxI    GGAGGTACTACTGGAGTTATATTAGGTAATGCTGCCATTGATGTAGCATTACATGACACA
Pv15coxI    GGTGGTACTACAGGAGTTATATTAGGTAATGCAGCTATTGATATTGCATTACATGATACT
Pv16coxI    GGTGGTACTACAGGAGTAATATTAGGTAATGCAGCTATTGATATTGCATTACATGATACT
Pv32coxI    GGTGGTACTACAGGAGTAATATTAGGTAATGCAGCTATTGATATTGCATTACATGATACT
Pv37coxI    GGTGGTACTACAGGAGTAATATTAGGTAATGCAGCTATTGATATTGCATTACATGATACT
Po35coxI    GGTGGTACTACAGGAGTAATATTAGGTAATGCAGCTATTGATATTGCATTACATGATACT
Pm58coxI    GGTGGTACTACAGGAGTAATATTAGGTAATGCAGCTATTGATATTGCATTACATGATACT
```

FIGURE 10 (CONT. X)

```
        1201                                                      1260
PfcoxI  TATTATGTTATTGCTCATTTGTACTATCAATTGGTGCAATTATTGGATTATTT
Pf47coxI TATTATGTTATTGCTCATTTGTACTATCAATTGGTGCAATTATTGGATTATTT
Pv15coxI TACTATGTAATCGCTCATTTGTATTATCTATAGGTGCAATTATTGCATTGTTT
Pv16coxI TACTATGTAATCGCTCATTTGTATTATCTATAGGTGCAATTATTGCATTGTTT
Pv32coxI TACTATGTAATCGCTCATTTGTATTATCTATAGGTGCAATTATTGCATTGTTT
Pv37coxI TACTATGTAATCGCTCATTTGTATTATCTATAGGTGCAATTATTGCATTGTTT
Po35coxI TACTATGTAATCGCTCATTTCCATTTGTATTATCTATAGGTGCAATAATTGCATTGTTT
Pm58coxI TACTATGTAATCGCTCATTTCCATTTGTATTATCTATAGGTGCAATTATTGCATTGTTT 1261                                                      1320
PfcoxI  ACAACTGTAAGTGCATTTCAAGATAATTTCTTTGGTAAAAACTTACGTGAAAATTCTATT
Pf47coxI ACAACTGTAAGTGCATTTCAAGATAATTTCTTTGGTAAAAACTTACGTGAAAATTCTATT
Pv15coxI ACATTAGTAAGTAGTTTTCAAGAAAAACTTTTTTGGTAAACATTTACGTGAAAATTCTATA
Pv16coxI ACATTAGTAAGTAGTTTTCAAGAAAAACTTTTTTGGTAAACATTTACGTGAAAATTCTATA
Pv32coxI ACATTAGTAAGTAGTTTTCAAGAAAAACTTTTTTGGTAAACATTTACGTGAAAATTCTATA
Pv37coxI ACATTAGTAAGTAGTTTTCAAGAAAAACTTTTTTGGTAAACATTTACGTGAAAATTCTATA
Po35coxI ACATTAGTAAGTAGTTTTCAAGAAAAACTTTTTTGGTAAACATTTACGTGAAAATTCTATA
Pm58coxI ACATTAGTAAGTAGTTTTCAAGAAAAACTTTTTTGGTAAACATTTACGTGAAAATTCTATA
```

FIGURE 10 (CONT. XI)

```
        1321                                                           1380
PfcoxI  GTAATACTATGGTCAATGTTATTTTTTGTAGGTGTAATATTAACATTTTTACCTATGCAT
Pf47coxI GTAATACTATGGTCAATGTTATTTTTTGTAGGTGTAATATTAACATTTTTACCTATGCAT
Pv15coxI ATAATATTATGGTCAATCTTATTTTTATTGGAGTTGTATTAACATTCTTACCTATGCAT
Pv16coxI ATAATATTATGGTCAATCTTATTTTTATTGGAGTTGTATTAACATTCTTACCTATGCAT
Pv32coxI ATAATATTATGGTCAATCTTATTTTTATTGGAGTTGTATTAACATTCTTACCTATGCAT
Pv37coxI ATAATATTATGGTCAATCTTATTTTTATTGGAGTTGTATTAACATTCTTACCTATGCAT
Po35coxI ATAATATTATGGTCAATCTTATTTTTATTGGAGTTGTATTAACATTCTTACCTATGCAT
Pm58coxI ATAATATTATGGTCAATCTTATTTTTATTGGAGTTGTATTAACATTCTTACCTATGCAT 1381                                                           1440
PfcoxI  TTTTTAGGATTTAATGTAATGCCTAGACGTATTCCTGATTATCCAGACGCTTTAAATGGA
Pf47coxI TTTTTAGGATTTAATGTAATGCCTAGACGTATTCCTGATTATCCAGACGCTTTAAATGGA
Pv15coxI TTTCTTGGATTTAATGTAATGCCTAGACGTATTCCTGATTATCCAGACGCTTTAAATGGA
Pv16coxI TTTCTTGGATTTAATGTAATGCCTAGACGTATTCCTGATTATCCAGACGCTTTAAATGGA
Pv32coxI TTTCTTGGATTTAATGTAATGCCTAGACGTATTCCTGATTATCCAGACGCTTTAAATGGA
Pv37coxI TTTCTTGGATTTAATGTAATGCCTAGACGTATTCCTGATTATCCAGACGCTTTAAATGGA
Po35coxI TTCCTTGGATTTAATGTAATGCCTAGACGTATTCCTGATTATCCAGACGCTTTAAATGGA
Pm58coxI TTCCTTGGATTTAATGTAATGCCTAGACGTATTCCTGAT.....................
```

FIGURE 10 (CONT. XII)

```
          1441                                                      1500
PfcoxI    TGGAATATGATTGTTCTATTGGGTCAACAATGACTTTATTGGTTTACTAATTTTAAA
Pf47coxI  TGGAATATGATTGTTCTATTGGGTCAACAATGACTTTATTGGTTTACTAATTTTAAA
Pv15coxI  TGGAATATGATTGTTGTTCAATGGATCAACAATGACTTTATTGGTTTATTTATTTTAAAA
Pv16coxI  TGGAATATGATTGTTGTTCAATGGATCAACAATGACTTTATTGGTTTATTTATTTTAAAA
Pv32coxI  TGGAATATGATTGTTGTTCAATGGATCAACAATGACTTTATTGGTTTATTTATTTTAAA
Pv37coxI  TGGAATATGATTGTTGTTCAATGGATCAACAATGACTTTATTGGTTTATTTATTTTAAA
Po35coxI  TGGAATATGATTGTTGTTCAATGGATCAACAATGACTTTATTGGTTTATTTATTTTAAA
Pm58coxI  ..........................................................

1501                                                      1560
PfcoxI    TAATATTAC.TATTTATTGTTTTTATGAACTTTTACTTCTATTAATTAGTTAAAGCACAC
Pf47coxI  TAATATTAC.TATTTATTGTTTTTATGAACTTTTACTTCTATTAATTAGTTAAAGCACAC
Pv15coxI  TAATATAAAATATTTTTGTTTTTATGAATTATTCTATTAATTTAGCAAAAGCACAT
Pv16coxI  TAATATAAAATATTTTTGTTTTTATGAATTATTCTATTAATTTAGCAAAAGCACAT
Pv32coxI  TAATATAAAATATTTTTGTTTTTATGAATTATTCTATTAATTTAGCAAAAGCACAT
Pv37coxI  TAATATAAAATATTTTTGTTTTTATGAATTATTCTATTAATTTAGCAAAAGCACAT
Po35coxI  TAATATAAAATATTTTTGTTTTTATGAATTATTCTATTAATTTAGCAAAAGCACAT
Pm58coxI  ..........................................................
```

FIGURE 10 (CONT. XIII)

```
              1561                      1584
Pfcoxi        TTAATAAATTACCCATGTCCATTG  ....
Pf47coxI      TTAATAAATTACCCATGTCCATTA  ....
Pv15coxI      TTATTAAATTACCCATGTCCATTA  ....
Pv16coxI      TTATTAAATTACCCATGTCCATTA  ....
Pv32coxI      TTATTAAATTACCCATGTCCATTA  ....
Pv37coxI      TTATTAAATTACCCATGTCCATTA  ....
Po35coxI      TTATTAAATTACCCATGTCCATTA  ....
Pm58coxI      TTATTAAATTACCCATGTCCATTA  ....
```

FIGURE 10 (CONT. XIV)

DIAGNOSIS OF PARASITES

CROSS-REFERENCE TO RELATED APPLICATIONS

This application is a continuation of U.S. application Ser. No. 09/369,992 filed Aug. 6, 1999 now abandoned, which in turn claims priority from International Application PCT/IB98/00212, filed Feb. 5, 1998, which designates the United States and which claims priority from Australian Patent Application PO9481/97, filed Sep. 26, 1997, Australian Patent Application PO6329/97, filed Apr. 21, 1997, and Australian Patent Application PO4953/97, filed Feb. 6, 1997, all of which are incorporated by reference in their entirety.

FIELD OF THE INVENTION

The present invention relates generally to novel genetic sequences isolated from a parasitic protozoa which infects humans and other animals and the uses of said sequences as diagnostic agents for the detection of said protozoa in a biological sample. In particular, the present invention provides genetic sequences of the extrachromosomal genetic elements of the malaria agents *Plasmodium berghei*, *Plasmodium vivax*, *Plasmodium ovale*, *Plasmodium falciparum* and *Plasmodium malariae* and synthetic oligonucleotide derivatives, homologues, analogues and fragments thereof. The genetic sequences of the present invention are particularly useful in the diagnosis, prophylactic treatment and therapeutic treatment of humans and other animals which are capable of being infected by or are actually infected by protozoa such as *Plasmodium* ssp., for example *P. falciparum, P. vivax, P. malariae, P. ovale, P. cynomolgi, P. gonderi, P. (Hepatocytis) kochi, P. inui, P. knowlesi, P. reichenowi, P. rodhaini, P. schwetzi, P. cathemerium, P. elongatum, P. relictum, P. lophurae, P. gallinaceum, P. chabaudi, P. yoelii,* or *P. berghei*, amongst others. The invention provides further, a novel, reliable diagnostic assay for the detection of *Plasmodium* ssp. in humans and animals.

Bibliographic details of the publications referred to by author in this specification are collected at the end of the description. Sequence identity numbers (SEQ ID Nos.) for the nucleotide and amino acid sequences referred to in the specification are defined after the bibliography.

Throughout the specification, unless the context requires otherwise, the word "comprise", or variations such as "comprises" or "comprising", will be understood to imply the inclusion of a stated element or integer or group of elements or integers, but not the exclusion of any other element or integer or group of elements or integers.

BACKGROUND TO THE INVENTION

More than fifty different species of *Plasmodium* can cause malaria in humans, monkeys, birds, fish, cattle and rodents. The development of diagnostic assays for the detection of *Plasmodium* in humans and animals is therefore highly desirable.

Human malaria, which is caused by *Plasmodium* ssp., in particular *P. falciparum, P. vivax, P. malariae,* and *P. ovale*, remains one of the major health problems around the world.

*Plasmodium vivax* induces a moderate form of malaria, *vivax* malaria, characterized by periodic chills and fever, an enlarged spleen, anaemia, severe abdominal pain and headaches, and extreme lethargy. If left untreated, the disease tends to be self-limiting within a period of 10 to 30 days, but will recur periodically. Although the fatality rate of *vivax* malaria is low, the disease is highly debilitating and makes the patient more vulnerable to other diseases.

The incubation period ranges from 10 days to 4 weeks. Generally, paroxysms of chills and fever appear on the 14th day after the bite of an infected female anopheles mosquito. During this time the parasite has been multiplying in the liver cells of the patient. Paroxysms continue to recur every other day, as the parasite completes its 48-hour cycle of development, now in the blood. During the paroxysm, the patient first goes through a "cold stage" during which he has chilly sensations, his skin is blue, his teeth chatter and there is violent shaking. After an hour, the "hot stage" is ushered in, with a rise in temperature to as high as 107° F. (41.7° C.); the skin is hot and dry and the patient complains of severe headache. The fever lasts about 2 hours, and is followed by the "sweating stage", during which there is profuse perspiration, the temperature falls to normal, the headache disappears, and although weak and drowsy, the patient feels well.

*Plasmodium ovale* produces a disease very similar to *vivax* malaria.

*Plasmodium malariae*, the causative agent of quartan malaria, has an incubation period of 18-40 days. The paroxysms occur every 72 hours, and are longer and somewhat more severe than those accompanying *vivax* malaria.

*Plasmodium falciparum*-induced malaria (*falciparum* malaria) presents oedema of the brain and lungs and blockage of the kidneys, in addition to the symptoms associated with *vivax* malaria. Unless treated promptly, the fatality rate of *falciparum* malaria is high, especially in juveniles.

Paroxysms associated with *falciparum* malaria occur irregularly after a 12-day incubation period. They are severe, and accompanied by high temperatures. The so-called cerebral algid, haemorrhagic and pernicious types of malaria represent forms of *falciparum* malaria with different localizations of the parasite. In the cerebral type, the onset is delirium and coma, and death may occur in several hours without return to consciousness. "Black-water fever" or haemorrhagic malaria is a type in which haemolysis or dissolution of the red cells occurs, and dark urine due to the presence of haemoglobin is an outstanding feature. In the algid form, there are vomiting, diarrhea, and subnormal temperature.

The life cycle of the parasite and its course in the human body proceeds in the following way. The saliva of the mosquito contains the *Plasmodium* at the lance-shaped sporozoite stage of its life cycle. Upon inoculation of the host by biting, the sporozoites quickly migrate to the liver where they divide and develop into multi nucleated schizonts. Within 6 to 12 days, the schizonts disrupt and release into the blood the form known as merozoites. Each liver cell infected by one sporozoite releases into the blood stream from 10,000 to 30,000 merozoites. These later invade the host□s erythrocytes where they grow and form more schizonts which, in turn, again divide, releasing more merozoites into the blood stream to repeat the cycle. The principal symptoms of malaria are associated with the rupture of the schizonts, the periodic lysis of the blood cells with release of merozoites and toxic wastes which cause the regular fevers and chills of malaria.

Neither vector control measures nor immuno or chemoprophylaxis have proven effective in eradicating the disease. Thus, more than ever, chemotherapy appears to be crucial in dealing with both the prevention and treatment of malaria. However, presently used drugs are constantly losing their efficacy due to the development of drug resistance by the parasite. For example, drug resistance of *Plasmodium fal-*

*ciparum* to chloroquine has occurred in Bangladesh, Brazil, Burma, Colombia, Ecuador, Guyana (French), Guyana, India, Indonesia, Kampuchea, Malaysia, Nepal, Pakistan, Panama, Philippines, Surinam, Thailand, Venezuela, and Vietnam, amongst others. Therefore, the design of novel drugs is urgent.

Targets for drug design are generally nuclear-encoded gene products. However, inter-specific and developmental variation in nuclear gene expression has reduced the general efficacy of drugs which target such nuclear-encoded gene products.

Diagnosis of malaria is generally made by microscopic examination of blood films taken during episodes of fever, when the parasites may be seen. In general, the *Plasmodium* parasite is detected microscopically by examining finger prick blood samples for the presence of the morphologically distinct parasite using Giemsa stain solution (Shute et al., 1980). This needs to be done by an experienced microscopist since *Plasmodium falciparum* and *Plasmodium vivax* are morphologically similar, albeit not identical. In view of the distinct epidemiologies of *P. falciparum* compared to *P. vivax*, it is important that diagnosis of infection by these species have a low error rate. Any incorrect diagnosis of *falciparum* malaria, for example, may be fatal for the patient. The microscopic technique is limited in so far as the method is slow and specialised personnel is required to perform the technique.

A variation of the standard microscopic assay, the quantitative buffy coat (QBC) technique is based upon the ability of parasite nucleoproteins to absorb acridine orange and fluoresce (Wardlaw et al, 1983). The fluorescent nucleoproteins are readily visible against a background of non-fluorescent red blood cells. Although the method is more sensitive than the standard microscopic assay, it suffers from the disadvantages associated with the standard microscopic assay. Furthermore, the requirement of costly fluorescence microscopes and centrifuges to perform the QBC assay, renders the method unrealistic in resource-limited settings which often lack even electricity.

Immunological tests, for example the ParaSight™ F test (Becton Dickinson) and the similar ICT Malaria P.f. test (ICT Diagnostics) detect the *Plasmodium falciparum* histidine-rich protein HRP2 in blood samples derived from patients. A major drawback associated with such methods is that they require *Plasmodium falciparum* gene expression to occur before the organism can be detected. Furthermore, as considerable variation in gene expression can occur between *Plasmodium* ssp., these tests tend to be species-specific. For example, the ParaSight™ F test (Becton Dickinson) and ICT Malaria P.f. test (ICT Diagnostics) are specific for *Plasmodium falciparum* only and incapable of detecting other species. Furthermore, these tests, in particular the ParaSight™ F test (Becton Dickinson), are subject to a high proportion of false-negative detections, such that a higher than acceptable frequency of patients infected with a *Plasmodium* ssp. go undetected.

Immunological techniques such as the enzyme-linked immunosorbent assay (ELISA) or the radio immunoassay (RIA) which detect genus- and species-specific parasite antigens also exist. However, such methods are constrained by immunological cross-reaction between parasite and host antigens on the one hand and between parasite antigens and antigens derived from other microorganisms on the other hand. As a consequence, the susceptibility of immunological methods to false positive detection of *Plasmodium* is high. As already mentioned above, species-specific detection methods lead to a large number of false-negative detections.

Furthermore, as different *Plasmodium* antigens are expressed at different developmental stages, immunological techniques may only detect the parasite at certain stages of development. Such antigenic diversity displayed by *Plasmodium* is a major obstacle to the application of immunological techniques. In addition, radioisotope-based assays such as the RIA are impractical for field use. Immunological methods cannot distinguish between past and present infections.

State-of-the art diagnostic assays, which rely on the detection of *Plasmodium* genomic DNA in a sample, are species-specific and not capable of general application for any *Plasmodium* ssp., in part because there is considerable variation in genomic DNA between *Plasmodium* species, such variation precluding the simultaneous detection of several *Plasmodium* ssp. in a single biological sample or alternatively, the use of a single DNA-based assay for the detection of any *Plasmodium* ssp. in a biological sample derived from a human or animal subject suspected of carrying the parasite.

As a consequence of the foregoing, there is a high demand for a reliable and simple technology for the diagnosis of *Plasmodium* in human and animal tissues.

*Plasmodium* ssp. possess additional genomes with potentially crucial functions (Wilson et al., 1991). Until the present invention, very little was known about this extrachromosomal material. Furthermore, the function of the extrachromosomal plastid element in the protozoans remains to be determined. To date, there is no clear evidence for DNA replication or functionally active gene products from the plastid element.

SUMMARY OF THE INVENTION

One aspect of the present invention provides a method of detecting a *Plasmodium* in a biological sample derived from a human or animal subject, said method comprising contacting a *Plasmodium* extrachromosomal genetic element or a fragment thereof with said sample or nucleic acid derived therefrom for a time and under conditions sufficient for hybridisation to occur and then detecting said hybridisation using a detection means. According to this aspect, the extrachromosomal genetic element or fragment thereof may comprises a mitochondrion or mitochondrion-like molecule or a genetic sequence derived therefrom or a homologue, analogue or derivative thereof, in particular a *Plasmodium* cytochrome C oxidase (coxl) genetic sequence derived from any one of *P. falciparum, P. berghei, P. vivax, P. ovale* or *P. malariae*, amongst others.

Alternatively, the extrachromosomal genetic element may comprise a plastid or plastid-like molecule or a genetic sequence derived therefrom or a homologue, analogue or derivative thereof, in particular a *Plasmodium* PS1-PL470, PLH-PPH, PRB or PWQ genetic sequence derived from *P. falciparum, P. berghei, P. vivax, P. ovale* or *P. malariae*, amongst others.

Preferably, the detection means comprises a nucleic acid hybridisation reaction or polymerase chain reaction or a modification thereof, essentially as described herein.

A further aspect of the invention provides for the use of said *Plasmodium* extrachromosomal genetic element or a homologue, analogue or derivative thereof to detect *Plasmodium* in a biological sample derived from a human or animal, for example a biological sample comprising blood or blood products, in particular dried blood.

A further aspect of the invention provides an isolated extrachromosomal genetic element primer or probe derived from *Plasmodium* ssp.

A further aspect of the invention provides a kit for the detection of *Plasmodium* ssp. in a biological sample, said kit comprising one or more isolated extrachromosomal genetic element probes or primers and one or more reaction buffers suitable for use in a nucleic acid hybridisation reaction or polymerase chain reaction.

BRIEF DESCRIPTION OF THE DRAWINGS

FIG. 9 is a copy of a schematic representation of the aligned LSU-rRNA sequences from different *Plasmodium* species obtained from various regions in Asia. The alignment was carried out using the Clustal Method in the DNASTAR programme. Sequences indicated are derived from several isolates of *P. falciparum* (Pf), i.e. Pf(C10), SEQ ID NO:23; Pf10/P, SEQ ID NO:24; Pf11/P, SEQ ID NO:25; Pf19/I, SEQ ID NO:26; Pf20/L, SEQ ID NO:27; and Pf18/S, SEQ ID NO:28, *P. vivax* (Pv), i.e. Pv12/P, SEQ ID NO:29; Pv13/P, SEQ ID NO:30; Pv15/I, SEQ ID NO:31; Pv16/L, SEQ ID NO:32; Pv17/S, SEQ ID NO:33; and Pv86/C, SEQ ID NO:34, *P. malariae* (Pm), i.e. Pm1/S, SEQ ID NO:35; and Pm38/S, SEQ ID NO:38, *P. Ovale* (Po), i.e. Po35/S, SEQ ID NO:37; and Po36/S, SEQ ID NO:38, and *P. berghei* (Pb), i.e. Pb(ANKA), SEQ ID NO:39. The alphanumeric designation following the *Plasmodium* species descriptor indicates the isolate number and geographical origin of the specimen, wherein P=Pakistan, I=India, L=Laos, C=Columbia and S=Singapore. The GenBank accession numbers for Pf(C10) (SEQ ID NO:23) and Pb(ANKA) (SEQ ID NO:39) are X95275 and U79731 respectively.

FIG. 10 is a schematic representation of the aligned cox I sequences from *P. falciparum* (Pf), i.e. Pfcoxl, SEQ ID NO:40; and Pf47coxl, SEQ ID NO:41, *P. vivax* (Pv), i.e. Pv15coxl, SEQ ID NO:42; Pv16coxl, SEQ ID NO:43; Pv32coxl, SEQ ID NO:44; and Pv37coxl, SEQ ID NO:45,

*P. malariae* (Pm), i.e. Pm58coxl, SEQ ID NO:47, and *P. Ovale* (Po), i.e. Po35coxl, SEQ ID NO:46, isolates. The numeric designation following the *Plasmodium* species descriptor indicates the isolate number. The GenBank accession number for the *P. falciparum* sequences is M76611.

Figure 11:
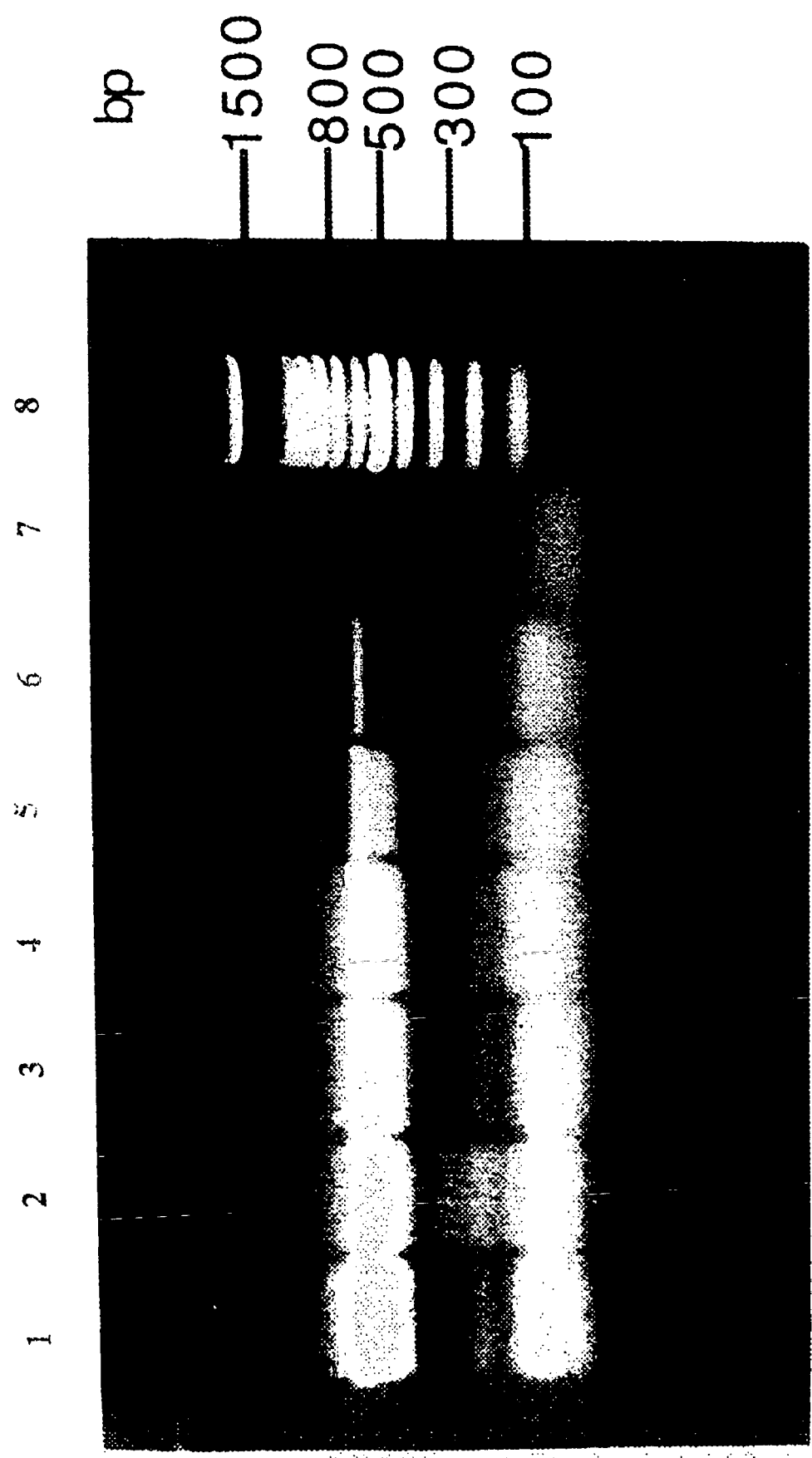

FIG. 11 is a copy of a photographic representation showing PCR amplification of blood spots. Each reaction uses 1 □l of blood containing different quantity of parasites. The amount of DNA used in each reaction, expressed as an equivalent number of parasites, is as follows: lane 1 contains 800 parasites; lane 2 contains 400 parasites; lane 3 contains 80 parasites; lane 4 contains 40 parasites; lane 5 contains 8 parasites; lane 6 contains 4 parasites; and lane 7 contains 0.8 parasites. Lane 8 contains the 100 bp DNA ladder (Promega) used as a marker. The detection limit is 4 parasites.

DETAILED DESCRIPTION OF THE PREFERRED EMBODIMENTS

In work leading up to the present invention, the inventors have discovered that the molecular composition, physical arrangements and nucleotide sequences of the extrachromosomal plastid-like element and mitochondrial element are highly conserved in different *Plasmodium* ssp.

The inventors have utilised the high degree of homology between different *Plasmodium* ssp. in the design of reliable, genera-specific or species-specific diagnostic assays for the detection of *Plasmodium*. The diagnostic assays described herein provide a significant advantage over currently employed assays based upon the detection of *Plasmodium* genomic DNA.

Furthermore, the inventors have discovered that the assays described herein provide the added advantage of excluding the high frequency of false negative detection of *Plasmodium* in a biological sample to a greater degree than known diagnostics.

The inventors further contemplate the use of polypeptides encoded by the extrachromosomal plastid-like element, and their homologues, analogues and derivatives, as targets for drug design and in the development of anti-malarial vaccines.

Accordingly, one aspect of the invention provides a diagnostic assay for the detection of *Plasmodium* in a biological sample derived from a human or animal subject, said assay comprising the detection of a *Plasmodium* extrachromosomal genetic element or a homologue, analogue or derivative thereof in said sample.

In an alternative embodiment, the invention provides a diagnostic assay for the detection of *Plasmodium* in a biological sample derived from a human or animal subject, said assay comprising the steps of hybridising a *Plasmodium* ssp. extrachromosomal genetic element probe or primer or a homologue, analogue or derivative thereof to said sample and then detecting said hybridisation using a detection means.

According to this aspect, the *Plasmodium* detected using the invention may be any species of *Plasmodium* which carries an extrachromosomal genetic element.

In a preferred embodiment, the *Plasmodium* being detected is selected from the list comprising *P. falciparum, P. vivax, P. malariae, P. ovale, P. cynomolgi, P. gonderi, P. (Hepatocytis) kochi, P. inui, P. knowlesi, P. reichenowi, P. rodhaini, P. schwetzi, P. cathemerium, P. elongatum, P. relictum, P. lophurae, P. gallinaceum, P. yoelii,* or *P. berghei*, amongst others.

In a more particularly preferred embodiment however, the present invention is useful for the detection of a *Plasmodium* in biological samples derived from humans and the *Plasmodium* in such cases is selected from the list comprising *P. falciparum, P. vivax, P. malariae* and *P. ovale*, amongst others.

The term "biological sample" as used herein shall be taken to refer to any organ, tissue, cell, exudate, nucleic acid, protein, nucleoprotein or other material which is derived from a living or once-living organism. Accordingly, biological samples may be mosquito or other vectors of *Plasmodium* ssp., human or animal tissue, blood or derivatives of blood and blood products, amongst others. A biological sample may be prepared in a suitable solution, for example an extraction buffer or suspension buffer. The present invention extends to the diagnosis of biological solutions thus prepared, the only requirement being that said solution at least comprises a biological sample as described herein.

The biological sample to be tested according to the invention, is derived from a human or animal species, in particular a human or animal which is capable of being infected by a *Plasmodium*. A particular advantage of the present invention is that it may be readily adapted to facilitate the analysis of any biological sample derived from a human or other animal. Those skilled in the relevant art will know how to modify the assay of the invention for the purposes of adapting said assay to the analysis of different biological tissues, where relevant or indicated, without any undue experimentation.

In a particularly preferred embodiment, the biological sample may be derived from the blood tissue of a human or animal subject, or cells, nucleic acid molecules and exudates derived therefrom, for example buffy coat, plasma, DNA or RNA, amongst others. The use of dried blood spots derived from human subjects as biological samples for the performance of the assays described herein is particularly contemplated by the invention.

The term "extrachromosomal genetic element" shall be taken to refer to any nucleic acid molecule, in particular DNA or RNA, which comprises a part of the complete genetic material of a *Plasmodium* ssp. but which does not comprise a part of a *Plasmodium* ssp. chromosome or a direct gene product thereof. An extrachromosomal genetic element of a *Plasmodium* ssp. may or may not replicate independently of the *Plasmodium* genome, such that the copy number of said genetic element may vary between *Plasmodium* cells.

Accordingly, a *Plasmodium* extrachromosomal genetic element as hereinbefore defined may be a linear or circular DNA molecule. In this regard, a linear DNA molecule may resemble, at the nucleotide sequence level at least, mitochondrial DNA (Suplick et al, 1988), while the circular DNA molecule in a *Plasmodium* resembles a vestigial plastid genome (Gardner et al, 1991; Howe et al, 1992).

The present inventors have shown herein that the malaria parasites harbour two extrachromosomal DNAs. One of these is a small 6 kb molecule which encodes three classical mitochondrial protein coding genes, attesting to its identity. The other is a circular molecule resembling the remnant of an algal plastid genome. The mitochondria DNA of *Plasmodium* species is very short; about 6 kb and codes for three proteins, namely cytochrome c oxidase subunits I (cox I) and III (cox III), and cytochrome b (cyt b) as well as fragments of ribosomal RNA genes.

In a preferred embodiment of the invention, the *Plasmodium* extrachromosomal genetic element is a plastid DNA molecule comprising approximately 30-35 kb of nucleotides in length.

In an alternative preferred embodiment, the *Plasmodium* extrachromosomal genetic element is mitochondrial DNA or mitochondrion-like DNA comprising approximately 6 kb in length.

In the present context, an extrachromosomal genetic element may comprise a complete organellar DNA molecule or a derivative thereof, for example a gene or an oligonucleotide which is suitable for use as a probe or primer molecule.

As used herein, the term "probe" refers to a nucleic acid molecule which is derived from a *Plasmodium* extrachromosomal genetic element and capable of being used in the detection thereof.

The term "primer" refers to a probe as hereinbefore defined which is further capable of being used to amplify a nucleotide sequence derived from a *Plasmodium* extrachromosomal genetic element in a polymerase chain reaction.

The diagnostic assay of the present invention is useful for the detection of a *Plasmodium* extrachromosomal genetic element or a *Plasmodium*-derived extrachromosomal genetic element, regardless of whether or not said genetic element expresses or is capable of expressing a polypeptide product.

The term "*Plasmodium*-derived" as used herein shall be taken to refer to an integer which, although it originates from a *Plasmodium* ssp. is not necessarily present in its natural state. For example, an extrachromosomal genetic element may be derived from a *Plasmodium* ssp. if it has been purified or partially purified and/or modified by digestion with restriction endonucleases or other DNA-modifying enzymes, to produce an analogue or derivative molecule.

The *Plasmodium* extrachromosomal genetic element probe or primer may be a mitochondrion or mitochondrion-like molecule or alternatively a plastid or plastid-like molecule, derived from a *Plasmodium* ssp. which is capable of infecting a human or animal subject.

In a particularly preferred embodiment, the extrachromosomal genetic element probe or primer or a homologue, analogue or derivative thereof, is derived from *Plasmodium berghei, P. ovale, P. malariae, P. falciparum, Plasmodium vivax, Plasmodium malariae, Plasmodium chabaudi, Plasmodium yoelii,* amongst others.

However, in a more particularly preferred embodiment of the invention, the extrachromosomal genetic element probe or primer is at least 95% identical to one or more of the sequences set forth in SEQ ID Nos: 1-22 or FIG. 9 or 10 or a complementary nucleotide sequence, or a homologue, analogue or derivative thereof.

Alternatively, the extrachromosomal genetic element probe or primer is capable of hybridising under high stringency conditions to one or more of the sequences set forth in SEQ ID NOS: 1-22 or to any one or more of the sequences set forth in FIG. 9 or 10 or a complementary nucleotide sequence or a homologue, analogue or derivative thereof.

In a further alternative embodiment, the *Plasmodium* ssp. extrachromosomal genetic element probe or primer used in the inventive method preferably comprises a sequence of nucleotides of at least 15 nucleotides, more preferably at least 25 nucleotides, even more preferably at least 50 nucleotides and even more preferably at least 100 nucleotides or 500 nucleotides derived from the sequence set forth in SEQ ID NOs:1-4 or to the *Plasmodium vivax, Plasmodium ovale, Plasmodium berghei, Plasmodium falciparum* or *Plasmodium malariae* sequences set forth in FIG. 9 or 10, or a complement thereof.

In a most particularly preferred embodiment, the extrachromosomal genetic element probe or primer comprises a nucleotide sequence set forth in any one or more of SEQ ID NOS: 1-22 or FIG. 9 or 10, or a complementary nucleotide sequence, or a homologue, analogue or derivative thereof.

For the purposes of nomenclature, the nucleotide sequences set forth in SEQ ID NOs:1-4 correspond to one strand of the PS1-PL470, PLH-PPH, PRB and PWQ genes, respectively, of the 30.7 kb *Plasmodium berghei* plastid. The inventors have shown that the extrachromosomal genetic element is transcriptionally-active, using reverse transcription polymerase chain reaction (RT-PCR), and encodes organelle-like rRNAs, tRNAs, ribosomal proteins and RNA polymerase subunits, amongst others.

The nucleotide sequences set forth in SEQ ID Nos: 5-10 and 19-20 correspond to synthetic oligonucleotide sequences derived from the *Plasmodium berghei* plastid.

The nucleotide sequences set forth in SEQ ID Nos: 11-14 and 22 correspond to synthetic oligonucleotide sequences derived from the *Plasmodium vivax* mitochondrial coxl gene, while the nucleotide sequences set forth in SEQ ID Nos: 11, 15-18 and 21 correspond to synthetic oligonucleotide sequences derived from the *P. falciparum* mitochondrial coxl gene.

The nucleotide sequences Pm1/S and Pm38/S in FIG. 9 relate to the plastid-like extrachromosomal genetic element in two *P. malariae* isolates and Po35/S and Po36/S relate to the extrachromosomal genetic element of two *P. ovale* isolates. The nucleotide sequences designated Pv12/P, Pv13/P, Pv15/I, Pv16/L, Pv17/S and Pv86C in FIG. 9 relate to plastid-like extrachromosomal genetic element sequences of different *P. vivax* isolates.

For the present purpose, "homologues" of a nucleotide sequence shall be taken to refer to an isolated nucleic acid molecule which is substantially the same as the nucleic acid molecule of the present invention or its complementary nucleotide sequence, notwithstanding the occurrence within said sequence, of one or more nucleotide substitutions, insertions, deletions, or rearrangements.

"Analogues" of a nucleotide sequence set forth herein shall be taken to refer to an isolated nucleic acid molecule which is substantially the same as a nucleic acid molecule of the present invention or its complementary nucleotide sequence, notwithstanding the occurrence of any non-nucleotide constituents not normally present in said isolated nucleic acid molecule, for example carbohydrates, radiochemicals including radio nucleotides, reporter molecules such as, but not limited to biotin, DIG, alkaline phosphatase or horseradish peroxidase, amongst others.

"Derivatives" of a nucleotide sequence set forth herein shall be taken to refer to any isolated nucleic acid molecule which contains significant sequence similarity to said sequence or a part thereof. Generally, the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intrasequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterised by the removal of one or more nucleotides from the nucleotide sequence. Substitutional nucleotide variants are those in which at least one nucleotide in the sequence has been removed and a different nucleotide or nucleotide analogue inserted in its place.

The present invention encompasses all such homologues, analogues or derivatives of a *Plasmodium* extrachromosomal genetic element, subject to the proviso that said homologues, analogues or derivatives are useful in the performance of at least one assay format as described herein.

According to this aspect of the invention, the *Plasmodium* extrachromosomal genetic element probe or primer may comprise inosine, adenine, guanine, thymidine, cytidine or uracil residues or functional analogues or derivatives thereof which are capable of being incorporated into a polynucleotide molecule, provided that the resulting probe or primer is capable of hybridising under at least low stringency conditions to a *Plasmodium* extrachromosomal genetic element.

The inventors have discovered that the extrachromosomal genetic element of *Plasmodium* is particularly useful as a marker of *Plasmodium* infection in a human or animal subject, because the detection of said element is not subject to the disadvantages of other assay methods, in particular the prevalence of false negative detection. As a consequence, fewer numbers of *Plasmodium*-infected hosts escape detection, by screening such hosts for the presence of the extrachromosomal genetic element according to the embodiments described herein (1% or less false negative detection compared to 3% or more for other methods), than by screening for the presence of other *Plasmodium*-expressed genes or by screening for the expression products of said genes.

Furthermore, the present invention is a procedure for assaying or identifying *Plasmodium* in a biological sample, preferably blood or a derivative of blood and in particular a biological sample which comprises dried blood.

The present invention clearly contemplates diagnostic assays which are capable of both genera-specific or species-specific detection. Accordingly, in one embodiment, the *Plasmodium* ssp. extrachromosomal genetic element probe or primer or a homologue, analogue or derivative thereof comprises DNA capable of being used to detect multiple *Plasmodium* ssp. In an alternative embodiment, the *Plasmodium* ssp. extrachromosomal genetic element probe or primer or a homologue, analogue or derivative thereof comprises DNA capable of being used to detect a particular *Plasmodium* ssp.

The inventors have discovered further that the coding region of a *Plasmodium* extrachromosomal genetic element is highly-conserved in different *Plasmodium* ssp., while there is much more variation at the nucleotide level in the non-coding regions. Whilst not being bound be any theory or mode of action, the more highly conserved sequences in the extrachromosomal genetic element derived from a particular species of *Plasmodium* are particularly useful as genera-specific probes and/or primers for the detection of any *Plasmodium*, while the less-conserved sequences of said element may be useful as species-specific probes and/or primers for the detection of a sub-group of *Plasmodium*, for example a sub-group which infects humans or primates as opposed to other animals, or which induces a specific form of malaria in humans.

The present inventors have also shown herein that certain sequences of the *Plasmodium* cytochrome c oxidase differ between species. Accordingly, a preferred embodiment of the present invention extends to the use of nucleotide sequences derived from the mitochondrial extrachromosomal genetic element of *Plasmodium*, more preferably derived from *P. falciparum* or *P. vivax* in the diagnosis of species-specific infections by one or more of *P. malariae, P. ovale, P. vivax* or *P. falciparum*, amongst others.

According to this embodiment, the nucleotide sequence set forth in SEQ ID NO:11 is a "universal probe" for the detection of at least *P. falciparum* and *P. vivax*, whilst SEQ ID Nos: 21 and 22 are species-specific probes for the detection of *P. falciparum* and *P. vivax*, respectively. Particularly preferred primer combinations for the species-specific detection of *P. falciparum* include, but are not limited to primers comprising SEQ ID Nos:7 and 8, SEQ ID Nos: 11 and 15, SEQ ID Nos: 11 and 16, SEQ ID Nos:11 and 17 SEQ ID Nos:16 and 18 and alternative combinations thereof readily determined by those skilled in the art. Particularly preferred primer combinations for the species-specific detection of *P. vivax* include, but are not limited to primers comprising SEQ ID Nos:11 and 12 and SEQ ID Nos:13 and 14 and alternative combinations thereof readily determined by those skilled in the art.

Furthermore, one or more of the diagnostic assays described herein may also be adapted to a genera-specific or species-specific assay by varying the stringency of the hybridisation step. Accordingly, a low or lower stringency hybridisation may be used to detect several different species of *Plasmodium* in one or more biological samples being assayed, while a high or higher stringency of hybridisation is used to detect the presence of a specific species of *Plasmodium*.

For the purposes of defining the level of stringency, a low stringency is defined herein as being a hybridisation and/or a wash carried out in 6×SSC buffer, 0.1% (w/v) SDS at 28° C. A moderate stringency is defined herein as being a hybridisation and/or wash carried out in 2×SSC buffer, 0.1% (w/v) SDS at a temperature in the range 45 □C to 65 □C. A high stringency is defined herein as being a hybridisation and/or wash carried out in 0.1×SSC buffer, 0.1% (w/v) SDS at a temperature of at least 65° C. Those skilled in the art will be aware of equivalent reaction conditions to those described herein for defining the hybridisation stringency.

Generally, the stringency is increased by reducing the concentration of SSC buffer, and/or increasing the concentration of SDS and/or increasing the temperature of the hybridisation and/or wash. Those skilled in the art will be aware that the conditions for hybridisation and/or wash may vary depending upon the nature of the hybridisation membrane or the type of hybridisation probe used. Conditions for hybridisations and washes are well understood by one normally skilled in the art. For the purposes of clarification of the parameters affecting hybridisation between nucleic acid molecules, reference is found in pages 2.10.8 to 2.10.16. of Ausubel et al. (1987), which is herein incorporated by reference.

The detection means according to this aspect of the invention may be any nucleic acid-based detection means, for example nucleic acid hybridisation techniques or paper chromatography hybridisation assay (PACHA) or an amplification reaction such as a polymerase chain reaction (PCR) or nucleic acid sequence-based amplification (NASBA) system. The invention further encompasses the use of different assay formats of said nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR) and reverse transcription polymerase chain reaction (RT-PCR), amongst others.

Wherein the detection means is a nucleic acid hybridisation technique, the *Plasmodium* extrachromosomal genetic element probe may be labelled with a reporter molecule capable of producing an identifiable signal (e.g. a radioisotope such as $^{32}$P or $^{35}$S or a biotinylated molecule). According to this embodiment, those skilled in the art will be aware that the detection of said reporter molecule provides for identification of the *Plasmodium* extrachromosomal genetic element probe and that, following the hybridisation reaction, the detection of the corresponding *Plasmodium* ssp. extrachromosomal genetic element in the biological sample is facilitated. Those skilled in the art will recognise that additional probes may be used to confirm the assay results obtained using a single probe.

A variation of the nucleic acid hybridisation technique contemplated by the present invention is the paper chromatography hybridisation assay (PACHA) described by Reinhartz et al. (1993) and equivalents thereof, wherein a target nucleic acid is labelled with a reporter molecule such as biotin, applied to one end of a nitrocellulose or nylon membrane filter strip and subjected to chromatography under the action of capillary or other forces (eg. an electric field) for a time and under conditions sufficient to promote migration of said target nucleic acid along the length of said membrane to a zone at which a *Plasmodium* extrachromosomal genetic element DNA probe is immobilised thereto, for example in the middle region. According to this detection format, labelled target nucleic acid comprising a *Plasmodium* extrachromosomal genetic element which is complementary to the probe will hybridise thereto and become immobilised in that region of the membrane to which the probe is bound. Non-complementary sequences to the probe will diffuse past the site at which the probe is bound. Those skilled in the art will be aware that the target nucleic acid may comprise a crude or partially-pure extract of *Plasmodium* DNA or RNA or alternatively, comprise amplified DNA or purified *Plasmodium* extrachromosomal genetic element DNA. Additional variations of this detection means which utilise the nucleotide sequences described herein are clearly encompassed by the present invention.

Wherein the detection means is an RFLP, nucleic acid derived from the biological sample, in particular DNA, is digested with one or more restriction endonuclease enzymes and the digested DNA is subjected to electrophoresis, transferred to a solid support such as, for example, a nylon or nitrocellulose membrane, and hybridised to the *Plasmodium* extrachromosomal genetic element probe as hereinbefore defined, optionally labelled with a reporter molecule. According to this embodiment, a specific pattern of DNA fragments is hybridised to the *Plasmodium* extrachromosomal genetic element probe, said pattern optionally specific for a particular *Plasmodium* ssp., to enable the user to distinguish between different species of the parasite.

Wherein the detection means is an amplification reaction for example a polymerase chain reaction or a nucleic acid sequence-based amplification (NASBA) system or a variant of same, one or more nucleic acid primer molecules of at least 15 contiguous nucleotides in length derivable from the *Plasmodium* extrachromosomal genetic element as hereinbefore defined, or its complementary nucleotide sequence or a homologue, analogue or derivative thereof, is hybridised to the biological sample comprising nucleic acid or alternatively, to nucleic acid derived from said sample and nucleic acid copies of the *Plasmodium* extrachromosomal genetic element present in said sample or a part or fragment thereof are enzymically-amplified.

Those skilled in the art will be aware that there must be a sufficiently high percentage nucleotide sequence identity between the *Plasmodium* extrachromosomal genetic element primers and the sequences in the template molecule to which they hybridise. As stated previously, the hybridisation conditions may be varied to promote hybridisation.

Preferably, the *Plasmodium* extrachromosomal genetic element primer is at least 95% identical to the complement of the nucleotide sequence in the template molecule to which it hybridises. More preferably, each *Plasmodium* extrachromosomal genetic element primer is substantially the same as the complement of the nucleotide sequence in the template molecule to which it hybridises.

Preferably, the *Plasmodium* extrachromosomal genetic element primer is contained in an aqueous mixture of other nucleic acid primer molecules. More preferably, the nucleic acid primer molecule is in a substantially pure form.

The *Plasmodium* extrachromosomal genetic element primer preferably comprises the sequence of nucleotides set forth in any one or more of SEQ ID Nos: 5-22 or FIG. 9 or 10 or a complementary strand or a homologue, analogue or derivative thereof.

In a more particularly preferred embodiment, the *Plasmodium* extrachromosomal genetic element primers are hybridised to a *Plasmodium* extrachromosomal genetic element contained in the biological sample being analysed, as probe pairs, in the combinations comprising SEQ ID Nos: 5 and 6; or SEQ ID Nos: 7 and 8; or SEQ ID Nos: 9 and 10; or SEQ ID Nos. 11 and 12; or SEQ ID Nos: 11 and 15; or SEQ ID Nos: 11 and 16; or SEQ ID Nos: 11 and 17; or SEQ ID Nos: 13 and 14; or SEQ ID Nos: 16 and 18; or SEQ ID Nos:21 and 22 or complementary strands, homologues, analogues or derivatives thereof.

The present invention particularly contemplates the use of primers as set forth in any one or more of SEQ ID Nos:11-18 as being useful in the differentiation of *Plasmodium* species as well as for detecting *Plasmodium* in a biological sample.

The *Plasmodium* extrachromosomal genetic element present in the biological sample, or a part or fragment thereof which is enzymically-amplified, is defined herein as a "template molecule". The template molecule may be a genetic sequence which is at least 40% identical at the nucleotide sequence level to SEQ ID Nos: 1-4 or to its complementary nucleotide sequence or to the *P. vivax, P. ovale, P. berghei, P. falciparum* or *P. malariae* sequences set forth in FIG. 9 or FIG. 10, the only requirement being that it comprises a *Plasmodium* extrachromosomal genetic element primer as hereinbefore defined.

Those skilled in the art will also be aware that, in one format, the polymerase chain reaction provides for the hybridisation of non-complementary *Plasmodium* extrachromosomal genetic element primers to different strands of the template molecule, such that the hybridised primers are positioned to facilitate the 5□□ 3□ synthesis of nucleic acid in the intervening region, under the control of a thermostable DNA polymerase enzyme. As a consequence, the polymerase chain reaction provides an advantage over other detection means in so far as the nucleotide sequence in the region between the hybridised *Plasmodium* extrachromosomal genetic element primers may be unknown and unrelated to any known nucleotide sequence.

In a particularly preferred embodiment, the nucleic acid template molecule comprises, in addition to other nucleotide sequences, a sequence of nucleotides derived from or contained within any one or more of the sequences set forth in SEQ ID Nos: 1-18 or a complementary sequence or a homologue, analogue or derivative thereof.

In an alternative embodiment, wherein the detection means is AFLP, the *Plasmodium* extrachromosomal genetic element primers are selected such that, when nucleic acid derived from the biological sample, in particular DNA, is amplified, different length amplification products are produced from different *Plasmodium* ssp. The amplification products may be subjected to electrophoresis, transferred to a solid support such as, for example, a nylon or nitrocellulose membrane, and hybridised to the *Plasmodium* extrachromosomal genetic element probe as hereinbefore defined, optionally labelled with a reporter molecule. According to this embodiment, a specific pattern of amplified DNA fragments is hybridised to the *Plasmodium* extrachromosomal genetic element probe, said pattern optionally specific for a particular *Plasmodium* ssp., to enable the user to distinguish between different species of the parasite in much the same way as for RFLP analysis.

The technique of AMD facilitates, not only the detection of a *Plasmodium* extrachromosomal genetic element in a biological sample, but also the determination of nucleotide sequence variants which differ from the *Plasmodium* extrachromosomal genetic element primers and probes used in the assay format.

Wherein the detection means is AMD, the *Plasmodium* extrachromosomal genetic element probe is end-labelled with a suitable reporter molecule and mixed with an excess of the amplified template molecule. The mixtures are subsequently denatured and allowed to renature to form nucleic acid "probe:template hybrid molecules" or "hybrids", such that any nucleotide sequence variation between the probe and the temple molecule to which it is hybridised will disrupt base-pairing in the hybrids. These regions of mismatch are sensitive to specific chemical modification using hydroxylamine (mismatched cytosine residues) or osmium tetroxide (mismatched thymidine residues), allowing subsequent cleavage of the modified site using piperidine. The cleaved nucleic acid may be analysed using denaturing polyacrylamide gel electrophoresis followed by standard nucleic acid hybridisation as described supra to detect the *Plasmodium* extrachromosomal genetic element nucleotide sequences.

Those skilled in the art will be aware of the means of end-labelling a genetic probe according to the performance of the invention described in this embodiment.

According to this embodiment, the use of a single end-labelled probe allows unequivocal localisation of the sequence variation. The distance between the point(s) of sequence variation and the end-label is represented by the size of the cleavage product.

In an alternative embodiment of AMD, the probe is labelled at both ends with a reporter molecule, to facilitate the simultaneous analysis of both DNA strands.

Wherein the detection means is IRS-PCR, the *Plasmodium* extrachromosomal genetic element primers are selected such that they each include one highly-repetitive restriction enzyme cleavage site, for example AluI, which is ubiquitous in many genomes. According to this embodiment, the appropriate restriction enzyme cleavage site is selected such that it is ubiquitous in *Plasmodium* extrachromosomal genetic element nucleotide sequences. The amplified template DNA is electrophoresed under conditions which facilitate high resolution and optionally probed with a labelled *Plasmodium* extrachromosomal genetic element probe.

Optionally, the amplified template DNA may be end-filled using Klenow fragment of DNA polymerase I or other suitable means, prior to the electrophoresis step.

According to this embodiment, different combinations of primers produce different patterns of amplified template nucleic acid.

Furthermore, with any primer combination used, each *Plasmodium* ssp. will produce a distinctive pattern of amplified template nucleic acid. As a consequence, the detection means is suitable for distinguishing between different *Plasmodium* ssp., in addition to being useful for the detection of the *Plasmodium* extrachromosomal genetic element per se in a biological sample.

Wherein the detection means is RT-PCR, the nucleic acid sample comprises an RNA molecule which is a transcription product of the *Plasmodium* extrachromosomal genetic element DNA or a homologue, analogue or derivative thereof. As a consequence, this assay format is particularly useful when it is desirable to determine expression of one or more *Plasmodium* extrachromosomal genetic element genes.

According to this embodiment, the RNA sample is reverse-transcribed to produce the complementary single-stranded DNA which is subsequently amplified using standard procedures.

Variations of the embodiments described herein are described in detail by McPherson et al. (1991), which is incorporated in the references.

The present invention clearly extends to the use of any and all detection means referred to supra for the purposes of diagnosing *Plasmodium* infection in humans and other animals.

The amplification reaction detection means described supra may be further coupled to a classical hybridisation reaction detection means to further enhance sensitivity and specificity of the inventive method, in particular by hybridising the amplified DNA with a *Plasmodium* extrachromosomal genetic element probe which is different from any of the *Plasmodium* extrachromosomal genetic element primers used in the amplification reaction.

Accordingly, a particularly preferred embodiment of the inventive method comprises the further step of detecting the amplified nucleic acid by contacting one or more of the nucleotide sequences set forth in SEQ ID Nos:19-22 thereto for a time and under conditions sufficient for hybridisation to occur.

Similarly, the hybridisation reaction detection means described supra may be further coupled to a second hybridisation step employing a *Plasmodium* extrachromosomal genetic element probe which is different from the probe used in the first hybridisation reaction.

The nucleotide sequences set forth in SEQ ID Nos: 19-22 are particularly suited to the performance of this embodiment, however those skilled in the art would readily be able to utilise the nucleotide sequences provided by the present invention in the performance of this embodiment. In particular, SEQ ID Nos:19 and 20 enable the identification of LSU and SSU sequences, respectively in a *Plasmodium* ssp., whilst SEQ ID Nos: 21 and 22 may be used for the specific detection of amplified or hybridised coxI genetic sequences derived from *Plasmodium falciparum* and *P. vivax*, respectively.

A further aspect of the invention provides an isolated extrachromosomal genetic element probe or primer derived from *Plasmodium* ssp, or a homologue, analogue or derivative thereof, according to the embodiments described herein.

Preferably, the extrachromosomal genetic element probe or primer is derived from a *Plasmodium* ssp. selected from the list comprising *P. berghei, P. falciparum, P. vivax, P. malariae, P. ovale, P. cynomolgi, P. gonderi, P. (Hepatocytis) kochi, P. inui, P. knowlesi, P. reichenowi, P. rodhaini, P. schwetzi, P. cathemerium, P. elongatum, P. relictum, P. lophurae, P. gallinaceum or P. yoelii*, amongst others.

In a particularly preferred embodiment, the extrachromosomal genetic element probe or primer is derived from *P. falciparum, P. berghei, P. ovale, P. vivax* or *P. malariae*. More particularly, the extrachromosomal genetic element probe or primer comprises a sequence of nucleotides which is at least 95% identical to the sequence set forth in any one or more of SEQ ID Nos: 1-22, or any one or more of the *P. berghei, P. ovale, P. vivax* or *P. malariae* sequences set forth in FIG. 9 or the *P. falciparum, P. ovale, P. vivax* or *P. malariae* sequences set forth in FIG. 10 or any one or more of the sequences set forth or a complementary nucleotide sequence, homologue, analogue or derivative thereof which is at least useful as a primer or probe for the diagnosis of infection of a human or animal subject by a *Plasmodium* ssp.

Alternatively, the probe or primer at least comprises a nucleotide sequence which is capable of encoding an amino acid sequence which is encoded by one or more of SEQ ID Nos:1-4 or a nucleotide sequence set forth in FIG. 9 or 10 or a complementary sequence thereto.

Wherein the extrachromosomal genetic element is a plastid or plastid-like molecule, it is preferred that it be derived from a species of *Plasmodium* other than *P. falciparum*.

A further aspect of the present invention contemplates a kit for convenient detection of a *Plasmodium* ssp. in a biological sample.

In an alternative embodiment, the kit of the present invention is also useful for convenient assay of infection by a *Plasmodium* ssp. parasite, wherein the sample being tested is derived from a human or other animal or mosquito suspected of being infected with said parasite.

The kit of the present invention is compartmentalized to contain in a first compartment, one or more nucleic acid molecules which comprise a sequence of nucleotides corresponding to a *Plasmodium* extrachromosomal genetic element or a complementary nucleotide sequence or a homologue, analogue or derivative thereof as hereinbefore defined.

In a preferred embodiment, the first compartment is adapted to contain one or more nucleic acid molecules which are at least 95% identical to the nucleotide sequence set forth in any one or more of SEQ ID Nos: 1-22 or any one or more of the *Plasmodium vivax, P. ovale, P. falciparum, P. berghei* or *P. malariae* sequences set forth in FIG. 9 and/or FIG. 10 or its complement or a derivative, homologue or analogue thereof. In a more preferred embodiment, the kit at least comprises one or more of the probe or primer sequences as set forth in any one of SEQ ID Nos: 5-22. The selection of SEQ ID Nos:21 and/or 22 as a probe is particularly suited to species-specific detection assay formats.

In a particularly preferred embodiment, the subject kit comprises a first primer and a second primer for the amplification of nucleic acid derived from or related to a *Plasmodium* extrachromosomal genetic element, such as a mitochondrion or plastid-like element. According to this embodiment, the first primer preferably comprises a sequence selected from SEQ ID Nos: 5, 7, 9, 11, 14 or 18 and the second primer preferably comprises a sequence selected from SEQ ID Nos: 6, 8, 10, 12, 13 or 15-17 or a derivative thereof.

In a more particularly preferred embodiment, the first and second primers comprise the sequences set forth in SEQ ID Nos: 5 and 6, or SEQ ID Nos: 11 and 12 or SEQ ID Nos: 11 and 15 or SEQ ID Nos: 11 and 16 or SEQ ID Nos: 11 and 17 or SEQ ID Nos: 13 and 14 or SEQ ID Nos: 16 and 18, respectively. These combinations are particularly suited to species-specific detection assay formats.

The invention clearly extends to kits at least comprising one or more pairs of said primers.

The invention extends further to such kits wherein both primers of a primer pair are provided in the same compartment, in aqueous solution or dried, such that the subject primers are at a relative concentration suitable for subsequent use in an amplification reaction.

The kit optionally comprises several second containers comprising a reaction buffer suitable for use in one or more of the detection means described herein and optionally several third containers comprising a nucleic acid molecule positive standard, to which the assay sample result may be compared.

In an exemplified use of the subject kit, a negative control reaction is carried out in which the contents of the first container are contacted with the contents of the second container. At the same time, the sample to be tested is contacted with the contents of the first and second containers for a time and under conditions sufficient for hybridisation to occur. If the reagents contained in the first container provided are not labelled with a reporter molecule, then the contents of the first container may be so labelled prior to the hybridisation reaction being carried out. The hybridised test sample and the negative control sample are then subjected to a detecting means as hereinbefore described. In analysing the results obtained using said kit, the control negative control reaction, test sample and nucleic acid molecule positive standard are compared side-by-side. The contents of the third container should always provide a positive result upon which to compare the results obtained for the negative control and test sample. If the results of the test sample are identical to the results obtained for the negative control, then the biological sample does not contain a *Plasmodium* ssp. extrachromosomal genetic element. However, if the test sample produces a nucleic acid molecule which is similar or the same as that contained in the positive standard, albeit of different intensity, then the biological sample contains a *Plasmodium* ssp. extrachromosomal genetic element.

The kit may further comprise additional probes and/or primers for the purpose of detecting amplified or hybridised nucleic acid in additional rounds of hybridisation and/or amplification.

The present invention is further described by the following non-limiting Examples.

EXAMPLE 1

Preparation of *Plasmodium berghei* Extrachromosomal DNA

*Plasmodium berghei* (ANKA strain) was maintained in Swiss White mice by continuous blood passage. Development of parasitemia was monitored daily by thin blood film analysis (Shute, 1988). Parasites were obtained by lysis of infected red blood cells with 1% saponin. The extrachromosomal element was purified from the parasites using a modified procedure of the Qiagen plasmid mini preparation kit (Qiagen Inc., Chatsworths, Calif., USA). Parasites from 10 infected mice (20-25 g) with a parasitemia of 60% were resuspended in 5 ml of P1 buffer, lysed with 5 ml of P2 buffer and neutralised with 5 ml of P3 buffer. After chilling on ice for 20 minutes, the precipitate was removed by centrifugation according to the manufacturer's recommendation and 200 µl of proteinase K (50 mg/ml) were added to the supernatant, which was then reincubated for 2 hours at 37° C. The supernatant was subsequently passed through a tip-20 Qiagen column which had previously been equilibrated with 1 ml of QBT buffer. The column was washed four times with 1 ml of QC buffer each. Finally, the extrachromosomal element was eluted with 1 ml of QF—buffer which was preheated to 65 C. The DNA was precipitated with isopropanol, washed with 70% ethanol, dried and dissolved in 25 µL of TE buffer.

EXAMPLE 2

Preparation and Restriction Digest of *P. berghei* Extrachromosomal DNA

Figure 1:
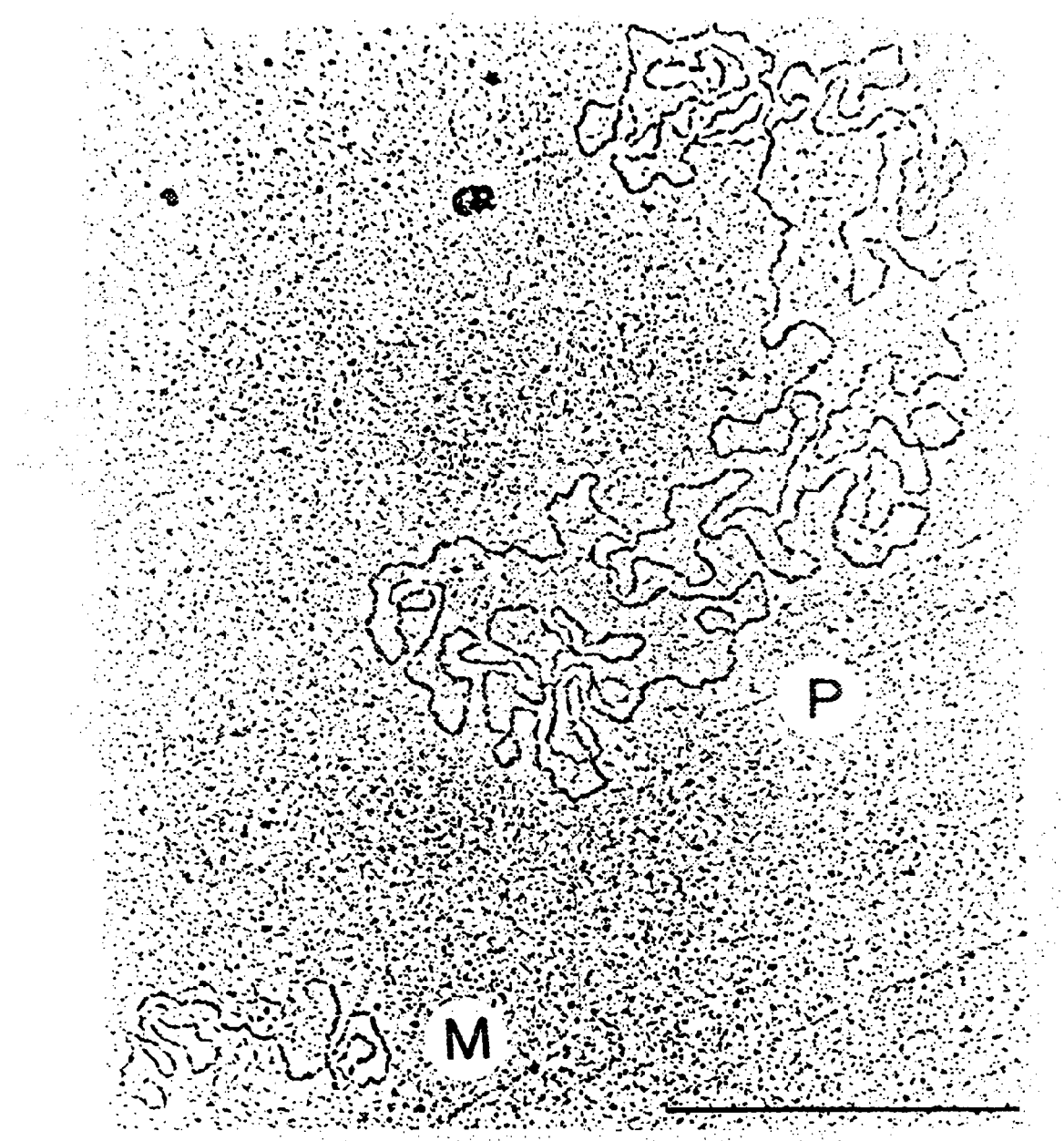
FIG. 1 is a copy of a photographic representation of an electron micrograph of the *Plasmodium berghei* extrachromosomal plastid preparation. P donates the *P. berghei* plastid while M is pBR322 (4.36 kb) used as a size marker. The bar represent the size of 1 kb.

*Plasmodium berghei* extrachromosomal DNA was extracted from the parasite using the Qiagen plasmid mini preparation kit (Qiagen Inc., Chatsworths, Calif., USA). Electron microscopic analysis of this preparation showed circular DNA elements of about 10 times the size of control pBR 322 plasmids (FIG. 1). The preparation was not homogenous and, in addition to the circular elements many linear molecules of different lengths were observed. The preparation is enriched for the extrachromosomal DNA elements of both circular and linear DNA representing the homologues of the 35 kb circle and 6 kb mitochondrial DNA. These are likely to be 6 kb DNA molecules which are tandemly arrayed in head-to-tail configurations.

Figure 2A:
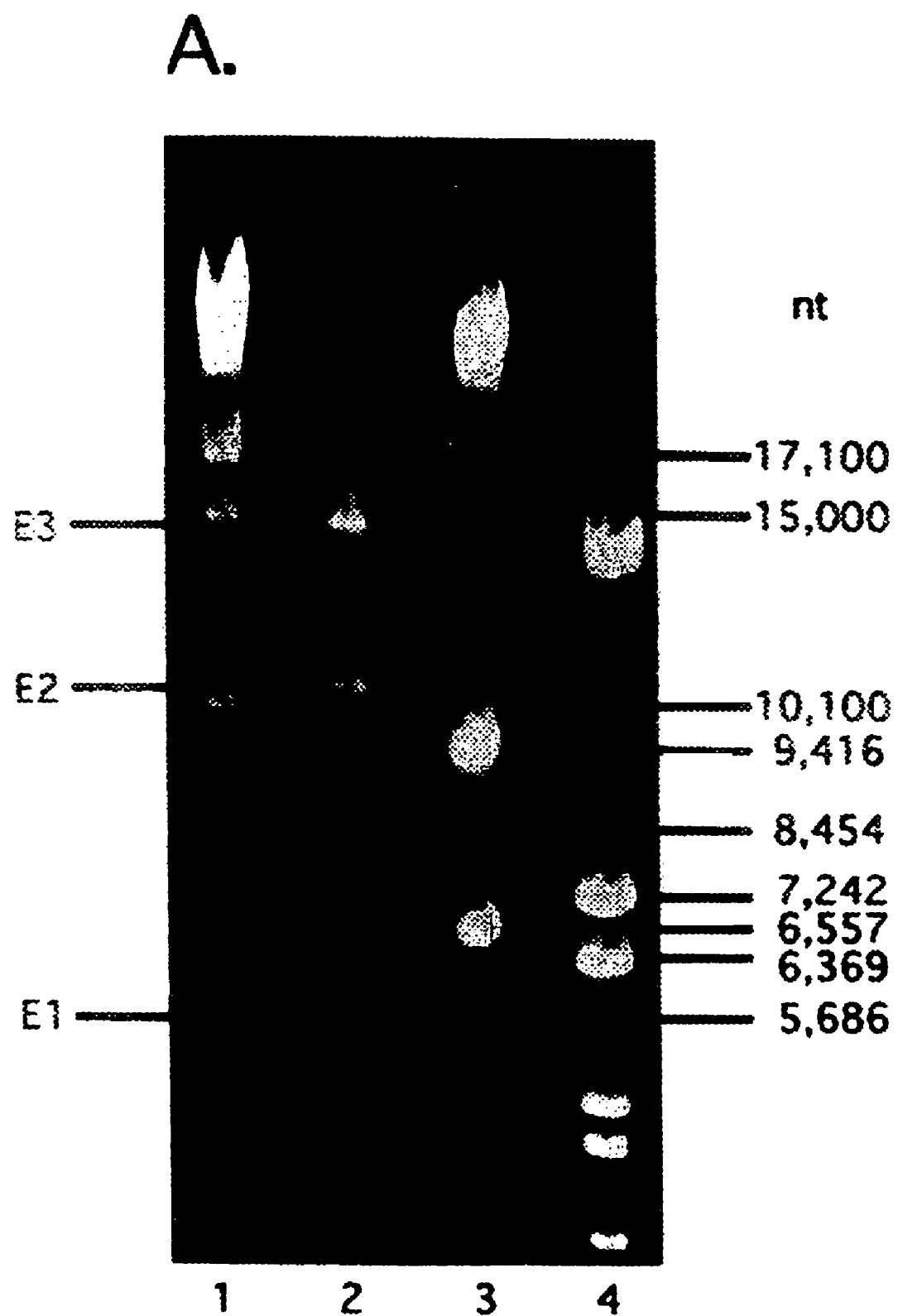
FIG. 2 is a copy of a photographic representation showing the EcoRI and HindIII restriction digests of *Plasmodium berghei* extrachromosomal plastid DNA. In panel (a), plastid DNA was digested with 20 units of EcoRI (New England Biolabs (NEB), Beverky, Mass., USA) in a reaction mixture of 10 uL. The digested products were separated on a 0.4% (w/v) agarose gel at 120 V for 6 hours. Lane 1 shows Lambda Monocut markers (NEB, USA); lane 2 the EcoRI digest resulting in three fragments (E1, E2 and E3); lane 3 shows Lambda DNA-Hind III digest markers (NEB, USA); and lane 4 shows Lambda DNA-BstEII digest markers (NEB, USA). Panel (b) shows a HindIII digest of the extrachromosomal element of *P. berghei*. The digested products were separated on a 0.6% (w/v) agarose gel at 100 V for 6 hours. Lane 1 shows Lambda DNA-BstEII digest markers (NEB, USA); lane 2 shows a HindIII digest of *P. berghei* DNA resulting in six fragments (H1, H2, H3, H4, H5 and H6); and lane 3 shows Lambda DNA-BstEII digest markers (NEB, USA).
Figure 2B:
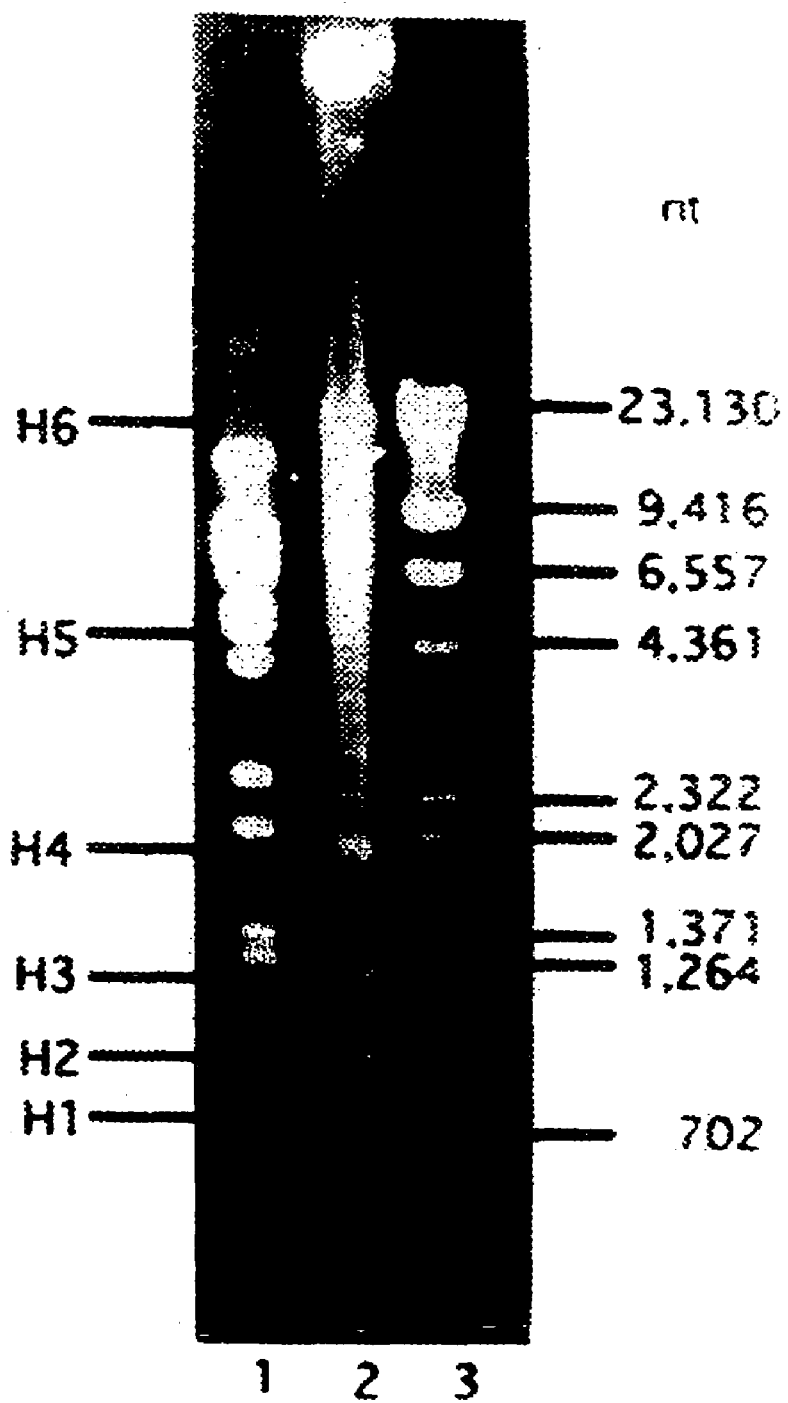

The extracted plastid DNA was digested into 3 fragments of 15 kb (E3), 10 kb (E2) and 5.7 kb (E1) by EcoRI (FIG. 2a). This gives the plastid an estimated size of 31 kb. Hind III digest of the DNA yielded 6 fragments of 22.4 kb (H6), 4.4 kb (H5), 1.85 kb (H4), 1.23 kb (H3), 0.95 kb (H2) and 0.7 kb (H1), respectively (FIG. 2b). H3 and H5 are fragments from the mitochondrial 6 kb genome.

The estimated size of the *P. berghei* circle is 31 kb according to Electron microscopic measurements using pBR322 as control as well as from size calculations using the EcoRI restriction digest fragments.

Extrachromosomal circular DNA has not only been found in *Plasmodium* species but also in other parasitic protozoa such as *Babesia* and *Entamoeba* (Gozar and Bagnara, 1995; Egea and Lang-Unnasch, 1995; Sehgal et al., 1994) suggesting a common evolutionary origin of this circular DNA material (Williamson et al. 1994). By maintaining such extrachromosomal information during evolution it appears that this highly conserved and seemingly functional extrachromosomal DNA molecule is important for parasite development and that knowledge of its functions will greatly aid in providing novel targets for drug development.

Our preliminary tests using an antisense oligonucleotide approach indicate that this extrachromosomal element may indeed be crucial for parasite survival.

EXAMPLE 3

PCR Amplification and Sequence Analysis of Plastid DNA

In order to obtain a genetic map of the approximately 35 kb *Plasmodium berghei* extrachromosomal plastid, polymerase chain reaction (PCR) amplifications and sequence analysis of plastid DNA were carried out.

PCR was performed using the United States Biochemical (Amersham) PCR kit in a 100 µl reaction mixture containing 2 mM $MgCl_2$, 0.2 mM of each dNTP, 4 ng/µL of each primer, 5 units of Taq DNA polymerase, 10 µL of the 10×PCR buffer and 1 µL of the extrachromosomal DNA prepared as described in Examples 1 and 2. A "hot start" was carried out at 95° C. for 5 minutes without the dNTPs and Taq polymerase. This was followed by the addition of dNTPs and Taq polymerase and 40 cycles of denaturation (90° C., 1.5 minutes), annealing (55° C., 3 minutes) and extension (72° C., 5 minutes). A final extension was performed at 72° C. for 10 minutes.

The PCR products were loaded onto a 1% low melting point agarose gel, extracted by the freeze-thaw method (Shoemaker and Salyers, 1990) and then cloned into the Promega pGEM-T vector.

Clone H2a was constructed by cloning the second fragment of a HindIII digest of the extrachromosomal element into the pBluescript vector. (Stratagene, USA).

The clones were sequenced using the ABI PRISM Dye terminator cycle sequencing kit from Perkin-Elmer on the 373A DNA sequencer from Applied Biosystems. The percentage homology with the *P. falciparum* extrachromosomal element (Accession No. X 95275 and X 95276) was obtained using the Martinez/Needleman-Wunsch DNA alignment programme from DNASTAR.

PCR amplification of different parts of the extrachromosomal plastid were performed using primer sets homologous to sequences from the 35 kb circle of *P. falciparum* (Table 1). These include the primer sets comprising SEQ ID Nos: 5 and 6 (L/L Primer set), SEQ ID Nos: 7 and 8 (L/S primer pair) and SEQ ID Nos: 9 and 10 (S/S Primer pair, homologous to the small-subunit (ssu)-rRNA of *P. falciparum*).

The amplified regions obtained with these primers lay within the large subunit (lsu)-rRNA gene, rpo B gene, the cluster of 10 tRNAs, part of the cluster of four tRNAs located close to the 3' end of the tufA gene in *P. falciparum* as well as the region between the lsu-rRNA and the ssu-rRNA genes.

All PCR fragments were cloned into the pGem-T vector from Promega. Sequence analysis performed using the Martinez/Needleman-Wunsch DNA alignment on all clones which had been purified using Qiagen midi plasmid preparation columns showed a similarity index of greater than 80% with the *P. falciparum* circle except for the PPH and PWQ fragment (Table 1). The PRB fragment was homologous to the *P. falciparum* rpo B gene with a similarity index of 87.9% for the DNA sequence and 85.6% for the corresponding amino acid sequence (using the Lipman-Pearson protein alignment). The PPH sequence spanning the cluster of 10 tRNA genes had a similarity index of only 78%. While the tRNA coding regions were highly similar to those in *P. falciparum* the non-coding spaces were much less conserved between the two *Plasmodium* species.

In order to examine if the lsu-rRNA gene in *P. berghei* exists as a repeat, a single forward primer (L3) homologous to the 3' end of the *P. falciparum* lsu-rRNA sequence and 2 distinct reverse primers homologous to the ORF 470 (04) and the start of the cluster of 10 tRNA genes (3H) of the *P. falciparum* circle were designed. The fragment amplified with the L3/04 primer set (PL470) was distinct from that amplified using the L3/3H set (PLH). Sequence analysis of PL470 showed a homology of 83% with the same region in *P. falciparum*. The sequence of PLH was homologous to the 3' end of the lsu-rRNA and the 3' end of rps 4 of the *P. falciparum* circle (data not shown) indicating that the lsu-rRNA gene exists as a repeat in *P. berghei*. In addition, a cluster of intervening tRNA genes was present between the lsu-rRNA and ssu-rRNA genes (fragment PLS). This repetition and arrangement is similar to the organisation of the *P. falciparum* circle, where a palindromic sequence of genes for the subunit rRNAs and several tRNAs exists. Each arm of the palindrome contains one ssu and one Isu-rRNA gene and a cluster of intervening tRNA genes (Gardner et al., 1993).

From the nucleotide sequences set forth in SEQ ID Nos: 1-4, it is clear that the genes in the *P. berghei* circle are homologous to those in the 35 kb *P. falciparum* circle. Major differences in sequence are observed in the non-coding spaces between tRNA gene clusters. The arrangement of genes appears to be similar in both *Plasmodium* species and a repeat of the rRNA genes does not only exist in *P. falciparum* but also in the *P. berghei* circle.

EXAMPLE 4

Southern Hybridisation of Restriction Fragments

Fragments from the HindIII and HindIII/EcoRI digests of the *Plasmodium berghei* extrachromosomal element were separated on a 1% (w/v) agarose gel at 120 V for 4 hours. The separated fragments were then transferred onto a Nylon membrane (Hybond-N, Amersham) by capillary action using 20×SSC buffer (0.3M sodium citrate, 3M sodium chloride, pH 7.0). Southern hybridization was performed using probes specific for the approximately 35 kb circle that were made from the cloned PCR products, according to the preceding Examples.

The PCR products were liberated from the vector by digestion with ApaI and PstI. The enhanced chemiluminescence (ECL) direct nucleic acid labelling and detection system (Amersham International PLC, England) was used for labelling the probe, for hybridisation and for detection. Each of these steps were carried out according to the manufacturer's instruction. First, 8 µg of probe in a volume of 20 µL were denatured by boiling for 5 minutes and immediately cooled on ice for 5 minutes. 20 µL of labelling reagent were then added. This was followed by the addition of 20 µL of glutaraldehyde solution. The mixture was incubated for 20 minutes at 37° C. before addition to the hybridization buffer. The ECL Gold hybridisation buffer containing 0.5M NaCl and 5% blocking agent was used for hybridisation. The blots were prehybridised for 2 hours at 42° C. and the labelled probe was added to a final concentration of 800 ng DNA/ml. Hybridisation was allowed to proceed overnight at 42° C. The blots were washed twice in primary wash buffer containing 6M urea, 0.4% SDS and 0.5×SSC at 42° C. for 20 minutes. This was followed by two rounds of washing in 2×SSC buffer at room temperature for 10 minutes. For detection, 6.5 ml of equal volumes of detection reagents 1 and 2 were mixed and added to the blot for 1 minute. The blot was then drained, wrapped in Saran Wrap and the DNA side was exposed to an autoradiography film.

Figure 3A:
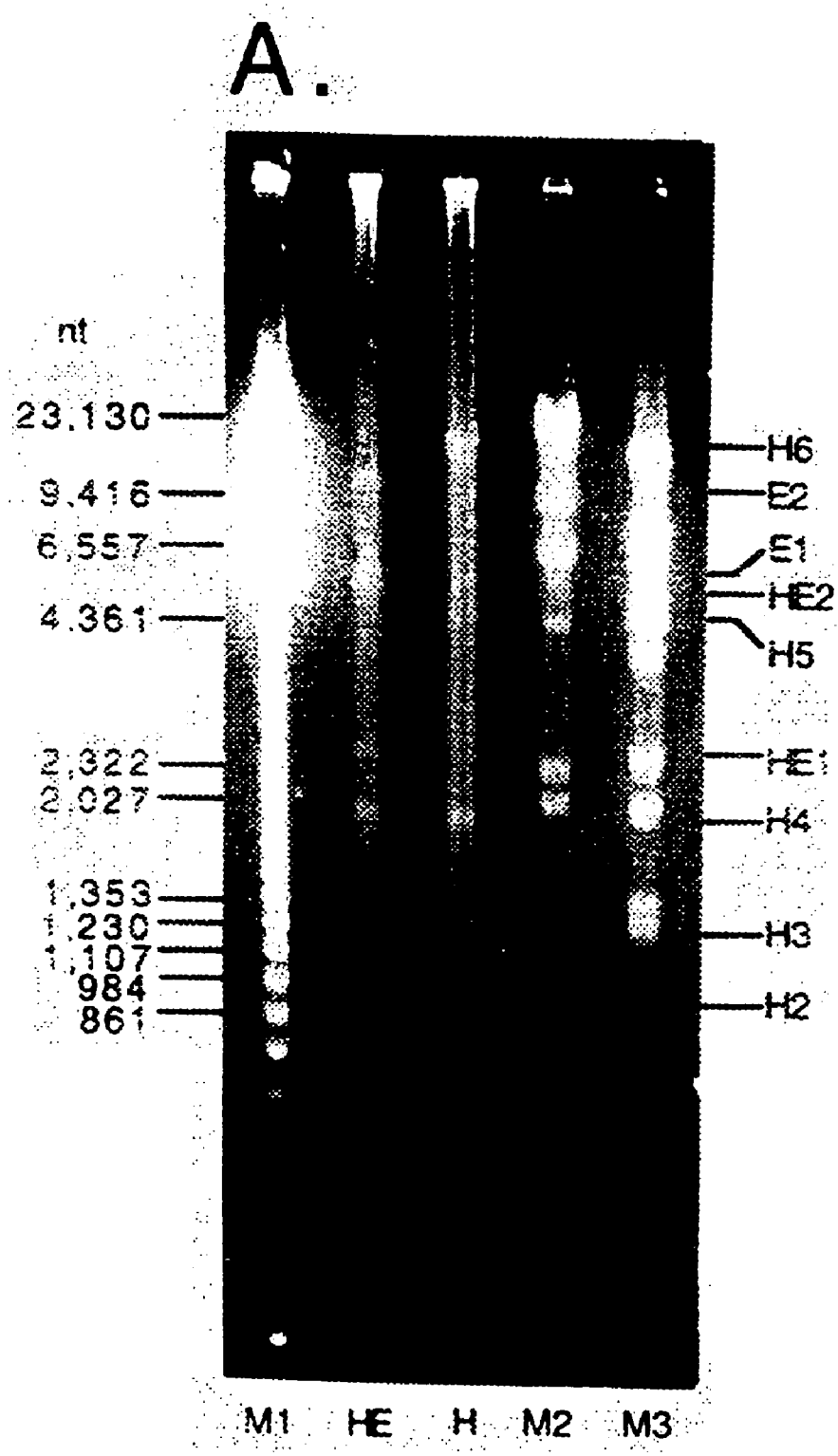
FIG. 3 is a copy of a photographic representation of a Southern Hybridization of HindIII and HindIII/EcoRI digests of the *Plasmodium berghei* extrachromosomal element. Panel (a) shows restriction digests of *P. berghei* extrachromosomal DNA. Lane M1 shows the 123 bp DNA marker (Gibco-BRL); lane HE the HindIII/EcoRI digest resulting in 8 fragments (H2, H3, H4, HE1, H5, HE2, E1 and E2); lane H the HindIII digest resulting in 6 fragments, H2, H3, H4, H5 and H6); lane M2 the Lambda DNA-HindIII digest markers (NEB, USA); and lane M3 the Lambda DNA-BstEII digest markers (NEB, USA). Panel (b) shows a Southern hybridization of the fragments in panel (a) with probe PS 1. Panel (c) shows a Southern hybridization of the fragments in panel (a) with probe PL470. Panel (d) shows a Southern hybridization of the fragments in panel (a) with probe PWQ.
Figure 3B:
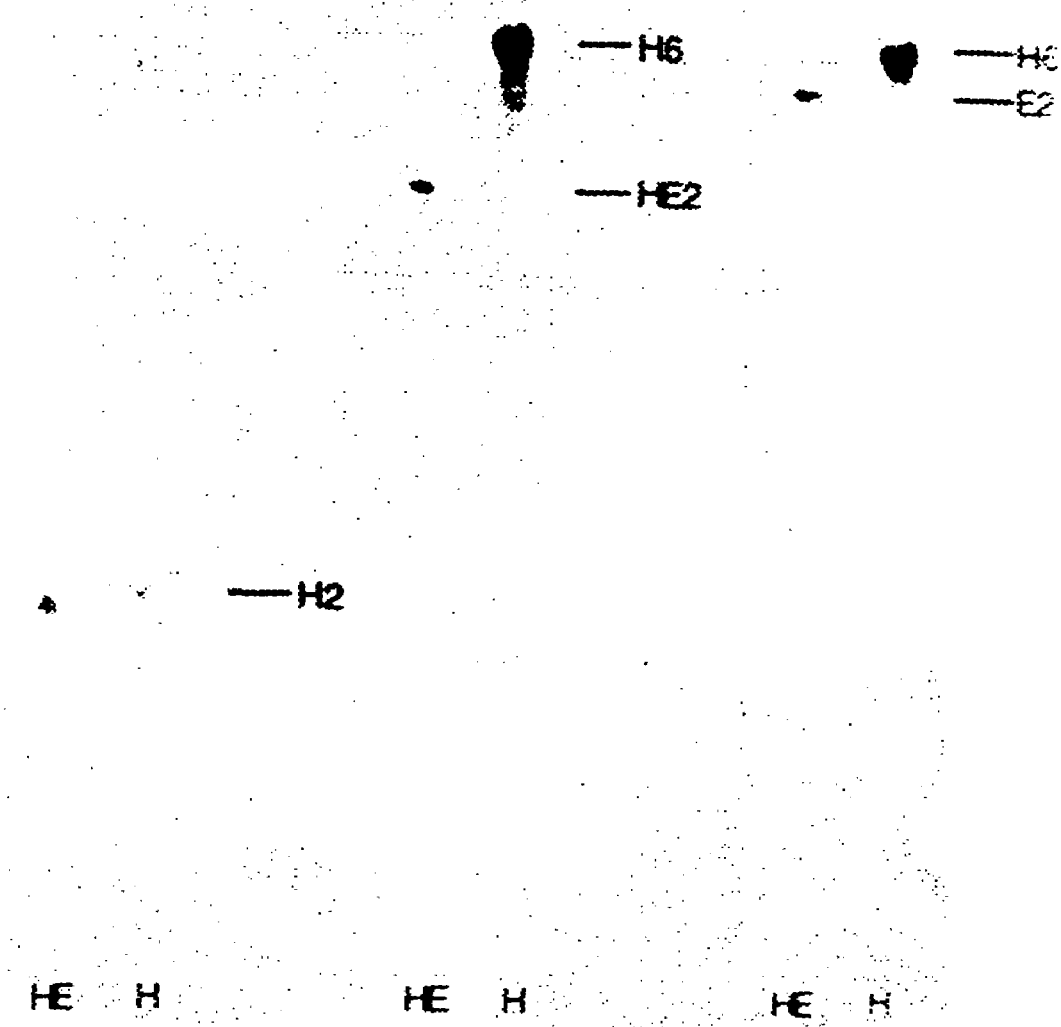

A double digest of the *P. berghei* circle with HindIII followed by EcoRI resulted in the following fragments: 10 kb (E2), 5.7 kb (E1), 5.0 kb (HE2), 4.4 kb (H5), 2.3 kb (HE1), 1.85 (H4), 1.23 (H3), 0.95 (H2) and 0.7 kb (H1). The PS 1 probe hybridised to H2, the PL470. probe hybridised to H6 and HE2 while the PWQ probe hybridised to H6 and E2 (FIG. 3).

The results obtained with various other probes are shown in Table 2. Of interest to note is that H2 contained 2 distinct fragments which hybridised with PS 1 and PL3. One of the H2 fragments (H2a) was cloned into Bluescript vector (pBS KS (II)+) and sequenced. The sequence corresponded to the internal region of the *P. falciparum* 35 kb ssu-rRNA gene (Table 1, sequence H2a). The other fragment (H2b) arose from the two Hind III sites within the Isu-rRNA gene. The presence of these two sites was confirmed by the sequences from the

TABLE 1

Description of clones of various segments from the extrachromosomal element in *P. berghei* and their percentage homology with *P. falciparum*.

| Name of clone | Description | Size (bp) | Percentage homology with *P. falciparum* | EcoRI/HindIII sites |
| --- | --- | --- | --- | --- |
| H2a | Second fragment of HindIII digest containing SSU rRNA | 949 | 92.3 | Two HindIII sites |
| PS1 | PCR product of SSU rRNA | 526 | 94.3 | Nil |
| PL1 | PCR product of LSU rRNA | 595 | 95.5 | One HindIII site |
| PL2 | PCR product of LSU rRNA | 595 | 93.8 | One HindIII site |
| PL3 | PCR product of LSU rRNA | 735 | 88.8 | One HindIII site |
| PLS | PCR product of tRNAs between LSU and SSU rRNA | 973 | 87.3 | Nil |
| PPH | PCR product of tRNAs before the repeat | 1000 | 78.0 | One EcoRI site |
| PLH | PCR product from LSU rRNA to His-tRNA | 1118 | 82.3 | Nil |
| PL470 | PCR product from LSU to ORF470 | 1125 | 83.0 | Nil |
| PRB | PCR product of the RpoB gene | 516 | 87.9 | One EcoRI site |
| PWQ | PCR product of the Phe-tRNA | 161 | 69.6 | Nil |
| PB-1 | Sequence derived from clones spanning the Ile-tRNA, the ssu-rRNA, the Isu-rRNA and the ORF-470 genes | 5849 | 88.5 | 4 Hind III sites |
| PB-2 | Sequence derives from clones spanning the regions within the Isu-rRNA, the rps 4 and the cluster of 10 tRNA genes | 2621 | 80.2 | 1 Hind III site and 1 Eco RI site |

TABLE 2

Southern analysis of restriction digests.

| Probe | HindIII digest | HindIII/EcoRI digest | EcoRI digest |
| --- | --- | --- | --- |
| PS1 | H2 | H2 | N.D. |
| PLS | H4 | H4 | N.D. |

TABLE 2-continued

Southern analysis of restriction digests.

| Probe | HindIII digest | HindIII/EcoRI digest | EcoRI digest |
|---|---|---|---|
| PWQ | H6 | E2 | E2 |
| PL1 | H6 | HE2 | N.D. |
| PL2 | H6 | HE1, HE2 | N.D. |
| PL3 | H2, H4 | H2, H4 | E3 |
| PRB | H6 | HE2 | E2, E3 |
| PL470 | H6 | HE2 | E3 |
| PPH | H6 | HE1 | E3 |
| PB6K-4 | H3, H5 | H3, H5 | N.D. |

PL2 and PL3 PCR products. In addition, both the H5 and the H3 fragments hybridised with probes corresponding to the *P. berghei* 6 kb mitochondrial DNA. This was not unexpected as the preparation was found to contain linear molecules as shown by electron microscopy (FIG. 1).

EXAMPLE 5

Physical and Genetic Map of the *P. berghei* 35 kb Circle

Figure 4A:
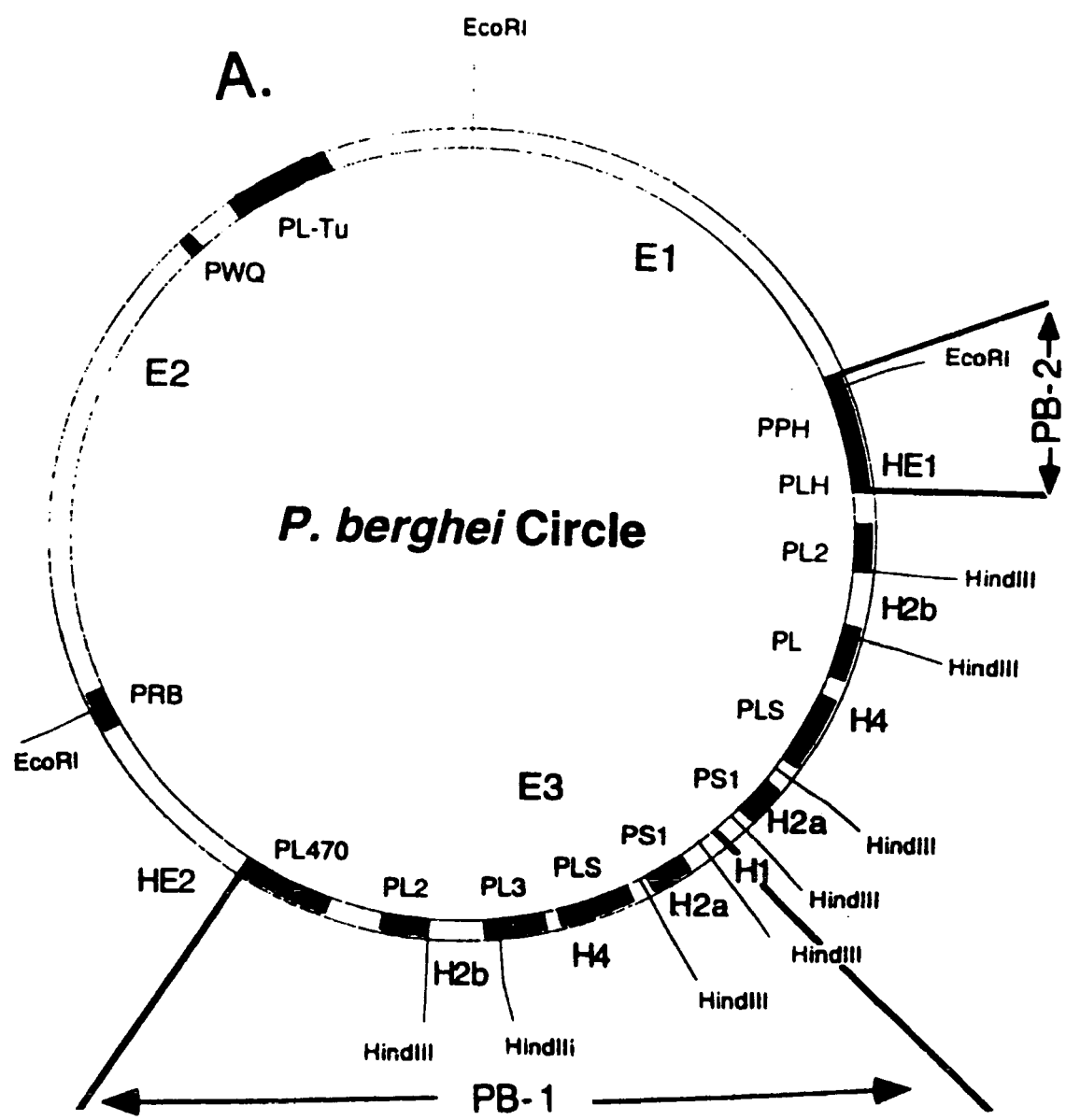
FIG. 4 is a representation of the physical and genetic map of the *Plasmodium berghei* circle. Panel (a) is a schematic representation of the arrangement of various genes and the EcoRI and HindIII sites are shown. The three EcoRI fragments, E1, E2 and E3 as well as the HindIII fragments H1, H2a, H2b as well as H4 are shown. Fragment H6 comprises of HE1, E1, E2 and HE2. The relative position of the various PCR products (Table 1) is also indicated as solid bars. Panel (b) shows a comparison between homologous genes on the *Plasmodium falciparum* and *Plasmodium berghei* plastid circles and tRNA genes are specified by a single letter amino-acid code.

A map of the approximately 35 kb *P. berghei* extrachromosomal circle was constructed based on the information from the restriction digests, Southern hybridisation experiments and the sequence analysis of the PCR fragments (FIG. 4a). The PPH and PRB fragments each contained an EcoRI restriction site (Table 1). The three EcoRI and six Hind III fragments were arranged according to their hybridisation patterns. The PRB probe hybridised to both the E2 and E3 fragments from the EcoRI digest indicating that E2 is positioned next to E3 (Table 2).

The HE2 fragment obtained from the double digest with EcoRI and Hind III, hybridised to probes PRB, PL470 and PL2 while H2b and H4 hybridised to probe PL3. Both the PL2 and PL3 fragments are regions within the lsu-rRNA gene, whereas the PL470 fragment contains 3' end of the lsu-rRNA gene. Thus, the ORF470 must be located next to the PL2 fragment. H2b is situated between HE2 and H4 since H4 also hybridised with the PLS probe which contains the 5' ends of both the small and large subunits rRNA genes. H2a hybridised with probe PS 1 which corresponds to a region within the ssu-rRNA gene, therefore H2a must be located next to H4. Finally, HE1 is placed next to E1 as HE1 hybridised to probes PPH, PLH and PL2.

Figure 4B:
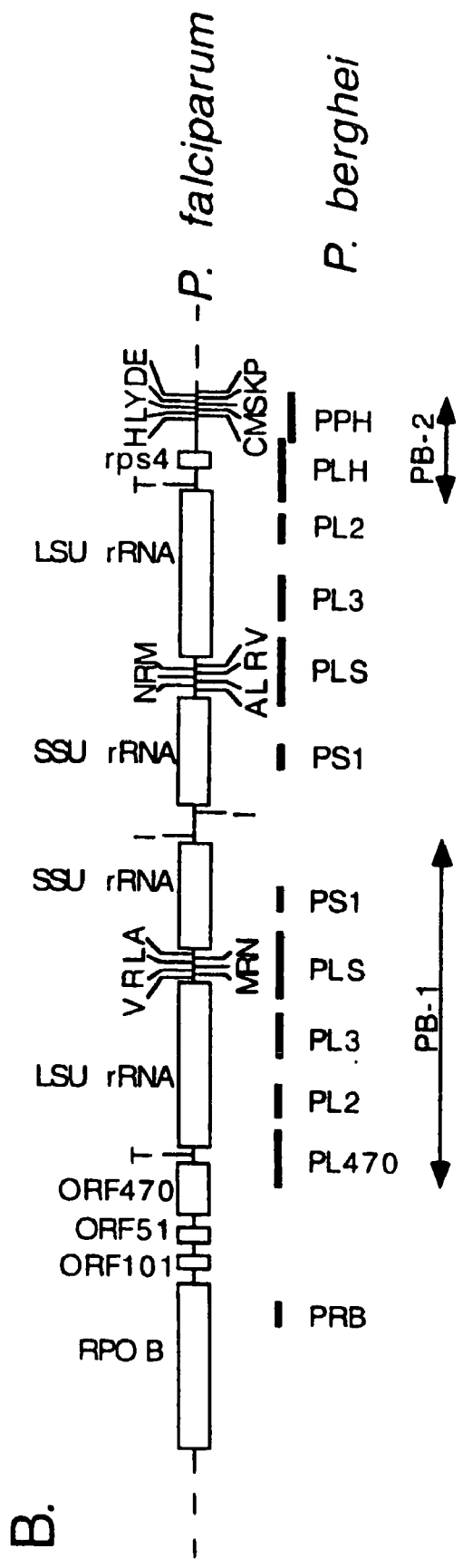

The arrangement of genes on the *P. berghei* circle spanning the rpo B gene and the cluster of 10 tRNAs genes is thus very similar to that of the *P. falciparum* 35 kb circle (FIG. 4b). The *P. berghei* circle encodes organelle-like rRNAs, tRNAs, ribosomal proteins and RNA polymerase subunits, similar to those identified for *P. falciparum* (Preiser et al., 1995).

EXAMPLE 6

Reverse Transcription-PCR of LSU-rRNA and SSU-rRNA

In order to determine if the approximately 35 kb *Plasmodium berghei* extrachromosomal genetic element is transcriptionally active, total RNA from *P. berghei* was isolated using the RNeasy total RNA kit (Qiagen Inc., Chatsworth, Calif., USA) and a combined reverse transcription—PCR (RT-PCR) reaction was carried out to amplify lsu-rRNA or ssu-rRNA transcripts.

Total RNA was isolated from *Plasmodium berghei* using the Qiagen RNeasy Total RNA kit (Qiagen Inc., Chatsworth, Calif., USA). Parasites from 10 infected mice with a parasitemia of 60% were resuspended in 350 µl of lysis buffer RLT and homogenised using a QIAshredder (Qiagen Inc.). The homogenate was cleared of insoluble material by centrifugation and 1 volume of 70% ethanol was added. The entire sample was then added to the RNeasy spin column and washed with RW1 buffer followed by two washes with RPE buffer. The RNA was eluted out with 35 µl of water. 5 µl of the RNA was used as starting material for the Access RT-PCR system (Promega, Madison, USA). Two primer sets, L/L (SEQ ID Nos: 5 and 6) and S/S (SEQ ID Nos: 9 and 10) were used. The manufacturer's protocol was followed with the exception of the annealing step for PCR amplification. Annealing was allowed to proceed at 55° C. for 1 minute. The PCR products were separated on a 1% (w/v) agarose gel and visualised by ethidium bromide staining.

Figure 5:
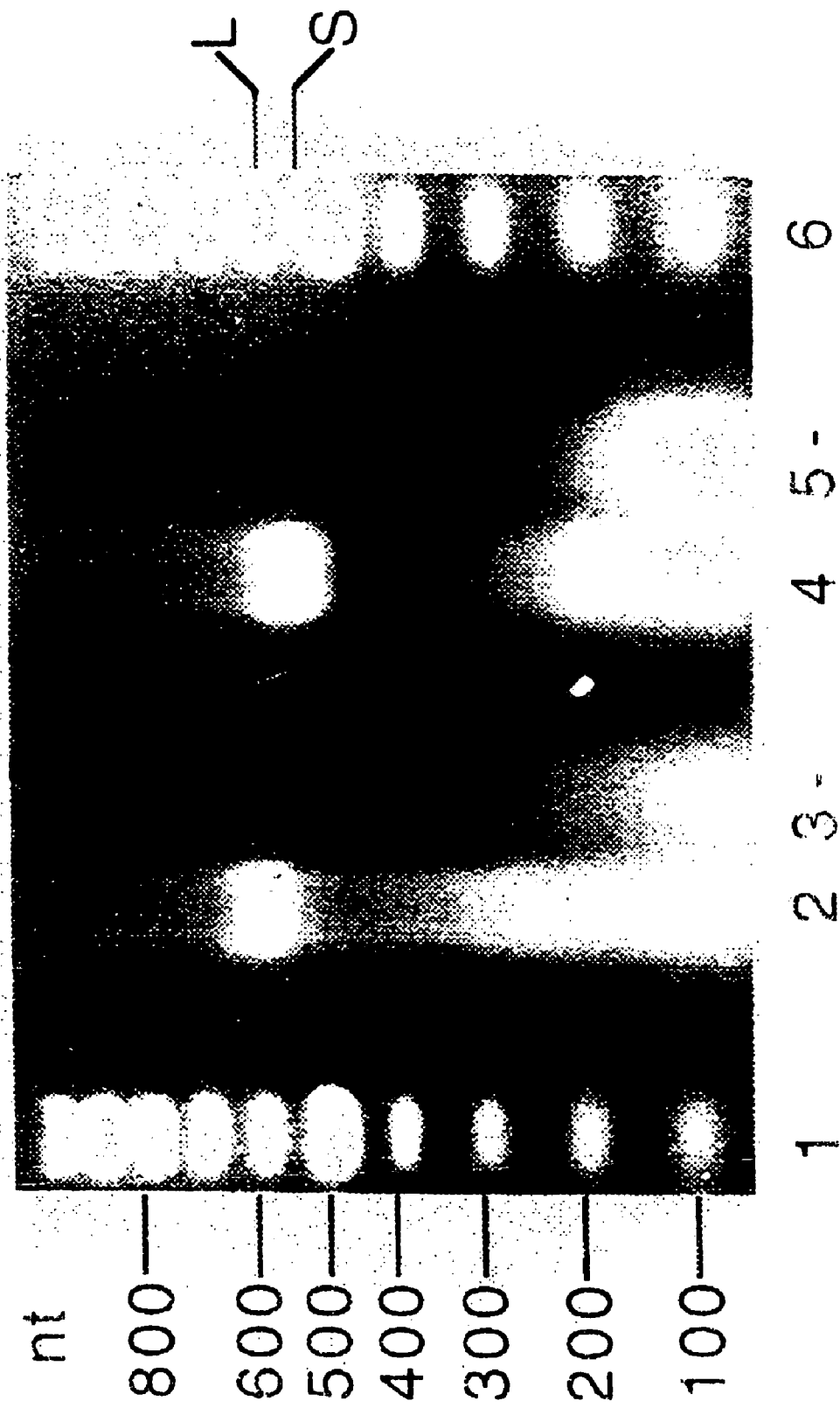
FIG. 5 is a copy of a photographic representation showing RT-PCR analysis of rRNAs transcripts. Lane 1 and 6 show the 100 bp DNA ladder (Promega), lanes 2 and 3 show the RT-PCR product (L) using a set of Isu-rRNA gene specific primers and lanes 4 and 5 show the product (S) using a set of ssu-rRNA gene specific primers respectively. The (−) lanes show reactions without the reverse transcriptase enzyme.

Amplification using the RT-PCR kit from Promega and a set of primers homologous to the ssu-rRNA produced a 526 bp fragment while amplification using a set of lsu-rRNA specific primers resulted in a 594 bp fragment (FIG. 5).

EXAMPLE 7

Assay of Blood Samples for the Presence of *Plasmodium* ssp.

A total of 482 *Plasmodium*-infected blood samples from four different locations, Singapore, Laos, Pakistan, India and Colombia and a defined number of negative control blood samples, were analysed for the presence of *Plasmodium* extrachromosomal genetic elements, using the polymerase chain reaction.

Briefly, 10-100 µL of whole patient blood (either peripheral blood from a finger prick sample or venal blood) was spotted onto a filter disc or equivalent solid support and directly amplified, using each of the primer pairs:

L/L PRIMER PAIR:

SEQ ID NO:5:
5'-GACCTGCATGAAAGATG-3'

SEQ ID NO:6:
5'-GTATCGCTTTAATAGGCG-3'

L/S PRIMER PAIR:

SEQ ID NO:7:
5'-GCCACTACTATGAAAATC-3'

SEQ ID NO:8:
5'-GCGTTCATTCTGAGCTAG-3'

S/S PRIMER PAIR:

SEQ ID NO:9:
5'-GCGGTAATACAGAAAATGCAAGCG-3'

SEQ ID NO:10:
5'-AGCACGAACTGACGACAGCCATGCAC-3'

PCR Buffer used in the amplification reactions comprised the following:
70 mM Tris. pH 8.8
20 mM Ammonium sulphate 1 mM DTT
0.1 μg/μL BSA (or 0.01% geletin)
2.5 mM MgCl$_2$ Each 100 μL reaction included 0.4 μg of each primer, 0.8 mM dNTP mixture and 5 U of TaqI polymerase.

The template DNA was fixed with methanol for 5 mins. A "hot start" was carried out at 95° C. for 5 minutes without the dNTPs and Taq polymerase. This was followed by the addition of dNTPs and Taq polymerase and 40 cycles of denaturation (90° C., 1.0 mins), annealing (56° C., 2 mins) and extension (72° C., 1 min). The PCR products were analysed by agarose gel electrophoresis. The results are shown in Tables 3 and 4. The L/L primer set was capable of identifying *Plasmodium falciparum, P. vivax, P. ovale* and *P. malariae* in 100% of cases, suggesting that this primer pair is useful in the genera-specific diagnosis of *Plasmodium* infection. The S/S primer set was capable of efficiently diagnosing *P. falciparum* and *P. malariae* in 100% of cases. In marked contrast, the L/S primer set resulted in only poor diagnosis of *P. vivax* and *P. malariae,* however detected the presence of *P. falciparum* in blood samples, suggesting that this primer pair is species-specific. The human actin primer set AC1/2 were used as positive controls.

Results also indicate that the selection of primer pairs in the diagnostic assay was of primary importance in determining the reliability of the assay in diagnosing infection by *Plasmodium* ssp.

TABLE 3

Number and origin of Plasmodium infected samples

| Origin | Number | P. fal | P. viv | P. mal | P. ova | Mixed | Controls |
|---|---|---|---|---|---|---|---|
| Singapore | 74 | 15 | 26 | 2 | 2 | 3 | 26 |
| Laos | 16 | 15 | 1 | — | — | — | — |
| Pakistan | 68 | 14 | 53 | — | — | — | 1 |
| India | 11 | 1 | 10 | — | — | — | — |
| Colombia | 313 | 1 | 29 | — | — | — | 283 |
| Total | 482 | 46 | 119 | 2 | 2 | 3 | 310 |

TABLE 4

PCR results using the primer pairs L/L, L/S, S/S and AC1/2

| Species | L/L | L/S | S/S | AC1/2 |
|---|---|---|---|---|
| P. fal | 46/46 (100%) | 14/20 (70%) | 21/21 (100%) | nd |
| P. viv | 119/119 (100%) | 6/58 (10%) | 48/57 (84%) | nd |
| P. mal | 2/2 (100%) | 0/1 (0%) | 1/1 (100%) | nd |
| P. ova | 2/2 (100%) | nd | nd | nd |
| mixed | 3/3 (100%) | nd | nd | nd |
| controls | 0/310 (0%) | nd | nd | 92/92 (100%) | nd = not done

EXAMPLE 8

Direct PCR Amplification of Extrachromosomal *Plasmodium* DNA from Dried Blood Spots 1. Specimen Collection Blood was collected by fingerprick (5-10 μl) or by venipuncture from subjects with Giemsa smear-positive *Plasmodium falciparum, Plasmodium vivax* and *Plasmodium malariae* malaria as well as from healthy controls, and spotted in replicates onto Whatman filter paper. *Plasmodium berghei* (ANKA) infected mouse blood (5 μl) was collected from the tail. *Plasmodium berghei* infections were maintained by serial blood passage of $10^7$ parasites. Dried blood spots were placed individually into 200 μl PCR tubes and fixed with the addition of methanol for 5 minutes. The methanol was poured off and the blood spot was dried thoroughly prior to PCR amplification.

2. PCR Amplification

Amplification was carried out as previously described (Long et al, 1995) with some modifications. Each 100 μl reaction mixture contained 1×PCR buffer (70 mM Tris, pH 8.8, 20 mM $(NH_4)_2SO_4$, 1 mM DTT, 0.1 μg/μl BSA) 2.5 mM MgCl$_2$, 0.4 μg of each primer, 5 units of Taq DNA polymerase (Amersham) and 0.2 mM of each dNTPs. Reaction tubes were overlaid with one drop of mineral oil. The reaction was soaked at 95° C. for 5 minutes then held at 80° C. prior to the addition of Taq DNA polymerase and dNTPs. Amplification involved 40 cycles of 1 minute denaturation at 90° C., 2 minute annealing at 52° C. and 3 minutes primer extension at 72° C. A 5 minute primer extension at 72° C. was included following the final cycle.

3. Sequences of Primers.

The primers used for amplifying the LSU-rRNA gene were as follows:

```
L1   5'GAC CTG CAT GAA AGA TG 3';    (SEQ ID NO: 5)
and

L2   5'GTA TCG CTT TAA TAG GCG 3'.   (SEQ ID NO: 6)
```

A second set of primers were designed to amplify the dihydrofolate reductase-thymidylate synthase (DHFR-TS) gene from *P. berghei* genomic DNA in control experiments: DHFR1 5' GCA ATA TGT GCA TGT TGT AAA 3' (SEQ ID NO:48); and

DHFR2 5'ATT CTT TAT AAA CAG ACG 3' (SEQ ID NO:49).

The primers used for amplifying the human β-actin gene were as follows:

```
AC1 5'GGGCGACGAGGCCCAGAGC3';        (SEQ ID NO:50)

AC2 5' GCA TCC TGT CGG CAA TGC C 3'; (SEQ ID NO:51)

AC3 5' AAG GAG AAG CTG TGC TAC 3';  (SEQ ID NO:52)
and

AC4 5' TCA TGA TGG AGT TGA AG 3'.   (SEQ ID NO:53)
```

4. Agarose Gel Electrophoresis

10 μl of each PCR product was resolved in 1% agarose gels with TAE electrophoresis buffer (40 mM Tris-acetate and 1 mM EDTA, pH 8.0). Electrophoresis was carried out at 100V for 1.5 hours and the fragments were visualized under UV.

5. DNA Sequencing Protocol

The PCR products were loaded onto a 1% (w/v) low-melting point agarose gel and extracted by the freeze-thaw method (Shoemaker and Salyers, 1990). They were then cloned into the pGEM-T vector (Promega). The clones were sequenced using the ABI PRISM Dye terminator cycle sequencing kit (Perkin Elmer) on the 373 DNA sequencer from Applied Biosystems. Multiple sequence alignment using the cluster method was carried out with the DNAS-TAR programme.

6. Results 6.1 Detection of *P. berghei* Infection in Blood Spots

Figure 6A:
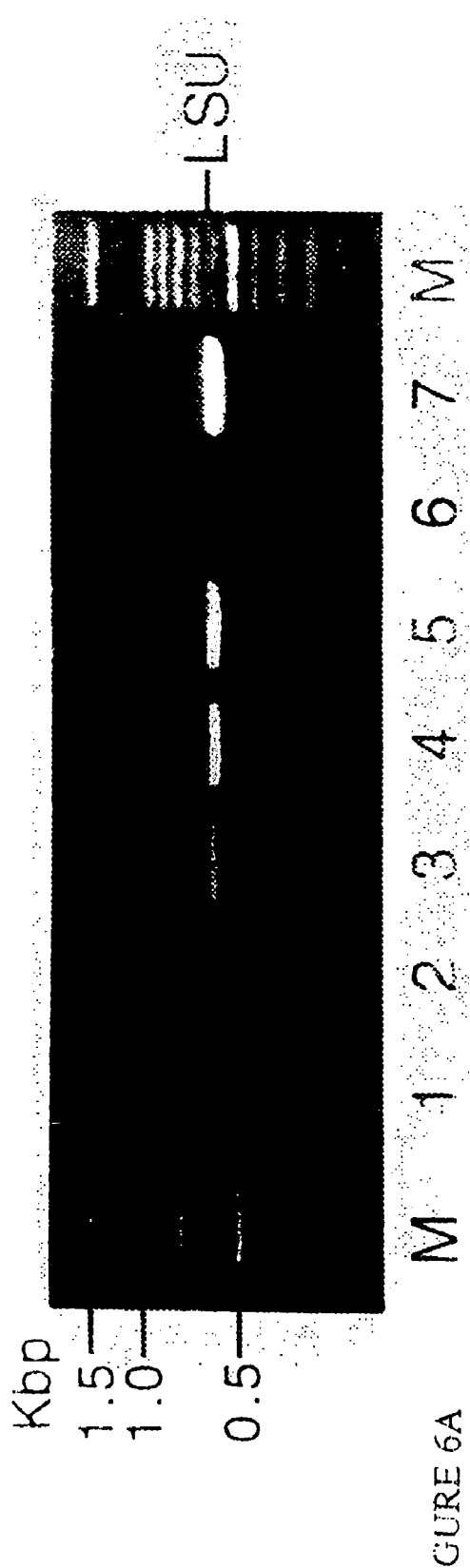
FIG. 6 is a copy of a photographic representation showing PCR amplification products generated using the primer set L1/L2 (SEQ ID NO: 5/SEQ ID NO: 6) (Panel a), and the primer set DHFR1/DHFR2 (Panel b). Blood was drawn daily for 5 days from a mouse initially infected with $5 \times 10^4$ parasites. Lanes 1-5 in both panels show the amplification products obtained from blood spots 1 to 5 days post-infection correspondingly. Lane 6 is the negative control with blood from an uninfected mouse and lane 7 is the positive control using 50 ng of purified *P. berghei* total DNA as template. M indicates the 100 bp DNA ladder (Promega) used as markers.
Figure 6B:
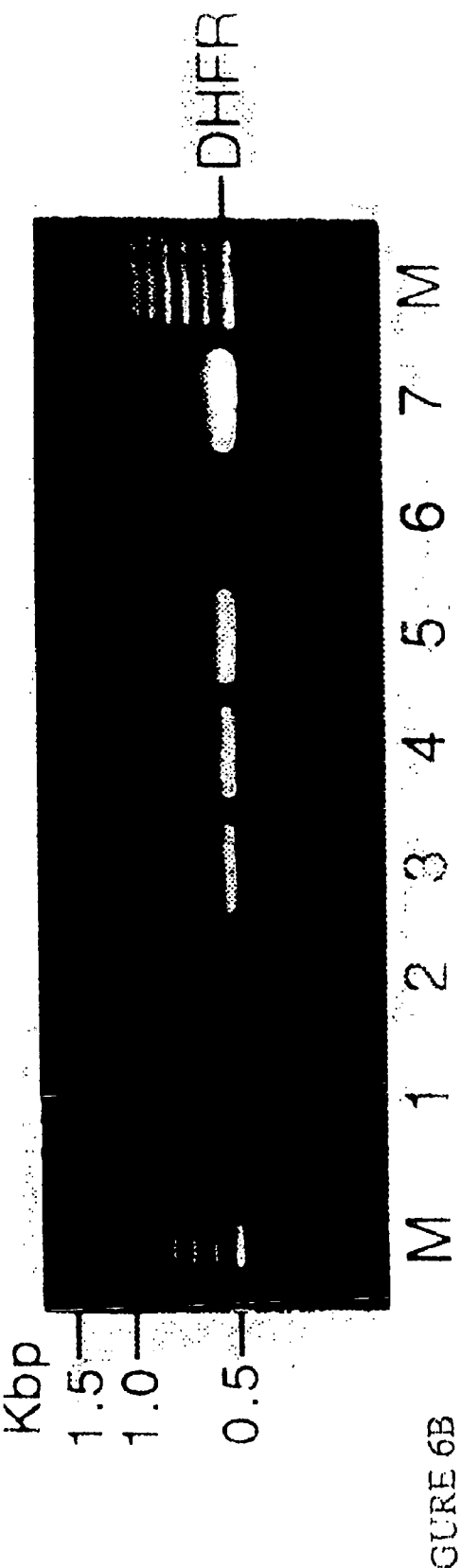

Conditions for the PCR amplification of *P. berghei* infected mouse blood spotted on filter paper were optimised using DHFR1 and DHFR2 primers. Once these conditions were established, the sensitivity of the LSU-rRNA primer set was compared with that of the DHFR-TS primer set. The LSU-rRNA primer set was designed to amplify a 594 bp fragment from the *P. berghei* circular DNA while the DHFR-TS primer set amplified a 511 bp fragment from *P. berghei* genomic DNA. Blood spots were prepared daily for 5 days from a mouse which was initially infected with $5 \times 10^4$ parasites. Giemsa staining of thin blood films from the same animal was done daily. The LSU-rRNA primer set was more sensitive than the DHFR-TS primer set in detecting parasite DNA. The amplified LSU-rRNA fragment was detectable by ethidium bromide staining one day after infection (FIG. 6*a*) while the DHFR-TS PCR product was only visible two days post-infection (FIG. 6*b*). At these two time points, no parasite was detected on the corresponding Giemsa-stained blood films. Parasites were only observed on the film three days post-infection.

6.2 PCR Amplification of Blood Spots from Malaria Infected Patients.

Figure 7:
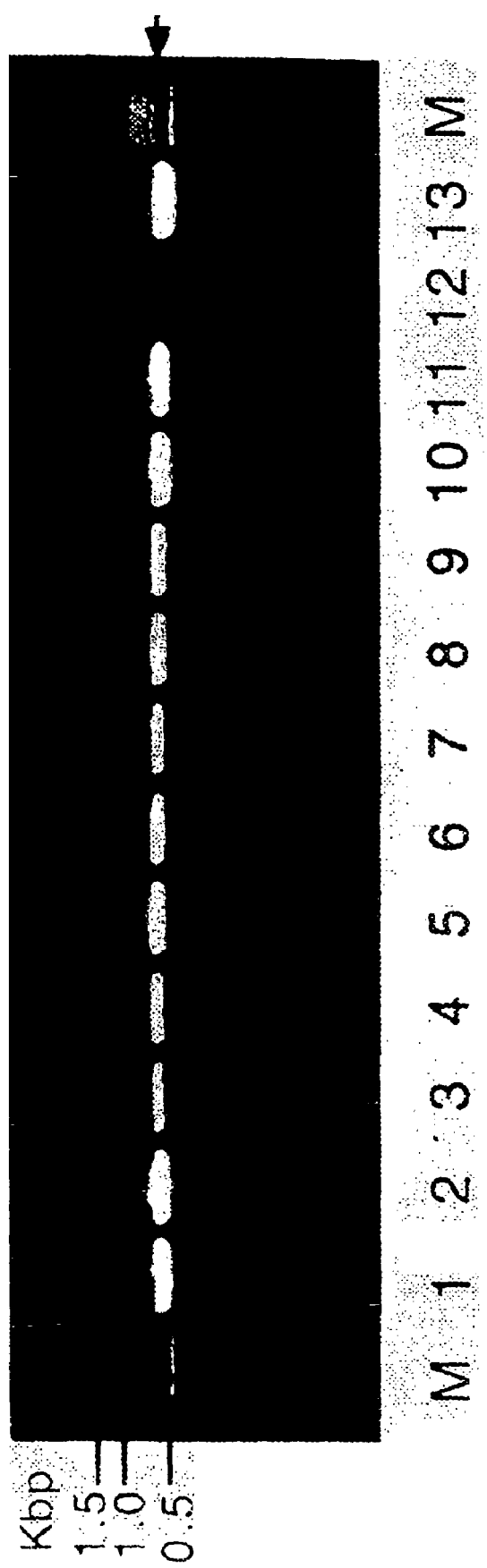
FIG. 7 is a copy of a photographic representation showing PCR amplification of blood spots from Laotian patients diagnosed positive for *P. falciparum* malaria by Giemsa microscopy and ParaF dipstick, with the exception of one which was infected with *P. vivax* (lane 11). Primers used were the L1/L2 primer set (i.e. SEQ ID NO: 5/SEQ ID NO: 6). Lane 12 is the negative control with a blood spot from a healthy person and lane 13 is the positive control using 50 ng of purified *P. falciparum* (FC27 strain) total DNA as template. M indicates the 100 bp DNA ladder (Promega) used as markers. The arrow indicates the position of amplified LSU DNA.
Figure 8:
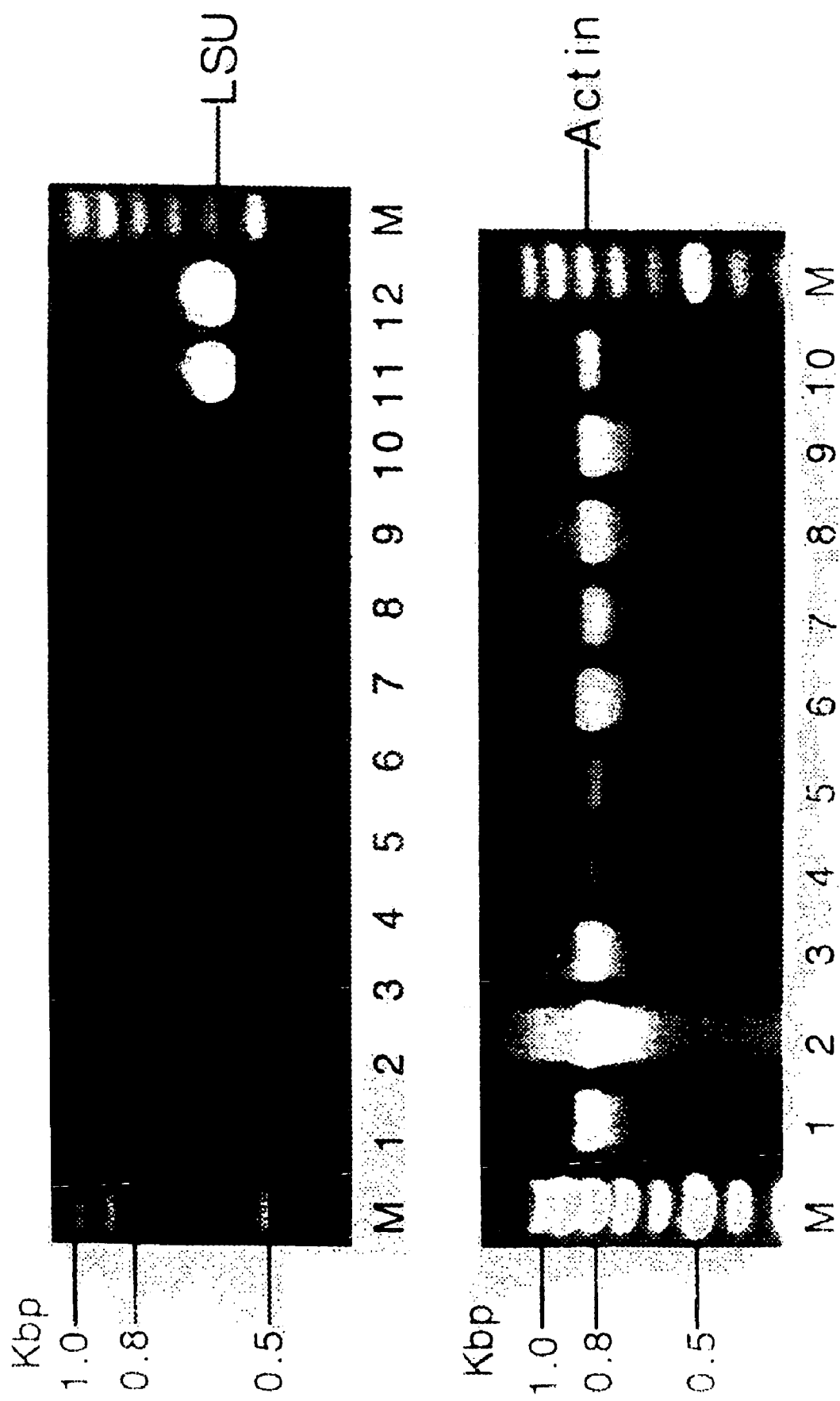
FIG. 8 is a copy of a photographic representation showing PCR amplification of blood spots from uninfected persons using the L1/L2 (SEQ ID NO: 5/SEQ ID NO: 6) primer set (Top Panel) and AC1/AC2 primer set (Lower Panel). Lanes 1 and 2 in both top and lower panels are positive controls for human β-actin using 50 ng of purified total DNA from CaSki and HeLa cells. Lanes 3-10 in both top and lower panels use blood spots from uninfected persons as the template. Lanes 11 and 12 in the lower panel use blood spots from a *P. falciparum*-infected patient and a *P. vivax*-infected patient respectively. M indicates the 100 bp DNA ladder (Promega) used as markers.

The above PCR amplification protocol was also applied to blood spots from 31 malaria-infected patients. 15 of these samples were obtained from patients admitted to the National University Hospital in Singapore. Of these, 7 had *P. falciparum* infection, 1 had *P. malariae* and the remaining had *P. vivax* as determined by Giemsa and Quantitative Buffy Coat (QBC) diagnosis. All samples were positive for amplification with LSU primers (data not shown). The other 16 samples were from patients in Laos with 15 *P. falciparum* infections and one *P. vivax* malaria infection as determined by Giemsa diagnosis. LSU-rRNA PCR amplifications were positive for all 16 specimens. As shown in FIG. 7, the PCR products from 11 of the 16 Laotian specimens. Eight healthy persons and total DNA from two human carcinoma cell lines, CaSki and HeLa were used as controls. These were all negative when using the LSU-rRNA primer set for PCR amplification but were all positive for human β-actin (FIG. 8, compare panels a and b).

EXAMPLE 9

Sequence Alignment of LSU-rRNA Extrachromosomal DNA from Various *Plasmodium* Species The LSU-rRNA fragments amplified from the blood spots as described in Example 8 were cloned into the pGEM-T vector and sequenced. In addition to amplified products from the Singaporean and Laotian patients, we also amplified and sequenced LSU-rRNA fragments from Indian, Colombian and Pakistani patients. The published *P. falciparum* sequence (C10 strain) was used as the basis for all alignments and comparisons.

Comparison of the *Plasmodium* species used in this study showed that this region of the LSU-rRNA gene is highly conserved and the similarity between *P. falciparum*, *P. vivax*, *P. malariae*, *P. ovale* and *P. berghei* is greater than 91% (Table 5). The similarity between the C10 and other *P. falciparum* sequences ranged from 98.3%-99.8%, while that between the C10 and the *P. vivax* sequences ranged from 91.1-99.7%. The greatest divergence in sequence was observed from the *P. vivax* specimens from Pakistan and Colombia. In all cases, divergence in sequence was due to 1 or 2 base changes in isolated regions within the LSU-rRNA fragment (FIG. 9).

TABLE 5

Percent homology of LSU-rRNA sequences with *P. falciparum* (C10 strain) sequence

| Name of sequence[1] | Similarity Index to Pf(C10)[2] |
|---|---|
| Pf10/P | 98.3 |
| Pf11/P | 98.5 |
| Pf19/I | 99.7 |
| Pf20/L | 99.7 |
| Pf18/S | 99.8 |
| Pv12/P | 93.4 |
| Pv13/P | 92.9 |
| Pv15/I | 99.5 |
| Pv16/L | 99.7 |
| Pv17/S | 93.4 |
| Pv86/C | 91.1 |
| Pm1/S | 93.2 |
| Pm38/S | 92.9 |
| Po35/S | 93.4 |
| Po36/S | 93.2 |
| Pb(ANKA) | 94.2 |

[1]Pf denotes *P. falciparum*, Pv denotes *P. vivax*, Pm denotes *P. malariae* and Pb denotes *P. berghei*. The alphabet at the end of each name indicates the origin of the specimen; P = Pakistan, I = India, L—Laos, C = Colombian and S = Singapore. The GenBank accession numbers for Pf(C10) and Pb(ANKA) are X95275 and U79731 respectively.
[2]Similarity index obtained using the Martinez-Needleman-Wunsch DNA alignment programme.

EXAMPLE 10

Discussion

In this study, we have shown that it is possible to amplify the extrachromosomal circular plastid-like DNA found in *Plasmodium* ssp. This has allowed us to proceed with characterising the LSU-rRNA gene from the circular DNA of malaria-infected patients using only a small volume of blood spotted on filter paper.

We have designed a pair of primers based on the sequences from *P. falciparum* and *P. berghei* such that the primers are completely homologous for both species. Using these primers, we have been able to amplify the corresponding LSU-rRNA fragment from *P. falciparum*, *P. vivax*, *P. malariae* and *P. berghei* infected blood. Sequence analysis of these fragments indicates that this region of the LSU-rRNA is highly conserved between different species of *Plasmodium*. In addition, different geographic isolates of *P. falciparum* and *P. vivax* from Asia do not show distinct variations for the LSU-rRNA fragment. GenBank searches indicate that this fragment sequence is unique.

The high homology between the various *Plasmodium* species has led us to examine if the LSU-rRNA specific primers are useful for the detection of malaria infections. Using *P. berghei*, the LSU-rRNA primer set was shown to be more sensitive than the DHFR primer set in parasite detection in mouse blood spots. All 31 patient blood spots tested were positive regardless of the *Plasmodium* species involved while none from healthy persons was positive. These results indicate that the LSU-rRNA primers may be useful for the diagnosis of malaria infection.

The ease of direct PCR amplification of extrachromosomal *Plasmodium* circular DNA from dried blood spots has provided us with the means to study and characterise the genes present on this DNA molecule. To date, none of the genes on the circular DNA of *P. vivax* and *P. malariae* has been described. This is the first description of an analysis of the LSU-rRNA gene from different field isolates of *P. ovale, P. vivax, P. malariae* and *P. falciparum*. More investigations are being carried out to determine the extent of sequence conservation and arrangement of the genes on the circular DNA from different *Plasmodium* species.

EXAMPLE 11

PCR Amplification and Sequence Analysis of Cox I Gene

To obtain the complete sequence of the mitochondrial cox I gene, a set of primers was designed based on the published *P. falciparum* sequence (GenBank accession number M76611). PCR using this primer set with blood spots from *P. vivax* infected patients resulted in fragments of 1.5 kb in size (FIG. 10). These were cloned into pGEM-T vector (Promega). The clones were sequenced in both directions using the ABI PRISM dye terminator cycle sequencing kit on the 374 DNA sequencer from Applied Biosystems. DNA sequence alignments were carried out using the Martinez/Needleman-Wunsch DNA alignment. The DNA sequences from 4 different *P. vivax* isolates were highly conserved (greater than 99% similarity). However, these sequences were less homologous (83%) when compared with the corresponding cox I gene from *P. falciparum*.

EXAMPLE 12

*Plasmodium* Species Identification in Blood Samples

In order to differentiate between *P. vivax* and *P. falciparum* infection, two sets of *P. vivax* specific primers (PV1-SEQ ID No: 12 and P2-SEQ ID No: 11; PV2-SEQ ID No: 13 and P3-SEQ ID No. 14) and four sets of *P. falciparum* specific primers (PF1-SEQ ID No: 15 and P2-SEQ ID NO 11; PF2-SEQ ID No: 16 and P2-SEQ ID No: 11; PF3-SEQ ID No: 17 and P2-SEQ ID NO 11; PF2-SEQ ID No: 16 and P4-SEQ ID No: 18) were designed based on the mitochondrial cox I genes of the two species. PCR assays were carried out on whole patient's blood spotted onto a filter disc as described for Example 7. The PCR products were analysed by agarose gel electrophoresis.

The results are shown in Tables 6, 7, 8 and 9. The three sets of *P. falciparum* specific primers only detected *P. falciparum* infected blood but not the other three human *Plasmodium* species. The *P. vivax* specific primers (PV1/P2) detected only 92% of the *P. vivax* infected blood and a false positive with *P. malariae* was also observed. This primer set does not react with *P. falciparum* or *P. ovale* (Table 6).

TABLE 6

Results using Plasmodium species specific primer set PF1/P2 and PV1/P2

| Species | *P. falciparum* primer set I (PF1/P2) | *P. vivax* primer set I (PV1/P2) |
|---|---|---|
| *P. fal* | 12/12 | 0/12 |
| *P. viv* | 0/26 | 24/26 |
| *P. mal* | 0/2 | 1/2 |
| *P. ova* | 0/2 | 0/2 |
| Pm/Pf | 1/1 | 0/1 |
| Pv/Pf | 2/2 | 2/2 |
| Controls | 0/7 | 0/7 |

TABLE 7

Results using Plasmodium species specific primer set PF2/P2

| Species | *P. falciparum* primer set II (PF2/P2) |
|---|---|
| *P. fal* | 6/6 |
| *P. viv* | 0/14 |
| *P. mal* | 0/2 |
| *P. ova* | 0/2 |
| Controls | 0/7 |

TABLE 8

Results using Plasmodium species specific primer set PF3/P2

| Species | *P. falciparum* primer set III (PF3/P2) |
|---|---|
| *P. fal* | 9/9 |
| *P. viv* | 0/12 |
| *P. mal* | 0/2 |
| *P. ova* | 0/2 |
| Controls | 0/7 |

TABLE 9

Results using Plasmodium species specific primer sets PF2/P4 and PV2/P3

| Species | *P. falciparum* primer set IV (PF2/P4) | *P. vivax* primer set II (PV2/P3) |
|---|---|---|
| *P. fal* | 20/20 | 0/20 |
| *P. viv* | 0/31 | 31/31 |
| Pv/Pf | 3/3 | 3/3 |
| Pm/Pf | 2/2 | 0/2 |
| Pv/Po | 0/3 | 3/3 |
| Controls | 0/10 | 0/10 |

EXAMPLE 13

Sensitivity of PCR Assay for *Plasmodium* Species in Blood Samples

The minimum number of parasites detectable by PCR assay was determined by using 1 μl of whole patient blood or diluted blood spotted on filter disc. Using the L/L (SEQ ID NOS 5 and 6), the minimum number of parasite detected is 4 (FIG. 11).

EQUIVALENTS

Those skilled in the art will appreciate that the invention described herein is susceptible to variations and modifications other than those specifically described. The invention also includes all of the steps, features, composition and compounds referred to or indicated in this specification, individually or collectively, and any and all combinations of any two or more of said steps or features.

REFERENCES

1. Ausubel, F. M., Brent, R., Kingston, R E, Moore, D. D., Seidman, J. G., Smith, J. A., and Struhl, K. (1987). In: Current Protocols in Molecular Biology. Wiley Interscience (ISBN 047150338).
2. Dore, E., Frontali, C., Forte, T. and Fratarcangeli, S.: Mol. Biochem. Parasitol. 8 (1983) 339-352.
3. Egea, N. and Lang-Unnasch, N.: Euk. Microbiol. 42 (1995) 679-684.
4. Feagin, J. E., Werner, E., Gardner, M. J., Williamson, D. H. and Wilson, R. J. M.: Nucleic Acids Res. 20 (1992a) 879-887.
5. Feagin, J. E. and Drew, M. E.: Experimental Parasitol. 80 (1995) 430-440.
6. Flores, M. V., Stewart, T. S. and O'Sullivan, W. J.: Int. J. Parasitol. 21 (1991) 605-608.
7. Gardner, M. J., Bates, P. A., Ling, I. T., Moore, D. J., McCready, S., Gunasekera, M. B. R., Wilson, R. J. M. and Williamson, D. H. Mol. Biochem. Parasitol. (1988) 31, 11-18.
8. Gardner, M. J., Williamson, D. H. and Wilson, R. J. M.: Mol. Biochem. Parasitol. 44 (1991) 115-124.
9. Gardner, M. J., Feagin, J. E., Moore, D. J., Rangachari, K., Williamson, D. H. and Wilson, R. J. M.: Nucleic Acids Res. 21 (1993) 1067-1071.
10. Gardner, M. J., Goldman, N., Barnett, P., Moore, P. W., Rangachari, K., Strath, M., Williamson, D. H. and Wilson, R. J. Mol. Biochem. Parasitol. 66 (1994) 221-231.
11. Gozar, M. M. G. and Bagnara, A. S. Int. J. Parasitol. 23 (1993) 145-148.
12. Gozar, M. M. G. and Bagnara, A. S. Int. J. Parasitol. 25 (1995) 929-938.
13. Howe C. J. J. Theor. Biol. 158 (1992) 199-205.
14. Kilejian, A. Biochem. Biophys. Acta 390, 276-284.
15. Long, G. W., Fries, L., Watt, G. H. and Hoffman, S. L. Am. J. Trop. Med. Hyg. 52, (1995) 344-346.
16. McPherson, M. J., Quirke, P. and Taylor, G. R. (1991) In: PCR A Practical Approach. IRL Press at Oxford University Press, Oxford. (ISBN 019963226).
17. Preiser, P., Williamson, D. H. and Wilson, R. J. M. Nucleic Acids Res. 23 (1995) 4329 4336.
18. Reinhartz, A., Alajem, S., Samson, A. and Herzberg, M. Gene 136 (1993), 221-226.
19. Sehgal, D., Mittal, X T, Kamachandran, S., Dhar, S. K., Bhattacharya, A. and Bhattacharya, S. Mol. Biochem. Parasitol. 67 (1994) 205-214.
20. Shoemaker, N. B. and Salyers, A. A. J. Bacteriol. 172 (1990), 1694-1702.
21. Shute, G. T. (1988) In: Principles and practice of malariology (Wernsdorfer, W. H. and McGregor, I. eds) pp 781-814.
22. Suplick K., Akella, R., Saul, A. and Vaidya, A. B. Mol. Biochem. Parasitol. 30 (1988) 289-290.
23. Suplick, K., Morrisey, J. and Vaidya, A. B. Mol. Cell. Biol. 10 (1990) 6381-6388.
24. Vaidya, A. B. and Araus, P. Mol. Biol. Parasitol. 22 (1987) 249-257.
25. Wardlaw, S. C. et al JAMA 249 (1983) 617-620.
26. Williamson, D. H., Gardner, M. J., Preiser, P., Moore, D. J., Rangachari, K. and Wilson; R. J. Mol. Gen. Genet. 243 (1994) 249-252.
27. Williamson, D. H., Wilson, R. J. M., Bates, P. A., McCready, S., Perler, F. and Qiang, B. Mol. Biochem. Parasitol. 14 (1985) 199-209.
28. Wilson, R. J. M., Gardner, M. J., Feagin, J. E. and Williamson, D. H., Parasitology Today. 7 (1991) 134-136.
29. Wilson, R. J. M., Denny, P. W., Presier, P. R., Rangachari, K., Roberts, K., Roy, A., Whyte, A., Strath, M., Moore, D. J. Moore, P. W. and Williamson, D. H. J. Mol. Biol. 261 (1996), 155-172.

What is claimed is:

1. A method of detecting presence or absence of a *Plasmodium* malarial agent of humans in a biological sample in which the presence or absence of a *Plasmodium* malarial agent of humans is unknown, said method comprising the steps of:

(a) providing a biological sample, wherein the presence or absence of a *Plasmodium* malarial agent of humans in the biological sample is unknown and wherein the biological sample is from a human or animal which can be infected with a *Plasmodium* malarial agent of humans, (b) contacting a nucleic acid probe or primer which hybridizes specifically to the *Plasmodium berghei* extrachromosomal genetic element with said biological sample or contacting the probe or primer with a nucleic acid extracted, purified or amplified from said biological sample, for a time and under conditions sufficient for specific hybridization to occur between the probe or primer and the nucleic acid or sample, wherein the probe or primer consists of nucleotides 1147 to 1740 of SEQ ID NO:1 or of 15 or more consecutive nucleotides thereof, or wherein the probe or primer consists of a nucleotide sequence complementary to nucleotides 1147 to 1740 of SEQ ID NO:1 or 15 or more consecutive nucleotides thereof; and (c) detecting said hybridization resulting from the contacting step (b), whereby a *Plasmodium* malarial agent of humans is detected in a biological sample when hybridization of the probe or primer to the sample or to a nucleic acid extracted, purified or amplified from said biological sample is detected and whereby absence of a *Plasmodium* malarial agent of humans is detected when hybridization is not detected.

2. The method according to claim 1, wherein the probe or primer comprises a nucleotide sequence set forth in SEQ ID No. 5.

3. The method according to claim 1, wherein the probe or primer comprises a nucleotide sequence set forth in SEQ ID No. 6.

4. The method according to claim 1, wherein the detection means comprises a polymerase chain reaction (PCR) format using one or more probe or primer or primer pairs.

5. The method according to claim 4, wherein the primer pair comprises nucleotide sequences set forth in SEQ ID Nos. 5 and 6.

6. The method according to claim 1, wherein the contacting step is performed under low stringency hybridization conditions.

7. The method according to claim 1, wherein the contacting step is performed under moderate stringency hybridization conditions.

8. The method according to claim 1, wherein the contacting step is performed under high stringency hybridization conditions.

9. The method according to claim 1, wherein the detecting comprises identifying a signal produced by a reporter molecule bound to the probe or primer, wherein the reporter molecule produces an identifiable signal.

10. The method according to claim 9, wherein the reporter molecule is a radioisotope or a non-isotopic reporter molecule.

11. The method according to claim 10, wherein the non-isotopic reporter molecule is biotin.

12. The method according to claim 1, wherein the detecting comprises a polymerase chain reaction (PCR).

13. The method according to claim 12, wherein the PCR is reverse transcriptase-PCR.

14. The method according to claim 1, wherein the *Plasmodium* malarial agent of humans is selected from the group consisting of *Plasmodium falciparum, Plasmodium vivax, Plasmodium ovale* and *Plasmodium malariae*.

15. The method according to claim 1, wherein the biological sample comprises blood or nucleic acid extracted, purified or amplified from said blood.

16. The method according to claim 15, wherein said blood is human blood.

17. The method according to claim 15, wherein said biological sample comprises dried blood.

* * * * *

UNITED STATES PATENT AND TRADEMARK OFFICE
CERTIFICATE OF CORRECTION

PATENT NO. : 7,303,883 B2 Page 1 of 1
APPLICATION NO. : 11/270287
DATED : December 4, 2007
INVENTOR(S) : Anna Kate Ursula Kara et al.

It is certified that error appears in the above-identified patent and that said Letters Patent is hereby corrected as shown below:

Title page:
Item (75), Inventors:
Delete "Jill Maelon Tham" and replace with --Jill Maelan Tham--.

Signed and Sealed this

Twentieth Day of May, 2008

JON W. DUDAS
*Director of the United States Patent and Trademark Office*

UNITED STATES PATENT AND TRADEMARK OFFICE
CERTIFICATE OF CORRECTION

PATENT NO. : 7,303,883 B2 Page 1 of 1
APPLICATION NO. : 11/270287
DATED : December 4, 2007
INVENTOR(S) : Anna Kate Ursula Kara et al.

It is certified that error appears in the above-identified patent and that said Letters Patent is hereby corrected as shown below:

Title page
Item (30), Foreign Application Priority Data:
Delete "Feb. 5, 1997 (WO) PCT/IB98/00212" and replace with --Feb. 5, 1998 (WO) PCT/IB9800212--.

Signed and Sealed this

Fifth Day of January, 2010

David J. Kappos
*Director of the United States Patent and Trademark Office*

SEQUENCE LISTING

```
<160> NUMBER OF SEQ ID NOS: 53

<210> SEQ ID NO 1
<211> LENGTH: 5849
<212> TYPE: DNA
<213> ORGANISM: Plasmodium berghei

<400> SEQUENCE: 1
taatgaagct gtacatcctt ctaaatatcc aacatatgca aattcacttg ctattaataa      60
agtacgttca aattgtgcaa aatcataaga attagtctta aaataagttg ataaattaaa     120
actacatttt atatacttag acacataaca aaaagatcct tcactaaaaa taattgaatt     180
aatatttgca aaaaaattat ctttataaga aactacagtt cctaaatatt tttttactaa     240 taaggatat tttaaaataa cgtccaataa agacaaaaat ataataccta attttttaa      300 aaaatattgt gttgtatgta aaacagatat actatcacaa ataacatcaa taggaattat     360 tttttttatta aaataggtat ctaaaaaatt tatatttaaa ttagttttta aatatactaa     420
caaattacta tcttttaaag tagaagaata ataaataata ttatcataac taatattggg     480
acattcgaaa cacgaccaat ctggtaattt aaacatattt aaaaatttta aagaatatat     540
```

```
tttaaatttg taaataaaaa aatataaata aatattatta gataaatttt ttatcaaatt      600
tttatttaat ccatttctta ttaaatataa atttatttta ttattatatt gatatttata      660
atttaaatta taaatattta aaaattttt taatttaat ttatttatca taataatttt      720
atattataaa atatttcaag ttaacgatga gatttgaact cacaatctac tgattacaaa      780
tcagttgctt taccaattaa gccactttaa caaatatatt atttataatt aaatattcaa      840
cttattagga attatacaca aaatatatta ctataaatac atattaattc tataaaataa      900
tttttctaat tattgtttta ttcatttata tgattagaat attatttta attaaatttt      960 cttatttata ttacttcaac aattaaaatt ttatacttaa ctactcaaca ttacaaaata     1020
taataattga tatatcattg gtataatttt ttcgatcctc tcgtactaga aaaaataatt     1080
tcaatattct aacacttata ttagatatgg accgaactgt ctcacgacgt tctgaaccca     1140
gctcacgtat cgctttaata ggcgaacaga cttacccctta aaacatacta ctgccttagg    1200
atgcgataag ccgacatcga ggtgccaaac cttttcgtca atatggactc tcggaaagaa     1260
ttagcctgtt atccctagag taacttttat ccgttaagcg ataatttat tattaaataa      1320 ttatcggatc attaagaccg acattaatct ctgtttaatt tgtaaatttt acagttaatt     1380
atatatttat ctttatataa taaatataac attgtacacc tccgttttta tataggagga     1440
gaccgcccca gtcaaactat cttataaata ttgttaaaaa ttttgttata aaaattttat     1500
aagaatttat atatatataa aatggtattt cattaacaat tacattattt ccaaaaaaat    1560
aatattacta cttcccattt attctatgtt atatatatat atttttcaata tctattaata   1620 gtaaagcttc ataggtctt tctgtcctaa tataagaaat ctgcatcttc acagataatt     1680
ttatttcatt aagatttttt ttaagacagc atttaagtcg ttacatcttt catgcaggtc     1740
ggaacttacc cgacaaggaa tttcgctacc tttggaccgt tatagataca gccgccgttt    1800
actatagctt atatatatat tataattta aattataat attattttta cataatagca     1860
ctgggcagat gtcaatcttt atacatcatc tttcgattta gcaaagattt gtgttttgt     1920 taaacagtcg cttaaattt ttgttttcaa ctaaataagt atctcttctc ccctaagttt     1980
acgagataaa tttgccgagt tccttaaaaa aaattatctc aacttcttaa taatttatat    2040 atattacta gtgtcagttt acagtacgaa tacataataa tatatatata taaataatttt    2100 ttatataata taatatatt attattatat tagttttaaa atataaatat tattatatag    2160
tataagaata ttaacttatt acctatcgat tacacattac atctcatctc aagatacgac    2220
taaccctatt taaaataata ataaatagga gcccttaaat tatagaagta ttggattttt    2280
accaatattt acattactca aattagcatt atcacttttg atataattat tttaactttt    2340
catataaata atttatattc aaaacgctct tttaccaatt taatttatt aatattaaat    2400 tttatacata tcgataatta atttatttc gattatttct gaactaaaat tactaaatta    2460
atgagctttt acgcactctt taaaagataa ctgcttctaa atttactttt taattattta    2520
aataatttta tattcttttt aagacttaat taatatttaa aaatcttaat ttataattcg    2580
ggctgtttcc cttttgaaaa taaagcttat cctttatttt ctgatcatat atatatttta    2640
ttaaataaaa ttcttaaatt attttcatta atattaacta tataaattaa tttaataaaa    2700
aaagagtttt acatttattt atatataaat actatactta catatatttc aaagagaacc    2760
agctatcttc aaattcgatt ggcatttcac ctctaattat actttatttg atacttttgc    2820
aacagtaacc aattcaaact tcaatttaat tttatttaaa tcttatttta aatataatta    2880
```

```
gatcatttga tttcgggtct ataataaata atatactaaa tgcttattat atataataac    2940
aaactcgagt atactttggc ttcatttata aatatttaac ctaataatta tactatttat    3000
tataacttgc taattctttc ttcaacaaga aaataataaa attatattaa attttattat    3060
tatttattaa atttaaaatt caggttctt  tcactatttt ctcaaaatcc ttttcatctt    3120
tccctcacgg tactattcac tatcaacttt tattatatta aattttataa gataactctt    3180
aattatattt atattattca tataaaatat attttatat  tacttaatta aaattttaca    3240
tatataatgt tttaaatctt tcagttcgct cgccactact atgaaaatcg ttattacttt    3300
atattccttt aagtactaag atgattcagt tccttaagtt tttttaaaat atttatataa    3360
aaataaattt ttattcagat acttttataa ttttaataat aaaaaatttt aaatatattt    3420
aattttttat aattataaaa atttcgttaa tatatttaac gtctttcttc aataataaaa    3480
ataatagaca tccttttaaa tttattatat atatttaatt atatatttaa ctatataaat    3540
tataaattaa tttatttaaa ataagcgaaa aacggaattg aaccgattac cttcggagca    3600
tgaatccgac gaactttcct tatgctctat ttcgctaaat acaattaaac ttgaaaagaa    3660
ttgaactttt attttataat tcgtactat  atattttatc cattaaatta caagttcatt    3720
atattataat atataaatta taagtaatta acttagaggt aaagtttctg ctttacatac    3780
agaagatcat tggttcgatt ccaatattac ttaaataaat ctataattta atggataaaa    3840
taaaaacctt ctaagtttta tatgtaagtt caaatcttac tagatttaat aataatgaat    3900
atggcgaaaa ggtaaacgcg ctaaatttag aatttagttt ttataataat aagagttcga    3960
atctctttat tcatatttat aatatacttc ttaaactagg attgaactag tatctttcgg    4020
ttaacagccg aatgctttaa ccactaagct attaagaata ttaatattat attatataat    4080
atataatagg gaatatagtt taatggtaaa atcttattct tgcataataa agatagtagt    4140
tcaattctac ttatttccat attataaaat ctataaatgt tataatttt  aaataatata    4200 tatataatta tattgcgagt ttgatcctag ctcagaatga acgctagaaa tatacattac    4260
acatgcaaat ttatggatta tatcatagtg aataggtgag gatatataaa ttttaatt     4320 taaatagatt ataatatata ataatctata agcgcattta tttatataat tgtactatat    4380
taaaaattat tattgtttaa aataaaattt atatttgatt aactagttgg taaaataaaa    4440
gcctaccaag gttatgatca aaaattggtt ttaaagaatg tacaatcaca ttagggattg    4500
aaataaagcc ctaaattttt tttaaatcag cagtgaggaa tattttacaa tgagcgtaag    4560
cttgataaag taatatttct taaaggatga cagtatattt ttatattgta aactttatat    4620 tttatttta  aatattgata aaataaaac  attagtattt gctaatttct gtgccagcag    4680
cagcggtaat acagaaaata ccagcgttat tcactttatt tggcgtaaag cgttttaagg    4740
ttttatatta atttttatttt aaaatattta atttaaattt gaataaaaaa taaataataa    4800
tataataaga gtattataaa agtattaaga attttttgag aagtagtgaa atgcaatgat    4860
acaaaaaaga ataccaaagg cgaaggcata atactatata ataactgaca cttataaacg    4920
aaagctaagg tagcaaatag gattagatac cctagtagtc ttagctgtaa actatgaata    4980
ttttatattt atatattaat ataaatataa taactaacgt aataaatatt ccgcctgagt    5040
agtatattcg caagaacgaa attcaaagga attgacggga gcttatacaa gtggtggaac    5100
atgtggctta attcgatgca acacgataaa ccttaccaaa atttaacaat attttttatta    5160 ttaaggaatt aatagtttaa taaaatatat aggtagtgca tggctgtcgt cagttcgtgc    5220
tgtgaagtat taatttaagt attataacga acgtaaccct tttataaaaa aatttttta    5280
```

```
taatatattt attaaatata taaaaaagac tacgtcaagt cattatgctc cttatatttt    5340
gggctgctca cgtgttacat aaaatataac aatattttat tatatgaaaa tataatatat    5400
taaatatatt tatagttctg attataaatt gaaactcatt tatatgaaga tggaatcact    5460
agtaatcgct aataagaagt atagcggtga ataagttctt aagctttgta cacaccgccc    5520
gtcacatctg gaaatatta tattatataa aaattattgt aaaataataa tatataatta    5580
tataatttag atgaagtcgt aacaaggtag ccgtactgga aggtgcggct ggataataac    5640
ataaaatttt ggttgaatta tttatttaaa aataatattt atatataaaa gtaattataa    5700
ttatataatt tttatagaca aaaatagcat taatacacat taatgtaaat ttagttaaat    5760
attattttat atatataaag gttttttagtt taatggtaaa acatactctt gataagggta    5820
agactttagt tcaattctaa aataaccta                                      5849

<210> SEQ ID NO 2
<211> LENGTH: 1711
<212> TYPE: DNA
<213> ORGANISM: Plasmodium berghei

<400> SEQUENCE: 2
ttcagaaaaa taggatttga acctatattc ttctattccc aaaatagata tgttaccatt      60
acactatatt ctgaatattt aaaattttat acttttaagg aaaatcgaat tcctattttc     120
ttcttgaaaa aaagatgtct tacctttaaa cgataaaagt aaaaacttaa attacctgag     180
acttgaactc agaaccattc gattaaaagt cgagtactct accaattaag ctagtaattc     240
ttaatataac gaatctgacg agaattgaac tcgtattctt tgttatgaca aaataatatt     300
ttaacctaat taaactacaa attcaaataa atatatatag ggaaaaggga ttcgaaccct     360
ggtatatata atatctacat aaatgtagca atttatagct ataaccactc agccatttct     420
gtatataata ataagttaaa tcagattgaa ctgatgtaga tataaaaccc aatggattta     480
cagtccatcc cttttaaccc ctcaggcatt aactttatta tacatttaag tagattcgaa     540
ctactgatgt tcaatatttg aaaatgaatt atgagtccat tgctttcgac ctcttagcta     600
taaatgttta ctttattaga gataaaggga ctcgaaccct tacaacaatt attgttaatg     660
gattttctaa ttgaaattta gacttttttat aaacatgtat ataaataata aagtcgtttg     720
aatatataac taatatatta cagaataaaa attatttttt ctttatatat atttaaatta     780
ttaatttatt tataaaatta actcataaac aacgaatata aattatatttt atattattta     840 aagtccattg tgtataccaa atttcaccat atctctatta tatactatat aaatgatatt     900
cagatttgaa ctgaaataaa ataatttgca attatccact ttacctaatt aagttatatc     960
attattatat attataagat aaataaagag atttgaactc atataaaaga aaccacaatt    1020
ccttatctta acctttagga ttatatttat cattattaaa acttattata tattataaat    1080
attattataa atatataaaa tattatttaa atataaatca tttaatatttt ttattttaaa    1140 attatatata catataataa aattatcatt aaaactagaa gatttaataa aattatatttt   1200 ataaaattt gatatataaa tatatatatt atatctataa attaaatttg gtgaaattat    1260
atatttaatt ttttttattaa aaaaaattat atccttaccc tttaatttaa tattataata    1320
attaccataa accttatttta aatatacata tttataccttt atataaatatc tcagagtggt    1380 gtatagttttt aaaaccccca tattaactaa aaagacatct aatctaggtt ctaatagatt    1440 taataattttg agatataaat gattctcatg gtgactctgt atttttttca aataatgtaa    1500
```

```
atatggttta aatgttatac cataattata acagatatat cttacaaatt ttaattttaa      1560
atcgaaataa gattgataga catatttatt aatttttaat ttataattat atttactaga      1620
taaatataat aaaaaaggaa gatttaattt ttttaacatt tttattttag gagttaaaaa      1680
ttttatcata ataattttat attataaaat a                                     1711

<210> SEQ ID NO 3
<211> LENGTH: 516
<212> TYPE: DNA
<213> ORGANISM: Plasmodium berghei

<400> SEQUENCE: 3
ttaatagaca tggacataaa ggtgttattt cttatattaa tgatattaat gatatgcctt        60
atttaaataa caaatacaa cctgatttat ttgtaagtgc tattggtata ccttctagaa       120
taaatatagg tcaaatatta gagggtatat atggattaaa tagtttatat ttaaataata       180
gatatataat atctaataat ttaaatacta attattataa taattatatt aataatttta       240
attattataa atataattat aataataatt ttgaattcaa taaaatatca tataattata       300
ataaatattt tttaaaaaat ccgtttacgg gccatttaat acagaatagt atttgtttaa       360
ataatattta ttattataaa ttagtacata tggtaaaaga taaattaaga tatagattca       420
taggattata ttctgaatta actcaacaac ctgtaaaagg aaatacaaaa caaggaggtc       480
aaagatttgg tgaaatggaa gtatgggcgc tagaag                                516

<210> SEQ ID NO 4
<211> LENGTH: 161
<212> TYPE: DNA
<213> ORGANISM: Plasmodium berghei

<400> SEQUENCE: 4
gttcaaaaat cagatttgac tgataacaca tggaacttca atccattgct ctaccattga        60
gctataatga cttaataata ttattattat aatagaatat aaccaaaagg ttaaggtaat       120
gaactttgat tcattaata taggttcgaa tcctttagga c                            161

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:
      oligonucleotide useful as a  primer.

<400> SEQUENCE: 5
gacctgcatg aaagatg                                                       17

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:
      oligonucleotide useful as a  primer.

<400> SEQUENCE: 6
gtatcgcttt aataggcg                                                      18

<210> SEQ ID NO 7
<211> LENGTH: 18
<212> TYPE: DNA
<213> ORGANISM: Artificial Sequence
```

```
<220> FEATURE:
<223> OTHER INFORMATION: Description of Artificial Sequence:
      oligonucleotide useful as a primer.

<400> SEQUENCE: 7
gccactacta tgaaaatc                                                    18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 8
gcgttcattc tgagctag                                                    18

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 9
gcggtaatac agaaaatgca agcg                                             24

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 10
agcacgaact gacgacagcc atgcac                                           26

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 11
atcaggaata cgtctagg                                                    18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 12
gctagtatta tgtcttct                                                    18

<210> SEQ ID NO 13
<211> LENGTH: 18
<212> TYPE: DNA
<213> ORGANISM: Artificial Sequence
<220> FEATURE:
```

```
<223> OTHER INFORMATION: Description of Artificial Sequence:
      oligonucleotide useful as a primer.

<400> SEQUENCE: 13
caccattaag tacatcac                                                18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 14
tgttaataca actccaat                                                18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 15
gctagtatta tgtcttca                                                18

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 16
ggaatgttat tgctaacac                                               19

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 17
gtaatcaatc tatgatac                                                18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 18
aatgaagagc tgtgtatc                                                18

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:
```

```
oligonucleotide useful as a primer.

<400> SEQUENCE: 19
gcgataagcc gacatcgagg tgcc                                          24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 20
tatcgtgttg catcgaatta agcc                                          24

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 21
cctcgactac cattttaata tcaataccta ccggta                             36

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence:
      oligonucleotide useful as  a primer.

<400> SEQUENCE: 22
aggtgcaatt attgcattgt ttacattagt aagta                              35

<210> SEQ ID NO 23
<211> LENGTH: 595
<212> TYPE: DNA
<213> ORGANISM: Plasmodium falciparum

<400> SEQUENCE: 23
gacctgcatg aaagatgtaa cgacttaaat gctgtcttaa aaaaaatctt aatgaaataa   60
aattatctgt gaagatacag atttcttata ttaggacaga aagaccctat gaagctttac  120
tattaataaa taatgaaaat atatatattt aacatagtat aaatgggaaa caataatatt  180
attttcttgg aaataattta gttaaaaatg aaataccatt ttatttatat ataaattctt  240
atagaaattt tataacaaat ttttaaacaa tatttatgag atagtttgac tggggcggtc  300
tcctcctata tataaacgga ggagtacaat gttatattta ttatataaag atataatata  360
taattaactg taaaatttac aaattaaaca gagataaatg tcggtcttaa tgatccgata  420
attatttagt aataaaatta tcgcttaacg gataaaagtt actctaggga taacaggcta  480
atcttttccg agagtccata ttgacgaaaa ggtttggcac ctcgatgtcg gcttatcgca  540
tcctaaagca gtagtatgtt ttaagggtaa gtctgttcgc ctattaaagc gatac       595

<210> SEQ ID NO 24
<211> LENGTH: 598
<212> TYPE: DNA
<213> ORGANISM: Plasmodium falciparum
```

-continued

```
<400> SEQUENCE: 24
gacctgcatg aaagatgtaa cgacttaaat gctgtcttaa aaaaaatctt aatgaaataa    60
aattatctgt gaagatacag atttcttata ttaggacagc aaagaccta tgaagctttta   120 ctattaataa ataatgaaaa tatatatatt aacatagta taaatgggaa acaataatat    180 tatttttctgg gaaataattt agttaaaaat gaaataccat tttatttata tataaatcct  240
tatagaaatt ttataacaga atttttagac aactattcat gagatagttt gactggggcg   300
gtctcctcct atatataaac ggaggagtac aatgttatat ttattatata agatataat    360 atataattaa ctgtaaaatt tacaaattaa acagagataa atgtcggtct taatgatccg   420
ataattattt agtaataaaa ttatcgctta acggataaaa gttactctag ggataacagg   480
ctaatctttt ccgagagtcc atattgacga aaaggtttgg cacctcgatg tcggcttatc   540
gcatcctaaa gcagtagtat gttttaaggg taagtctgtt cgcctattaa agcgatac    598

<210> SEQ ID NO 25
<211> LENGTH: 595
<212> TYPE: DNA
<213> ORGANISM: Plasmodium falciparum

<400> SEQUENCE: 25
gacctgcatg aaagatgtac cgacttaaat gctgtcttac aaaaaagctt aatgaaataa    60
aattatctgt gaagatacag atgtcttata ttaggacaga aagaccctat gaagctttgc   120
tattaataaa taatgaaaat atatatattt aacatagtat aaatgggaaa caataatatt   180
attttcttgg aaataattta gttaaaaatg aaataccatt ttatttatat ataaattctt   240
atagaaattt tataacaaat ttttaaacaa tatttatgag atagtttgac tggggcggtc   300
tcctcctata tataaacgga ggagtacaat gttatattta ttatataaag ataatatata   360
taattaactg taaaatttac aaattaaaca gagataaatg tcggtcttaa tgatccgata   420
attatttagt aataaaatta tcgcttaacg ataaaagtt actctaggga taacaggcta   480
atcttttccg agagtccata ttgacgaaaa ggtttggcac ctcgatgtcg gcttatcgca   540
tcctaaagca gtagtatgcc caagggtaa gtctgttcgc ctattaaagc gatac          595

<210> SEQ ID NO 26
<211> LENGTH: 595
<212> TYPE: DNA
<213> ORGANISM: Plasmodium falciparum

<400> SEQUENCE: 26
gacctgcatg aaagatgtaa cgacttaaat gctgtcttaa aaaaaatctt aatgaaataa    60
aattatctgt gaagatacag atttcttata ttaggacaga aagaccctat gaagctttac   120
tattaataaa taatgaaaat atatatattt aacatagtat aaatgggaaa caataatatt   180
attttcttgg aaataattta gttaaaaatg aaataccatt ttatttacat ataaattctt   240
atagaaattt tataacaaat ttttaaacaa tatttatgag atagtttgac tggggcggtc   300
tcctcctata tataaacaga ggagtacaat gttatattta ttatataaag ataatatata   360
taattaactg taaaatttac aaattaaaca gagataaatg tcggtcttaa tgatccgata   420
attatttagt aataaaatta tcgcttaacg ataaaagtt actctaggga taacaggcta   480
atcttttccg agagtccata ttgacgaaaa ggtttggcac ctcgatgtcg gcttatcgca   540
tcctaaagca gtagtatgtt ttaagggtaa gtctgttcgc ctattaaagc gatac          595
```

<210> SEQ ID NO 27
<211> LENGTH: 594
<212> TYPE: DNA
<213> ORGANISM: Plasmodium falciparum

<400> SEQUENCE: 27

| | | | | | |
|---|---|---|---|---|---|
| gacctgcatg | aaagatgtaa | cgacttaaat | gctgtcttaa | aaaaaatctt | aatgaaataa | 60 |
| aattatctgt | gaagatacag | atttcttata | ttaggacaga | aagaccctat | gaagctttac | 120 |
| tattaataaa | taatgaaaat | atatatattt | aacatagtat | aaatgggaaa | caataatatt | 180 |
| attttcttgg | aaataattta | gttaaaatga | aataccattt | tatttatata | taaattctta | 240 |
| tagaaatttt | ataacaaatt | tttaaacaat | atttatgaga | tagtttgact | ggggcggtct | 300 |
| cctcctatat | ataaacggag | gagtacaatg | ttatatttat | tatataaaga | tataatatat | 360 |
| aattaactgt | aaaatttaca | aattaaacag | agataaatgt | cggtcttaat | gatccgataa | 420 |
| ttatttagta | ataaaattat | cgcttaacg | ataaaagtta | ctctagggat | aacaggctaa | 480 |
| tcttttccga | gagtccatat | tgacgaaaag | gtttggcacc | tcgatgtcgg | cttatcgcat | 540 |
| cctaaagcag | tagtatgttt | taagggtaag | tctgttcgcc | tattaaagcg | atac | 594 |

<210> SEQ ID NO 28
<211> LENGTH: 595
<212> TYPE: DNA
<213> ORGANISM: Plasmodium falciparum

<400> SEQUENCE: 28

| | | | | | |
|---|---|---|---|---|---|
| gacctgcatg | aaagatgtaa | cgacttaaat | gctgtcttaa | aaaaaatctt | aatgaaataa | 60 |
| aattatctgt | gaagatacag | atttcttata | ttaggacagg | aagaccctat | gaagctttac | 120 |
| tattaataaa | taatgaaaat | atatatattt | aacatagtat | aaatgggaaa | caataatatt | 180 |
| attttcttgg | aaataattta | gttaaaaatg | aaataccatt | ttatttatat | ataaattctt | 240 |
| atagaaatttt | tataacaaat | ttttaaacaa | tatttatgag | atagtttgac | tggggcggtc | 300 |
| tcctcctata | tataaacgga | ggagtacaat | gttatattta | ttatataaag | atataatata | 360 |
| taattaactg | taaaatttac | aaattaaaca | gagataaatg | tcggtcttaa | tgatccgata | 420 |
| attatttagt | aataaaatta | tcgcttaacg | ataaaagtt | actctaggga | taacaggcta | 480 |
| atcttttccg | agagtccata | ttgacgaaaa | ggtttggcac | tcgatgtcg | gcttatcgca | 540 |
| tcctaaagca | gtagtatgtt | ttaagggtaa | gtctgttcgc | ctattaaagc | gatac | 595 |

<210> SEQ ID NO 29
<211> LENGTH: 594
<212> TYPE: DNA
<213> ORGANISM: Plasmodium vivax

<400> SEQUENCE: 29

| | | | | | |
|---|---|---|---|---|---|
| gacctgcatg | aaagatgtaa | cgacttaaat | gctgtcttaa | aaaaaatctt | aatgaaataa | 60 |
| aattatctgt | gaagatgcag | atttcttata | ttaggacaga | aagaccctat | gaagctttac | 120 |
| tatgaataga | tattgaaaat | atatatatag | agcatagcat | aaatgggaaa | taatgatatt | 180 |
| attttttttgg | aaatagtgta | attgtaaatg | aaataccatt | ttttatatat | ataaattctt | 240 |
| aaaaaaattt | tttaacaaat | ttttttaacag | tattttataag | atagtttgac | tggggcggtc | 300 |
| tcctcctata | taaaaacgga | ggagtacaaa | gttatatatg | ttatataaag | atatatatat | 360 |
| aattaactgt | aaaattaaca | aattaaacag | agattaatgt | cggtcttaat | gatccgataa | 420 |
| ttatttaatg | ataaaattat | cgcttaacgg | ataaaagtta | ctctagggat | aacaggctaa | 480 |

```
tcttttccga gagtccatat tgacgaaaag gtttggcacc tcgatgtcgg cttatcgcat      540
cctaaagcag tagtatgttt taagggtaag tctgttcgcc tattaaagcg atac            594
```

<210> SEQ ID NO 30
<211> LENGTH: 594
<212> TYPE: DNA
<213> ORGANISM: Plasmodium vivax

<400> SEQUENCE: 30

```
gacctgcatg aaagatgtaa cgacttaaat gctgtcttaa aaaaatctt aatgaaataa        60 aattatctgt gaagatgcag atttcttata ttaggacaga aagaccctat gaagctttac      120
tatgaataga tattgaaaat atatatatag agcatagcat aaatgggaaa taatgatatt      180 attttttttgg aaatagtgta attgtaaatg aaataccatt ttttatatat ataaattctt     240
aaaaaaattt tttaacaaat ttttaacag tatttataag atagtttgac tggggcggtc      300
tcctcctata taaaaacgga ggagtacaaa gttatatatg ttatataaag atatatatat      360
aattaactgt aaaattcaca aattacacag agattaatgt cggtcttaat gatccgataa      420
ttatttaatg ataaaattat cgcttaacgg ataaaagtta ctgtagggat aacaggctaa     480
tcttttccga gagtccatat tgacgaaaag gttcggcacc tcgatgtcgg cttatcgcat     540
cctaaagcag tagtatgttt taagggtaag tctgttcgcc tattaaagcg atac           594
```

<210> SEQ ID NO 31
<211> LENGTH: 596
<212> TYPE: DNA
<213> ORGANISM: Plasmodium vivax

<400> SEQUENCE: 31

```
gacctgcatg aaagatgtaa cgacttaaat gctgtcttaa aaaaactctt aatgaaataa      60
aattatctgt gaagatacag atttcttata ttaggacaga aagaccctat gaagctttac     120
tattaataaa taatgaaaat atatatatttt aacatagtat aaatgggaaa caataatatt    180
attttcttgg aaataattta gttaaaaatg aaataccatt ttatttatat ataaattctt     240
atagaaattt tataacaaat ttttaaacaa tatttatgag atagtttgac tggggcggtc     300
tcctcctata tataaacgga ggagtacaat gttatattta ttatataaag ataataata     360 taattaactg taaaatttac aaattaaaca gagataaatg tcggtcttaa tgatccgata    420
attatttagt aataaaatta tcgcttaacg gataaaagtt actctaggga taacaggcta    480
atcttttccg agagtccata ttgacgaaaa ggtttggcac ctcgatgtcg gcttatcgca    540
tcctaaagca gtagtatgtt ttaagggtaa gtctgttacg cctattaaag cgatac         596
```

<210> SEQ ID NO 32
<211> LENGTH: 596
<212> TYPE: DNA
<213> ORGANISM: Plasmodium vivax

<400> SEQUENCE: 32

```
gacctgcatg aaagatgtaa cgacttaaat gctgtcttaa aaaaaatctt aatgaaataa    60
aattatctgt gaagatacag atttcttata ttaggacaga aagaccctat gaagctttac   120
tattaataaa taatgaaaat atatatattt aacatagtat aaatgggaaa caataatatt   180
attttcttgg aaataattta gttaaaaatg aaataccatt ttatttatat ataaattctt   240
atagaaattt tataacaaat ttttaaacaa tatttatgag atagtttgac tggggcggtc   300
tcctcctata tataaacgga ggagtacaat gttatattta ttatataaag ataataata    360
```

-continued

```
taattaactg taaaatttac aaattaaaca gagataaatg tcggtcttaa tgatccgata      420
attatttagt aataaaatta tcgcttaacg gataaaagtt actctaggga taacaggcta      480
atcttttccg agagtccata ttgacgaaaa ggtttggcac ctcgatgtcg gcttatcgca      540
tcctaaagca gtagtatgtt ttaagggtaa gtctgtttcg cctattaaag cgatac         596
```

<210> SEQ ID NO 33
<211> LENGTH: 594
<212> TYPE: DNA
<213> ORGANISM: Plasmodium vivax

<400> SEQUENCE: 33

```
gacctgcatg aaagatgtaa cgacttaaat gctgtcttaa aaaaaatctt aatgaaataa      60
aattatctgt gaagatgcag atttcttata ttaggacaga aagaccctat gaagctttac      120
tatgaataga tattgaaaat atatatatag agcatagcat aaatgggaaa taatgatatt      180 attttttttgg aaatagtgta attgtaaatg aaataccatt ttttatatat ataaattctt     240
aaaaaaattt tttaacaaat tttttaacag tatttataag atagtttgac tggggcggtc      300
tcctcctata taaaaacgga ggagtacaaa gttatatatg ttatataaag atatatatat      360
aattaactgt aaaattaaca aattaaacag agattaatgt cggtcttaat gatccgataa      420
ttatttaatg ataaaattat cgcttaacgg ataaaagtta ctctagggat aacaggctaa      480
tcttttccga gagtccatat tgacgaaaag gtttggcacc tcgatgtcgg cttatcgcat      540
cctaaagcag tagtatgttt taagggtaag tctgttcgcc tattaaagcg atac           594
```

<210> SEQ ID NO 34
<211> LENGTH: 594
<212> TYPE: DNA
<213> ORGANISM: Plasmodium vivax

<400> SEQUENCE: 34

```
gacctgcatg aaagatgtaa cgacttaaat gctgtcttaa aaaaaatctt aatgaaataa      60 aattaccctgt gaagatgcag atttcttata ttaggacaga aagaccctat gaagctttac     120
tatgaataga tattgaaaat atatatatag agcatagcat aaatgggaaa taatgatatt      180
attttttggg aaatagtgta attgtaaatg aaataccatt ttttatatat ataaatcctt      240
aaaaaaattt tttaacaaat tttttaacag tatttataag atagtttgac tggggcggtc      300
tcctcctata taaaaacgga ggagtacaaa gttatatatg ttatataaag atatatatat      360
aattaactgt aaaattgaca aattaaacag agattaatgt cggtcttaat gatccgataa      420
ttatttaatg ataaaattat cgcttaacgg ataaaagtta ctctagggat aacaggctaa      480
ccttttccga gagtccatat tgacgaaaag gtttggcacc tcgatgtcgg cttatcgcat      540
cctaaagcag tagtatgttt taagggtaag tctgttcgcc tattaaagcg atac           594
```

<210> SEQ ID NO 35
<211> LENGTH: 593
<212> TYPE: DNA
<213> ORGANISM: Plasmodium malariae

<400> SEQUENCE: 35

```
gacctgcatg aaagatgtaa cgacttaaat gctgtcttaa aaaaaatctt aatgaaataa      60
aattatctgt gaagatgcag atttcttata ttaggacaga aagaccctat gaagctttac      120
tatgaataga tattgaaaat atatatatag agcatagcat aaatgggaaa taatgatatt      180
```

```
atttttttgg aaatagtgta attgtaaatg aaataccatt ttttatatat ataaattctt    240
aaaaaaattt ttaacaaatt ttttaacagt atttataaga tagtttgact ggggcggtct    300
cctcctatat aaaacggag gagtacaaag ttatatatgt tatataaaga tatatatata    360
attaactgta aaattaacaa attaaacaga gattaatgtc ggtcttaatg atccgataat    420
tatttaatga taaaattatc gcttaacgga taaaagttac tctagggata acaggctaat    480
cttttccgag agtccatatt gacgaaaagg tttggcacct cgatgtcggc ttatcgcatc    540
ctaaagcagt agtatgtttt aagggtaagt ctgttcgcct attaaagcga tac           593
```

<210> SEQ ID NO 36
<211> LENGTH: 595
<212> TYPE: DNA
<213> ORGANISM: Plasmodium malariae

<400> SEQUENCE: 36

```
gacctgcatg aaagatgtaa cgacttaaat gctgtcttaa aaaaaatctt aatgaaataa    60
aattatctgt gaagatgcag atttcttata ttaggacaga aagaccctat gaagctttac   120
tatgaataga tattgaaaat atatatatag agcatagcat aaatgggaaa taatgatatt   180
atttttttgg aaatagtgta attgtaaatg aaataccatt ttttatatat ataaattctt   240
aaaaaaattt ttaacaaat ttttaacag tatttataag atagtttgac tggggcggt    300 ctcctcctat ataaaacgg aggagtacaa agttatatat gttatataaa gatatatata    360
taattaactg taaaattaac aagttaaaca gagattaatg tcggtcttaa tgatccgata   420
attatttaat gataaaatta tcgcttaacg gataaaagtt actctaggga taacaggcta   480
atcttttccg agagtccata ttgacgaaaa ggtttggcac ctcgatgtcg gcttatcgca   540
tcctaaagca gtagtatgtt ttaagggtaa gtctgttcgc ctattaaagc gatac         595
```

<210> SEQ ID NO 37
<211> LENGTH: 594
<212> TYPE: DNA
<213> ORGANISM: Plasmodium ovale

<400> SEQUENCE: 37

```
gacctgcatg aaagatgtaa cgacttaaat gctgtcttaa aaaaaatctt aatgaaataa    60
aattatctgt gaagatgcag atttcttata ttaggacaga aagaccctat gaagctttac   120
tatgaataga tattgaaaat atatatatag agcatagcat aaatgggaaa taatgatatt   180
atttttttgg aaatagtgta attgtaaatg aaataccatt ttttatatat ataaattctt   240
aaaaaaattt tttaacaaat ttttaacag tatttataag atagtttgac tggggcggtc   300
tcctcctata taaaacgga ggagtacaaa gttatatatg ttatataaag atatatatat   360
aattaactgt aaaattaaca aattaaacag agattaatgt cggtcttaat gatccgataa   420
ttatttaatg ataaaattat cgcttaacgg ataaaagtta ctctagggat aacaggctaa   480
tcttttccga gagtccatat tgacgaaaag gtttggcacc tcgatgtcgg cttatcgcat   540
cctaaagcag tagtatgttt taagggtaag tctgttcgcc tattaaagcg atac           594
```

<210> SEQ ID NO 38
<211> LENGTH: 594
<212> TYPE: DNA
<213> ORGANISM: Plasmodium ovale

<400> SEQUENCE: 38

| | |
|---|---|
| gacctgcatg aaagatgtaa cgacttaaat gctgtcttaa aaaaaatctt aatgaaataa | 60 |
| aattatctgt gaagatgcag atttcttata ttaggacaga aagaccctat gaagctttac | 120 |
| tatgaataga tattgaaaat atatatatag agcatagcat aaatgggaaa taatgatatt | 180 |
| attttttgg aaatagtgta attgtaaatg aaataccatt ttttatatat ataaattctt | 240 |
| aaaaaattt tttaacaaat tttttaacag tatttataag atagtttgac tggggcggtc | 300 |
| tcctcctata taaaaacgga ggagtacaaa gttatatatg ttatataaag atatatatat | 360 |
| aattaactgt aaaattaaca aattaaacag agattaatgt cggtcttaat gatccgataa | 420 |
| ttatttaatg ataaaattat cgcttaacgg ataaaagtta ctctagggat aacaggctaa | 480 |
| tcttttccga gagtccatgt tgacgaaaag gtttggcacc tcgatgtcgg cttatcgcat | 540 |
| cctaaagcag tagtatgttt taagggtaag tctgttcgcc tattaaagcg atac | 594 |

<210> SEQ ID NO 39
<211> LENGTH: 594
<212> TYPE: DNA
<213> ORGANISM: Plasmodium berghei

<400> SEQUENCE: 39

| | |
|---|---|
| gacctgcatg aaagatgtaa cgacttaaat gctgtcttaa aaaaaatctt aatgaaataa | 60 |
| aattatctgt gaagatgcag atttcttata ttaggacaga aagaccctat gaagctttac | 120 |
| tattaataga tattgaaaat atatatatat aacatagaat aaatgggaag tagtaatatt | 180 |
| attttttgg aaataatgta attgttaatg aaataccatt ttatatatat ataaattctt | 240 |
| ataaaatttt tataacaaaa tttttaacaa tatttataag atagtttgac tggggcggtc | 300 |
| tcctcctata taaaaacgga ggtgtacaat gttatatta ttatataaag ataaatatat | 360 |
| aattaactgt aaaatttaca aattaaacag agattaatgt cggtcttaat gatccgataa | 420 |
| ttatttaata ataaaattat cgcttaacgg ataaaagtta ctctagggat aacaggctaa | 480 |
| tcttttccga gagtccatat tgacgaaaag gtttggcacc tcgatgtcgg cttatcgcat | 540 |
| cctaaggcag tagtatgttt taagggtaag tctgttcgcc tattaaagcg atac | 594 |

<210> SEQ ID NO 40
<211> LENGTH: 1563
<212> TYPE: DNA
<213> ORGANISM: Plasmodium falciparum

<400> SEQUENCE: 40

| | |
|---|---|
| armgactgta tggatcaaat atttctcatt tatatccgag cctcatgtta tttttattgt | 60 |
| tttaaataga tattcactta ttacaaattg taaccataaa actttaggat tatactattt | 120 |
| atggttttca ttttttatttg gtagttatgg atttttatta tcagtaatac tacgtactga | 180 |
| attatattct tcatctttaa gaataattgc acaagaaaat gtaaatctat ataatatgat | 240 |
| atttacaatt cacggaataa ttatgatttt tttcaatata atgccaggat tattcggagg | 300 |
| atttggtaat tactttctac ctattttatg tggatctcca gaattagcat atcctagaat | 360 |
| taatagtata tctttactgt tacaaccaat tgcttttgtt ttagttatat tatctactgc | 420 |
| agcagaattt ggtggtggaa ctggatggac tttatatcca ccattaagta catctttaat | 480 |
| gtcattatct cctgtagctg tagatgtaat aattttttggt ttattagtat ctggagtcgc | 540 |
| tagtattatg tcttcattaa atttattac tacagtaatg catttaagag caaaaggatt | 600 |
| aacacttggt atattaagtg tttctacatg gtcattgatc attacatcag gaatgttatt | 660 |
| gctaacacta ccggttttaa ctggaggagt attaatgtta ttatcagact acattttaa | 720 |

-continued

```
tactttattt tttgacccaa catttgcagg agatccaata ttatatcaac atttattctg      780
gttttttgga catcctgaag tatacatttt aatattacct gcttttggag taattagtca      840
tgtaatttct actaattatt gcagaaatct atttggtaat caatctatga tacttgctat      900
gggatgtata gctgttttag gaagcttagt atgggtacat catatgtaca ctactggttt      960
agaagttgat actagagctt attttacttc gactaccatt ttaatatcaa tacctaccgg     1020
tacaaaagta tttaactgga tatgtacata tatgagtagt aattttggta tgatacacag     1080
ctcttcatta ttgtcattat tatttatatg tacatttaca tttggaggta ctactggagt     1140
tatattaggt aatgctgcca ttgatgtagc attacatgac acatattatg ttattgctca     1200
tttccatttt gtactatcaa ttggtgcaat tattggatta tttacaactg taagtgcatt     1260
tcaagataat ttctttggta aaaacttacg tgaaaattct attgtaatac tatggtcaat     1320
gttatttttt gtaggtgtaa tattaacatt tttacctatg cattttttag gatttaatgt     1380
aatgcctaga cgtattcctg attatccaga cgctttaaat ggatggaata tgatttgttc     1440
tattgggtca acaatgactt tatttggttt actaattttt aaataatatt actatttatt     1500
gttttttatga acttttactc tattaattta gttaaagcac acttaataaa ttacccatgt     1560
cca                                                                   1563
```

<210> SEQ ID NO 41
<211> LENGTH: 1563
<212> TYPE: DNA
<213> ORGANISM: Plasmodium falciparum

<400> SEQUENCE: 41

```
armgactgta tggatcgaat atttctcatt tatatccgag cctcatgtta tttttattgt       60
tttaaataga tattcactta ttacaaattg taaccataaa actttaggat tatactattt      120
atggttttca tttttatttg gtagttatgg atttttatta tcagtaatac tacgtactga      180
attatattct tcatctttaa gaataattgc acaagaaaat gtaaatctat ataatatgat      240
atttacaatt cacggaataa ttatgatttt tttcaatata atgccaggat tattcggagg      300
atttggtaat tactttctac ctattttatg tggatctcca gaattagcat atcctagaat      360
taatagtata tctttactgt tacaaccaat tgcttttgtt ttagttatat tatctactgc      420
agcagaattt ggtggtggaa ctggatggac tttatatcca ccattaagta catctttaat      480
gtcattatct cctgtagctg tagatgtaat aattttggt ttattagtat ctggagtcgc      540
tagtattatg tcttcattaa atttttattac tacagtaatg catttaagag caaaaggatt      600
aacacttggt atattaagtg tttctacatg gtcattgatc attacatcag gaatgttatt      660
gctaacacta ccggttttaa ctggaggagt attaatgtta ttatcagact tacattttaa      720
tactttattt tttgacccaa catttgcagg agatccaata ttatatcaac atttattctg      780
gttttttgga catcctgaag tatacatttt aatattacct gcttttggag taattagtca      840
tgtaatttct actaattatt gcagaaatct atttggtaat caatctatga tacttgctat      900
gggatgtata gctgttttag gaagcttagt atgggtacat catatgtaca ctactggttt      960
agaagttgat actagagctt attttacttc gactaccatt ttaatatcaa tacctaccgg     1020
tacaaaagta tttaactgga tatgtacata tatgagtagt aattttggta tgatacacag     1080
ctcttcatta ttgtcattat tatttatatg tacatttaca tttggaggta ctactggagt     1140
tatattaggt aatgctgcca ttgatgtagc attacatgac acatattatg ttattgctca     1200
```

```
tttccatttt gtactatcaa ttggtgcaat tattggatta tttacaactg taagtgcatt    1260
tcaagataat ttctttggta aaacttacg tgaaaattct attgtaatac tatggtcaat    1320 gttattttt gtaggtgtaa tattaacatt tttacctatg cattttttag gatttaatgt    1380
aatgcctaga cgtattcctg attatccaga cgctttaaat ggatggaata tgatttgttc    1440
tattgggtca acaatgactt tatttggttt actaattttt aaataatatt actatttatt    1500
gtttttatga acttttactc tattaattta gttaaagcac acttaataaa ttacccatgt    1560
cca                                                                 1563

<210> SEQ ID NO 42
<211> LENGTH: 1584
<212> TYPE: DNA
<213> ORGANISM: Plasmodium vivax

<400> SEQUENCE: 42
gactgtatgg atcgaatctt acttattcat atccaagcct cacttattgt taattatata      60
ttatattttt tttttgtttc caatagatat acacttatta caaattgcaa tcataaaact    120
ttaggtctat actattatg gttttcattt ttatttggta gttatggttt tttattatct    180
gttattttac gtacagaatt atattcttct tctttaagaa taattgcaca agaaaatgtt    240
aacttatata atatgatatt tacattacat ggaattatta tgatattctt taatataatg    300
ccaggattat ttgaggatt cggtaattac ttcctaccaa tttttatgtgg ttctccagaa    360 cttgcatatc caagaattaa tagtatatct ttattattac aaccaatagc ttttatatta    420 gtcatttat ctacagcagc agaatttgga ggaggtactg gatggacttt atatccacca    480
ttaagtacat cacttatgtc tttatctcct gttgcagtag atgttatcat tgttggtctt    540
ttagtatctg gtattgctag tattatgtct tctttaaatt ttattactac tgtaatgcat    600
ctaagatcta aaggtttaac acttggtata ttaagtgtat ctacatggtc attaataatt    660
acatctgtaa tgctattatt aacattacct gttttaacag gtggtgtttt aatgttatta    720
tcagatttac attttaatac attattttt gatcctacat ttgctggaga tcctattta    780 tatcaacatc tatttggtt ttttggacat cctgaagtgt atatttaat attaccagca    840 tttggtgtta ttagtcatgt aatatctaca aattattgta gaagttattt tggtaatcaa    900
tctatgattt tagcaatgag ttgtattgct atattaggaa gtgttgtatg ggctcatcat    960
atgtatacta caggtttaga agtagataca agagcatttt ttacatctac aactatatta    1020
atatctatac ctactggaac aaaaatatt aattggatat gtacatatat gggtagtaat    1080
tttggtataa ctcatagttc atctttatta tcattactat ttatatgtac atttactttt    1140
ggtggtacta caggagtaat attaggtaat gcagctattg atattgcatt acatgatact    1200
tactatgtaa tcgctcattt ccatttgta ttatctatag gtgcaattat tgcattgttt    1260
acattagtaa gtagttttca agaaactttt tttggtaaac atttacgtga aaattctata    1320
ataatattat ggtcaatctt atttttatt ggagttgtat taacattctt acctatgcat    1380
tttcttggat ttaatgtaat gcctagacgt attcctgatt atccagacgc tttaaatgga    1440
tggaatatga tttgttcaat tggatcaaca atgactttat tggtttatt tatttttaaa    1500 taatataaaa tatttttgt ttatatgaat tattattcta ttaatttagc aaaagcacat    1560
ttattaaatt acccatgtcc atta                                          1584

<210> SEQ ID NO 43
<211> LENGTH: 1582
```

<212> TYPE: DNA
<213> ORGANISM: Plasmodium vivax

<400> SEQUENCE: 43

```
gactgtatgg atcgaatctt acttattcat atccaagcct cacttattgt taattatata      60
ttatatttt tttgttttca atagatatac acttattaca aattgcaatc ataaaacttt      120
aggtctatac tatttatggt tttcattttt atttggtagt tatggttttt tattatctgt     180
tattttacgt acagaattat attcttcttc tttaagaata attgcacaag aaaatgttaa     240
cttatataat atgatattta cattacatgg aattattatg atattcttta atataatgcc     300
aggattattt ggaggattcg gtaattactt cctaccaatt ttatgtggtt ctccagaact     360
tgcatatcca agaattaata gtatatcttt attattacaa ccaatagctt ttatattagt     420
aattttatct acagcagcag aatttggagg aggtactgga tggactttat atccaccatt     480
aagtacatca cttatgtctt tatctcctgt tgcagtagat gttatcattg ttggtctttt     540
agtatctggt attgctagta ttatgtcttc tttaaatttt attactactg taatgcatct     600
aagatctaaa ggtttaacac ttggtatatt aagtgtatct acatggtcat aataattac      660
atctgtaatg ctattattaa cattacctgt tttaacaggt ggtgttttaa tgttattatc     720
agatttacat tttaatacat tattttttga tcctacattt gctggagatc ctatttata     780
tcaacatcta ttttggtttt tggacatcc tgaagtgtat attttaatat caccagcatt     840
tggtgttatt agtcatgtaa tatctacaaa ttattgtaga agtttatttg gtaatcaatc     900
tatgatttta gcaatgagtt gtatagctat attaggaagt gttgtatggg ctcatcatat     960
gtatactaca ggtttagaag tagatacaag agcattttt acatctacaa ctatattaat    1020
atctatacct actggaacaa aaatatttaa ttggatatgt acacatatgg gtagtaattt    1080
tggtataact catagttcat ctttattatc attactattt atatgtacat ttacttttgg    1140
tggtactaca ggagtaatat taggtaatgc agctattgat attgcattac atgatactta    1200
ctatgtaatc gctcatttcc attttgtatt atctataggt gcaattattg cattgtttac    1260
attagtaagt agttttcaag aaaactttt tggtaaacat ttacgtgaaa attctataat    1320
aatattatgg tcaatcttat tttttattgg agttgtatta acattcttac ctatgcattt    1380
tcttggattt aatgtaatgc ctagacgtat tcctgattat ccagacgctt taatggatg    1440
gaatatgatt tgttcaattg gatcaacaat gactttattt ggtttattta ttttaaaata    1500
atataaaata ttttttgttt atatgaatta ttattctatt aatttagcaa aagcacattt    1560
attaaattac ccatgtccat ta                                              1582
```

<210> SEQ ID NO 44
<211> LENGTH: 1583
<212> TYPE: DNA
<213> ORGANISM: Plasmodium vivax

<400> SEQUENCE: 44

```
gactgtatgg atcgaatctt acttattcat atccaagcct cacttattgt taattatata      60
ttatatttt tttgttttcc aatagatata cacttattac aaattgcaat cataaaactt     120
taggtctata ctatttatgg ttttcatttt tatttggtag ttatggtttt ttattatctg     180
ttattttacg tacagaatta tattcttctt ctttaagaat aattgcacaa gaaaatgtta     240
acttatataa tatgatattt acattacatg gaattattat gatattcttt aatataatgc     300
caggattatt tggaggattc ggtaattact tcctaccaat tttatgtggt tctccagaac     360
```

-continued

```
ttgcatatcc aagaattaat agtatatctt tattattaca accaatagct tttatattag      420
tcattttatc tacagcagca gaatttggag gaggtactgg atggacttta tatccaccat      480
taagtacatc acttatgtct ttatctcctg ttgcagtaga tgttatcatt gttggtcttt      540
tagtatctgg tattgctagt attatgtctt ctttaaattt tattactact gtaatgcatc      600
taagatctaa aggtttaaca cttggtatat aagtgtatc tacatggtca ttaataatta      660
catctgtaat gctattatta acattacctg ttttaacagg tggtgtttta atgttattat      720
cagatttaca ttttaataca ttattttttg atcctacatt tgctggagat cctatttat       780 atcaacatct attttggttt tttggacatc ctgaagtgta tattttaata ttaccagcat      840
ttggtgttat tagtcatgta atatctacaa attattgtag aagtttatt ggtaatcaat       900 ctatgatttt agcaatgagt tgtattgcta tattaggaag tgttgtatgg gctcatcata      960
tgtatactac aggtttagaa gtagatacaa gagcattttt tacatctaca actatattaa    1020
tatctatacc tactggaaca aaaatattta attggatatg tacatatatg ggtagtaatt    1080
ttggtataac tcatagttca tctttattat cattactatt tatatgtaca tttacttttg    1140
gtggtactac aggagtaata ttaggtaatg cagctattga tattgcatta catgatactt    1200
actatgtaat cgctcatttc cattttgtat tatctatagg tgcaattatt gcattgttta    1260
cattagtaag tagttttcaa gaaaactttt tggtaaaca tttacgtgaa aattctataa     1320
taatattatg gtcaatctta ttttttattg gagttgtatt aacattctta cctatgcatt    1380
ttcttggatt taatgtaatg cctagacgta ttcctgatta tccagacgct ttaaatggat    1440
ggaatatgat tgttcaatt ggatcaacaa tgactttatt tggtttattt attttttaaat    1500 aatataaaat attttttgtt tatatgaatt attattctat taatttagca aaagcacatt    1560
tattaaatta cccatgtcca tta                                            1583
```

<210> SEQ ID NO 45
<211> LENGTH: 1582
<212> TYPE: DNA
<213> ORGANISM: Plasmodium vivax

<400> SEQUENCE: 45

```
gactgtatgg atcgaatctt acttattcat atccaagcct cacttattgt taattatata      60
ttatattttt tttgtttcca atagatatac acttattaca aattgcaatc ataaaacttt     120
aggtctatac tatttatggt cttcattttt atttggtagt tatggttttt tattatctgt     180
tattttacgt acagaattat attcttcttc tttaagaata attgcacaag aaaatgttaa     240
cttatataat atgatattta cattacatgg aattattatg atattcttta atataatgcc     300
aggattattt ggaggattcg gtaattactt cctaccaatt ttatgtggtt ctccagaact     360
tgcatatcca agaattaata gtatatcttt attattacaa ccaatagctt ttatattagt     420
cattttatct acagcagcag aatttggagg aggtactgga tggactttat atccaccatt     480
aagtacatca cttatgtctt tatctcctgt tgcagtagat gttatcattg ttggtctttt     540
agtatctggt attgctagta ttatgtcttc tttaaatttt attactactg taatgcatct     600
aagatctaaa ggtttaacac ttggtatatt aagtgtatct acatggtcat taataattac     660
atctgtaatg ctattattaa cattacctgt tttaacaggt ggtgttttaa tgttattatc     720
agatttacat tttaatacat tattttttga tcctacattt gctggagacc tattttata     780 tcaacatcta ttttggtttt ttggacatcc tgaagtgtat attttaatat taccagcatt     840
tggtgttatt agtcatgtaa tatctacaaa ttattgtaga agtttatttg gtaatcaatc     900
```

```
tatgatttta gcaatgagtt gtattgctat attaggaagt gttgtatggg ctcatcatat      960
gtatactaca ggtttagaag tagatacaag agcattttt acatctacaa ctatattaat     1020
atctatacct actggaacaa aaatatttaa ttggatatgt acatatatgg gtagtaattt    1080
tggtataact catagttcat ctttattatc attactattt atatgtacat ttacttttgg    1140
tggtactaca ggagtaatat taggtaatgc agctattgat attgcattac atgatactta    1200
ctatgtaatc gctcatttcc attttgtatt atctataggt gcaattattg gattgtttac    1260
attagtaagt agttttcaag aaaacttttt tggtaaacat ttacgtgaaa attctataat    1320
aatattatgg tcaatcttat tttttattgg agttgtatta acattcttac ctatgcattt    1380
tcttggattt aatgtaatgc ctagacgtat tcctgattat ccagacgctt taaatggatg    1440
gaatatgatt tgttcaattg gatcaacaat gactttattt ggtttatttta tttttaaata    1500
atataaaata tttttttgttt atatgaatta ttattctatt aatttagcaa aagcacattt    1560
attaaattac ccatgtccat ta                                             1582

<210> SEQ ID NO 46
<211> LENGTH: 1581
<212> TYPE: DNA
<213> ORGANISM: Plasmodium ovale

<400> SEQUENCE: 46
gactgtatgg atcgaatctt acttattcat atccaagcct cactattgt taattatata     60
ttatattttt ttgttttcaa tagatataca cttattacaa attgcaatca taaaacttta   120
ggtctatact atttatggtt ttcatttta tttggtagtt atggtttttt attatctgtt    180
attttacgta cagaattata ttcttcttct ttaagaataa ttgcacaaga aaatgttaac    240
ttatataata tgatatttac attacatgga attattatga tattctttaa tataatgcca   300
ggattatttg gaggattcgg taattacttc ctaccaattt tatgtggttc tccagaactt   360
gcatatccaa gaattaatag tatatcttta ttattacaac caatagcttt tatattagtc   420
attttatcta cagcagcaga atttggagga ggtactggat ggactttata tccaccatta   480
agtacatcac ttatgtcttt atctcctgtt gcagtagatg ttatcattgt tggtctttta   540
gtatctggta ttgctagtat tatgtcttct ttaaatttta ttactactgt aatgcatcta   600
agatctaaag gtttaacact tggtatatta agtgtatcta catggtcatt aataattaca   660
tctgtaatgc tattattaac attacctgtt ttaacaggtg gtgttttaat gttattatca   720
gatttacatt ttaatacatt atttttgat cctacatttg ctggagatcc tattttatat   780
caacatctat tttggttttt tggacatcct gaagtgtata tttttaatatt accagcattt    840
ggtgttatta gtcatgtaat atctacaaat tattgtagaa gtttatttgg taatcaatct    900
atgattttag caatgagttg tattgctata ttaggaagtg ttgtatgggc tcatcatatg    960
tatactacag gtttagaagt agatacaaga gcattttta catctacaac tatattaata   1020
tctataccta ctggaacaaa aatatttaat tggatatgta catatatggg tagtaatttt   1080
ggtataactc atagttcatc tttattatca ttactattta tatgtacatt tacttttggt   1140
ggtactacag gagtaatatt aggtaatgca gctattgata ttgcattaca tgatacttac   1200
tatgtaatcg ctcatttcca ttttgtatta tctataggtg caataattgc attgtttaca   1260
ttagtaagta gttttcaaga aaactttttt ggtaaacatt tacgtgaaaa ttctataata   1320
atattatggt caatcttatt ttttattgga gttgtattaa cattcttacc tatgcatttc   1380
```

| | |
|---|---|
| cttggattta atgtaatgcc tagacgtatt cctgattatc cagacgcttt aaatggatgg | 1440 |
| aatatgattt gttcaattgg atcaacaatg actttatttg gtttatttat ttttaaataa | 1500 |
| tataaaatat tttttgttta tatgaattat tattctatta atttagcaaa agcacattta | 1560 |
| ttaaattacc catgtccatt a | 1581 |

<210> SEQ ID NO 47
<211> LENGTH: 1417
<212> TYPE: DNA
<213> ORGANISM: Plasmodium malariae

<400> SEQUENCE: 47

| | |
|---|---|
| gactgtatgg atcgaatctt acttattcat atccaagcct cacttattgt taattatata | 60 |
| ttatattttt tttgttttca atagatatac acttattaca aattgcaatc ataaaacttt | 120 |
| aggtctatac tatttatggt tttcattttt atttggtagt tatggttttt tattatctgt | 180 |
| tattttacgt acagaattat attcttcttc tttaagaata attgcacaag aaaatgctaa | 240 |
| cttatataat atgatattta cattacatgg aattattatg atattcttta atataatgcc | 300 |
| aggattattt ggaggattcg gtaattactt cctaccaatt ttatgtggtt ctccagaact | 360 |
| tgcatatcca agaattaata gtatatcttt attattacaa ccaatagctt ttatattagt | 420 |
| cattttatct acagcagcag aatttggagg aggtactgga tggactttat atccaccatt | 480 |
| aagtacatca cttatgtctt tatctcctgt tgcagtagat gttatcattg ttggtctttt | 540 |
| agtatctggt attgctagta ttatgtcttc tttaaatttt attactactg taatgcatct | 600 |
| aagatctaaa ggtttaacac ttggtatatt aagtgtatct acatggtcat taataattac | 660 |
| atctgtaatg ctattattaa cattacctgt tttaacaggt ggtgttttaa tgttattatc | 720 |
| agatttacat tttaatacat tatcttttga tcctacattt gctggagatc ctattttata | 780 |
| tcaacatcta ttttggtttt ttggacatcc tgaagtgtat attttaatat taccagcatt | 840 |
| tggtgttatt agtcatgtaa tatctacaaa ttattgtaga gtttatttg gtaatcaatc | 900 |
| tatgatttta gcaatgagtt gtattgctat attaggaagt gttgtatggg ctcatcatat | 960 |
| gtatactaca ggtttagaag tagatacaag agcatttttt acatctacaa ctatattaat | 1020 |
| atctataccct actggaacaa aaatatttaa ttggatatgt acatatatgg gtagtaattt | 1080 |
| tggtataact catagttcat ctttattatc attactattt atatgtacat ttactttgg | 1140 |
| tggtactaca ggagtaatat taggtaatgc agctattgat attgcattac atgatactta | 1200 |
| ctatgtaatc gctcatttcc attttgtatt atctataggt gcaattattg cattgtttac | 1260 |
| attagtaagt agttttcaag aaaactttt tggtaaacat ttacgtgaaa attctataat | 1320 |
| aatattatgg tcaatcttat tttttattgg agttgtatta acattcttac ctatgcattt | 1380 |
| ccttggattt aatgtaatgc ctagacgtat tcctgat | 1417 |

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 48

| | |
|---|---|
| gcaatatgtg catgttgtaa a | 21 |

<210> SEQ ID NO 49

```
<211> LENGTH: 18
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 49
attctttata aacagacg                                             18

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 50
gggcgacgag gcccagagc                                            19

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 51
gcatcctgtc ggcaatgcc                                            19

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence:
      oligonucleotide useful as  primer.

<400> SEQUENCE: 52
aaggagaagc tgtgctac                                             18

<210> SEQ ID NO 53
<211> LENGTH: 17
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 53
tcatgatgga gttgaag                                              17
```